US012667434B2

(12) United States Patent
Khurana et al.

(10) Patent No.: US 12,667,434 B2
(45) Date of Patent: Jun. 30, 2026

(54) SURGICAL SYSTEMS AND METHODS FOR GUIDING ROBOTIC MANIPULATORS

(71) Applicant: MAKO Surgical Corp., Weston, FL (US)

(72) Inventors: Rishabh Khurana, Fort Lauderdale, FL (US); David Gene Bowling, Los Ranchos De Albuquerque, NM (US); Matthew Thompson, Woodbridge, CT (US)

(73) Assignee: MAKO Surgical Corp., Weston, FL (US)

( * ) Notice: Subject to any disclaimer, the term of this patent is extended or adjusted under 35 U.S.C. 154(b) by 1030 days.

(21) Appl. No.: 17/706,968

(22) Filed: Mar. 29, 2022

(65) Prior Publication Data

US 2022/0218422 A1 Jul. 14, 2022

Related U.S. Application Data

(63) Continuation of application No. PCT/US2020/053803, filed on Oct. 1, 2020.

(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/20* (2016.02); *A61B 34/70* (2016.02); *A61B 90/06* (2016.02);
(Continued)

(58) Field of Classification Search
CPC .......................................... A61B 34/00–34/77
See application file for complete search history.

(56) References Cited

U.S. PATENT DOCUMENTS

| | | | |
|---|---|---|---|
| 7,725,162 B2 | 5/2010 | Malackowski et al. | |
| 7,831,292 B2 * | 11/2010 | Quaid .................... | A61B 34/37 |
| | | | 345/157 |

(Continued)

FOREIGN PATENT DOCUMENTS

| | | |
|---|---|---|
| CN | 105338920 A | 2/2016 |
| JP | 2008538184 A | 10/2008 |

(Continued)

OTHER PUBLICATIONS

English language abstract for CN 105338920 A extracted from espacenet.com database on Feb. 24, 2025, 2 pages.

(Continued)

*Primary Examiner* — Zade Coley
(74) *Attorney, Agent, or Firm* — Howard & Howard Attorneys PLLC

(57) ABSTRACT

A surgical system comprising a tool for engaging a target site, a manipulator configured to support the tool, and a sensing system configured to detect one or more system conditions associated with one or more of the tool, the manipulator, the target site, or combinations thereof. A controller is coupled to the manipulator and to the sensing system is configured to operate the manipulator between: a first mode to maintain alignment of the tool with respect to the target site according to a first constraint criteria, and a second mode to maintain alignment of the tool with respect to the target site according to a second constraint criteria different from the first constraint criteria. The controller changes operation of the manipulator from the first mode to the second mode in response to determining that at least one of the one or more system conditions satisfies a predetermined condition.

19 Claims, 39 Drawing Sheets

Related U.S. Application Data

(60) Provisional application No. 62/908,915, filed on Oct. 1, 2019.

(51) Int. Cl.
   *A61B 34/20*      (2016.01)
   *A61B 90/00*      (2016.01)

(52) U.S. Cl.
   CPC . *A61B 2034/2051* (2016.02); *A61B 2090/066* (2016.02)

(56)            References Cited

U.S. PATENT DOCUMENTS

| | | | |
|---|---|---|---|
| 8,010,180 | B2 | 8/2011 | Quaid et al. |
| 8,675,939 | B2 | 3/2014 | Moctezuma de la Barrera |
| 8,753,346 | B2 * | 6/2014 | Suarez .................... A61B 90/03 600/81 |
| 8,979,859 | B2 | 3/2015 | Eparmentier et al. |
| 9,008,757 | B2 * | 4/2015 | Wu ......................... A61B 34/30 600/407 |
| 9,119,655 | B2 | 9/2015 | Bowling et al. |
| 9,381,085 | B2 | 7/2016 | Axelson, Jr. et al. |
| 9,513,176 | B1 | 12/2016 | Weber et al. |
| 9,566,121 | B2 * | 2/2017 | Staunton .............. F16J 15/3256 |
| 9,566,122 | B2 | 2/2017 | Bowling et al. |
| 9,610,689 | B2 * | 4/2017 | Swarup .................. B25J 18/007 |
| 9,707,043 | B2 | 7/2017 | Bozung |
| 9,825,455 | B2 | 11/2017 | Sandhu et al. |
| 10,117,713 | B2 | 11/2018 | Moctezuma de la Barrera et al. |
| 10,327,849 | B2 | 6/2019 | Post |
| 2006/0142657 | A1 * | 6/2006 | Quaid .................... A61B 90/37 600/424 |
| 2007/0270685 | A1 * | 11/2007 | Kang ..................... A61B 90/03 600/424 |
| 2012/0059378 | A1 | 3/2012 | Farrell |
| 2012/0209314 | A1 * | 8/2012 | Weir ...................... A61B 90/06 606/205 |

| | | | |
|---|---|---|---|
| 2015/0094736 | A1 | 4/2015 | Malackowski et al. |
| 2015/0100066 | A1 | 4/2015 | Kostrzewski et al. |
| 2016/0228204 | A1 * | 8/2016 | Quaid .................... A61B 34/10 |
| 2016/0338782 | A1 * | 11/2016 | Bowling ........... A61B 17/1675 |
| 2018/0110572 | A1 * | 4/2018 | Flatt ................. A61B 17/32002 |
| 2018/0168750 | A1 * | 6/2018 | Staunton ................ A61B 34/20 |
| 2018/0333207 | A1 * | 11/2018 | Moctezuma De la Barrera ......... G06F 3/0484 |
| 2018/0353248 | A1 * | 12/2018 | Bowling ................ A61B 17/92 |
| 2019/0231446 | A1 * | 8/2019 | Bowling ................ A61B 34/10 |
| 2019/0231447 | A1 | 8/2019 | Ebbitt et al. |
| 2020/0078096 | A1 | 3/2020 | Barbagli et al. |
| 2020/0289133 | A1 | 9/2020 | Elbanna et al. |
| 2020/0323540 | A1 * | 10/2020 | Kang ..................... A61B 34/32 |
| 2021/0353373 | A1 | 11/2021 | Ye et al. |
| 2022/0079688 | A1 | 3/2022 | Kostrzewski et al. |

FOREIGN PATENT DOCUMENTS

| | | |
|---|---|---|
| WO | 2006091494 A1 | 8/2006 |
| WO | 2015193479 A1 | 12/2015 |
| WO | 2016187290 A1 | 11/2016 |

OTHER PUBLICATIONS

English language abstract for JP 2008-538184 A extracted from espacenet.com database on Aug. 21, 2024, 2 pages.

International Search Report for Application No. PCT/US2020/053803 dated Feb. 15, 2021, 3 pages.

Partial International Search Report for Application No. PCT/US2020/053803 dated Dec. 23, 2020, 2 pages.

Tamis, Marijn et al., "Constraint Based Physics Solver", Version 1.02, http://www.mft-spirit.nl/files/MTamis_ConstraintBasedPhysics-Solver.pdf, Jun. 15, 2015, 31 pages.

Tamis, Marijn, "Comparison Between Projected Gauss-Seidel and Sequential Impulse Solvers for Real-Time Physics Simulations," Version 1.01, http://www.mft-spirit.nl/files/MTamis_PGS_SI_Comparison.pdf, Jul. 1, 2015, 11 pages.

* cited by examiner

CEQ

Constraint Equation

- Calculate force for each constraint ($F_{p_i}$) in constraint space by solving system of n linear equations ($Ax = b \rightarrow x = A^{-1}b = F = (M^{-1})^{-1}a$)

$$F_p = \left( J_p M^{-1} J_p^T + \frac{C}{\Delta t} \right)^{-1} \left( \frac{v_{p_2}}{\Delta t} - \frac{J_p v_{cg_1}}{\Delta t} - \frac{\epsilon \Delta d}{\Delta t^2} - \left( J_p M^{-1} + \frac{C}{\Delta t} J_p^{-T} \right) \left( F_{inertial} + F_{damping} + F_{cg_{ext}} \right) \right) \geq 0$$

FIG. 8

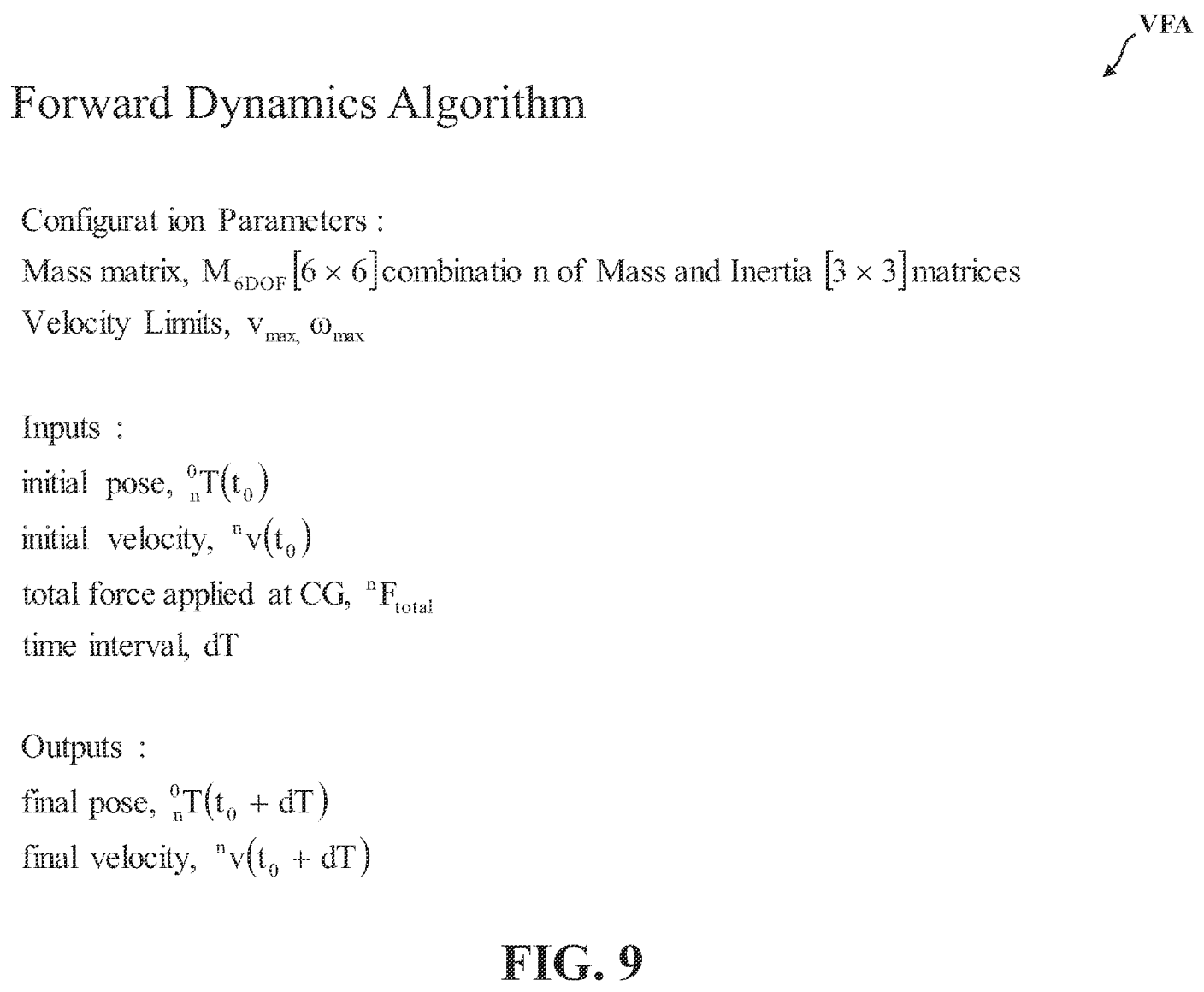

VFA

Forward Dynamics Algorithm

Configuration Parameters :

Mass matrix, $M_{6DOF}[6 \times 6]$ combinatio n of Mass and Inertia $[3 \times 3]$ matrices Velocity Limits, $v_{max}$, $\omega_{max}$ Inputs :

initial pose, $^0_nT(t_0)$ initial velocity, $^nv(t_0)$ total force applied at CG, $^nF_{total}$ time interval, dT Outputs :

final pose, $^0_nT(t_0 + dT)$ final velocity, $^nv(t_0 + dT)$

FIG. 9

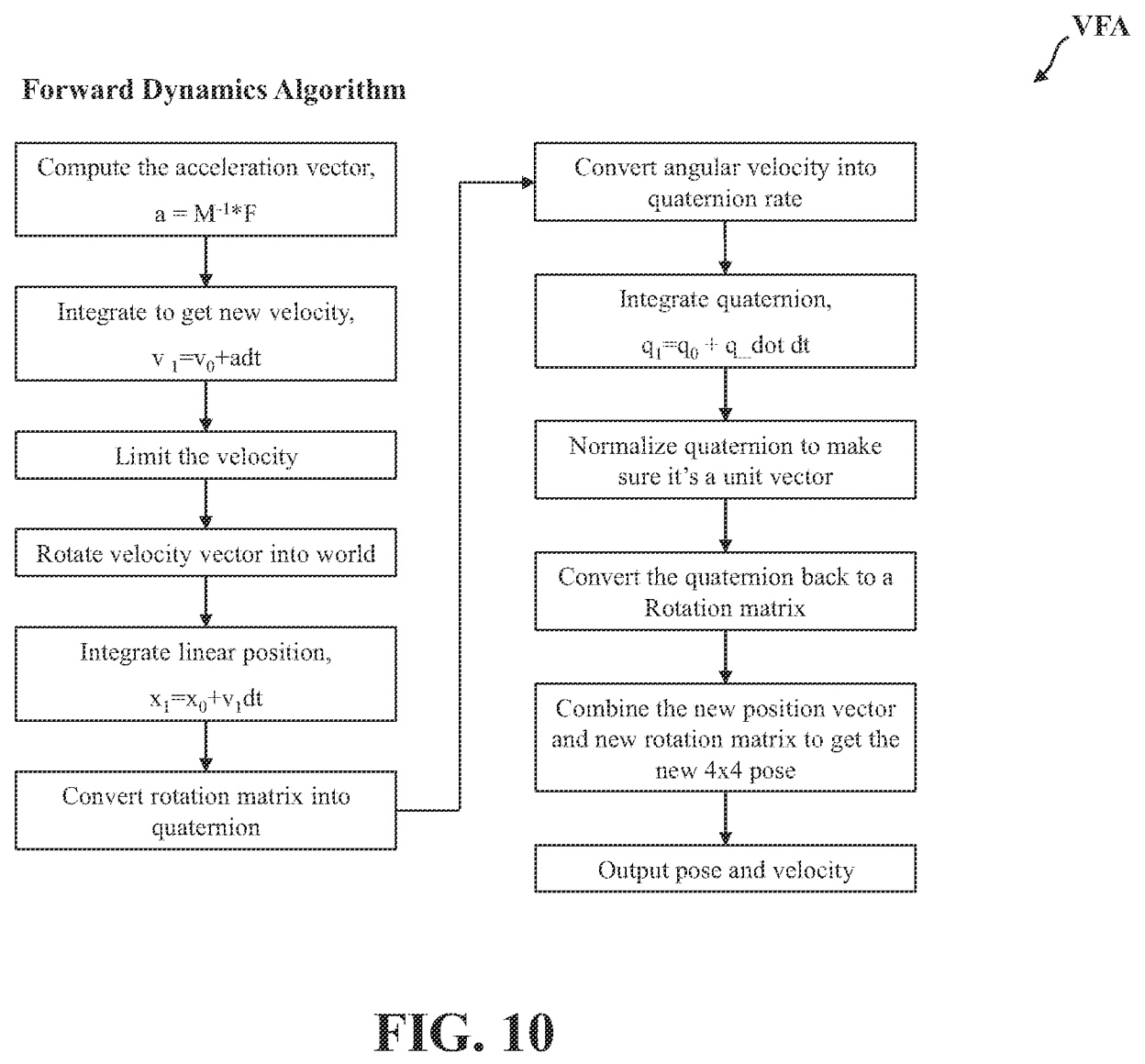

VFA

Forward Dynamics Algorithm

Compute the acceleration vector, $$a = M^{-1} * F$$

Integrate to get new velocity, $$v_1 = v_0 + a\,dt$$

Limit the velocity

Rotate velocity vector into world

Integrate linear position, $$x_1 = x_0 + v_1\,dt$$

Convert rotation matrix into quaternion

Convert angular velocity into quaternion rate

Integrate quaternion, $$q_1 = q_0 + \dot{q}\,dt$$

Normalize quaternion to make sure it's a unit vector

Convert the quaternion back to a Rotation matrix

Combine the new position vector and new rotation matrix to get the new 4x4 pose

Output pose and velocity

FIG. 10

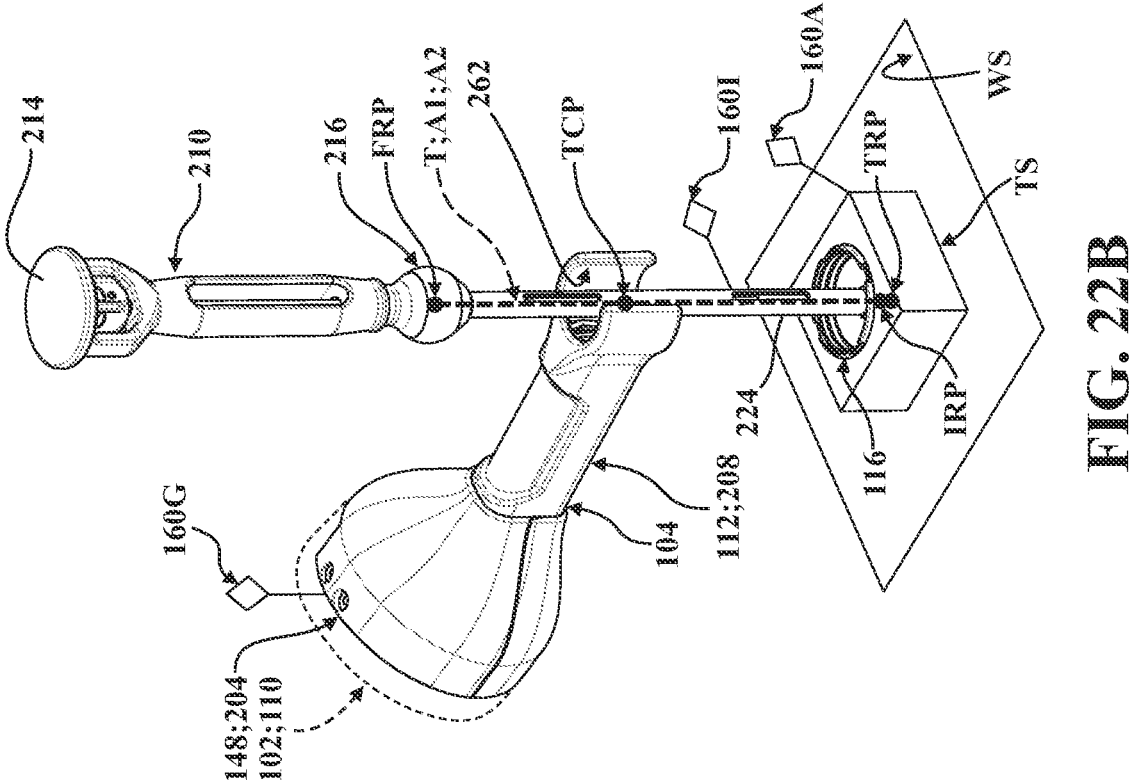
FIG. 22B

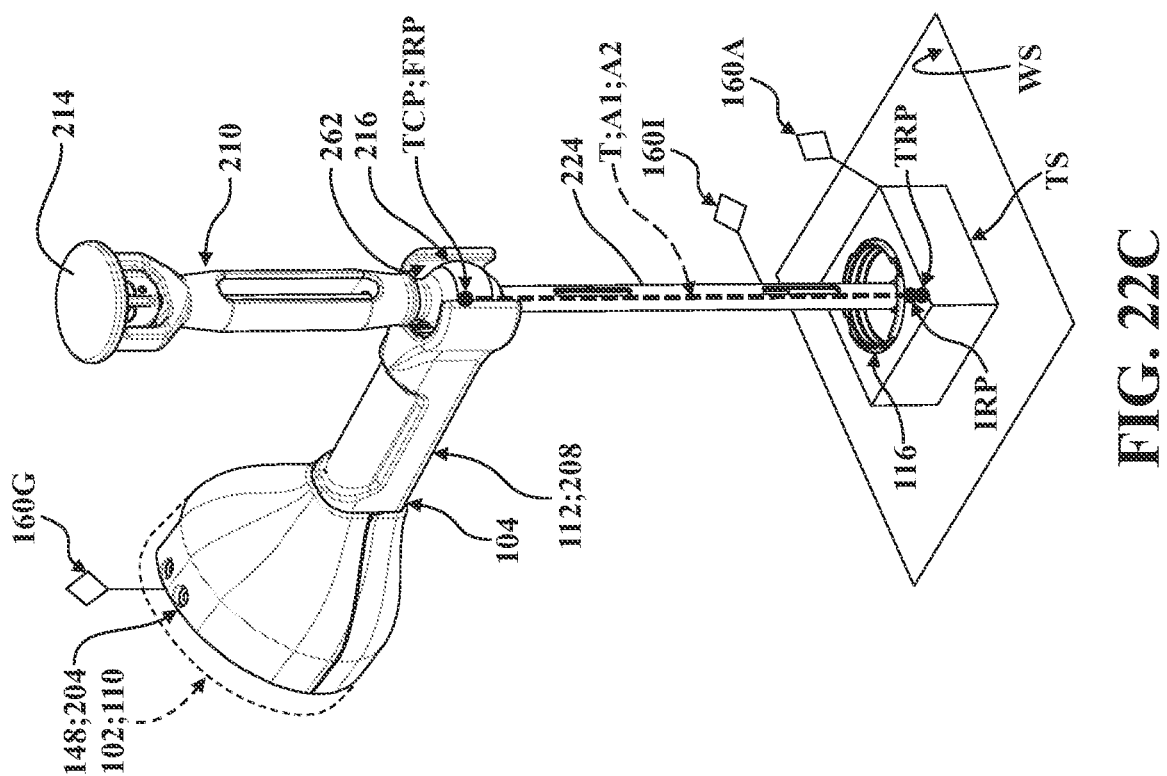
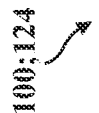
FIG. 22C

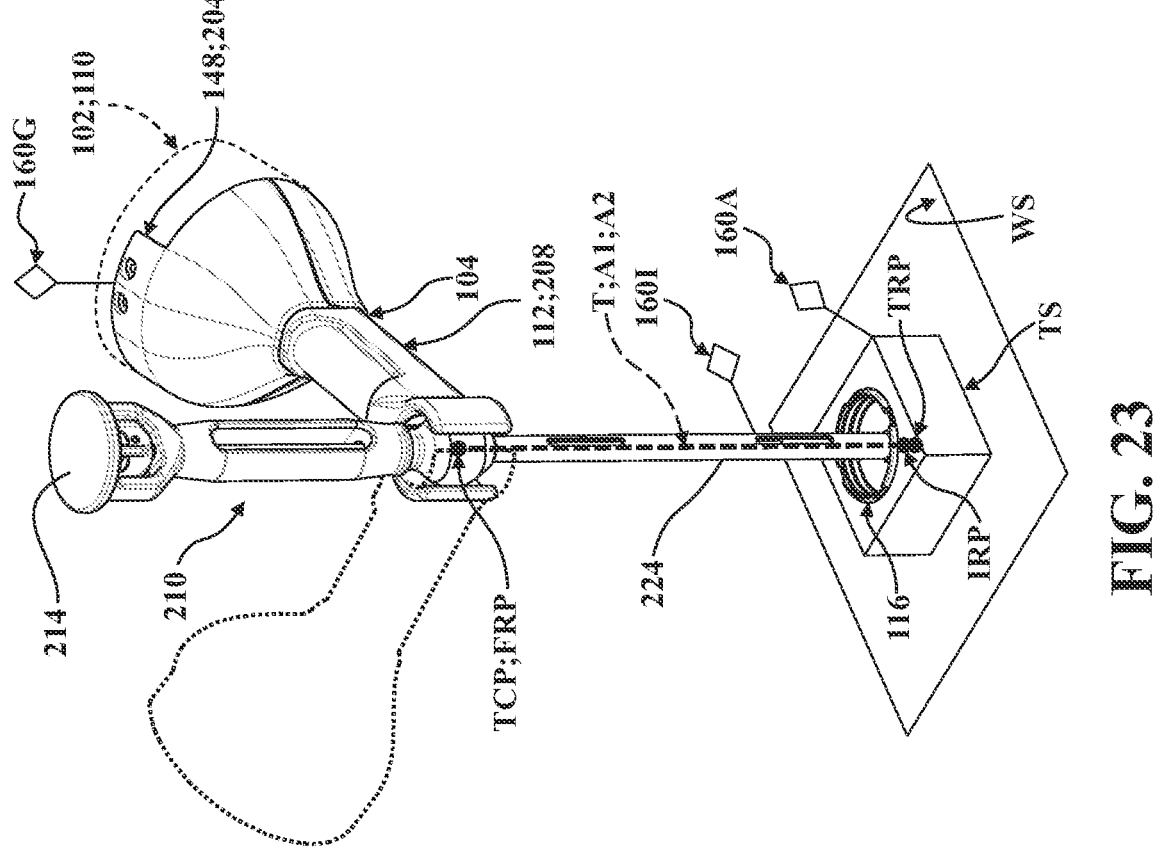
FIG. 23

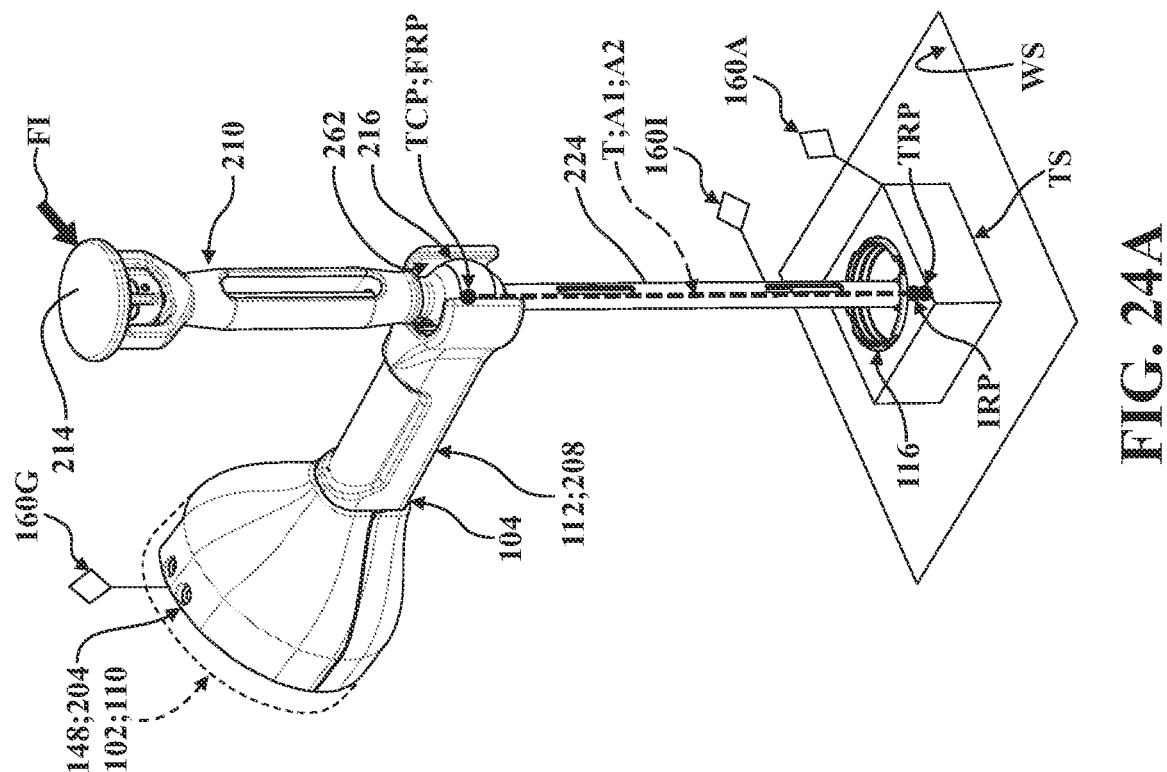
FIG. 24A

SURGICAL SYSTEMS AND METHODS FOR GUIDING ROBOTIC MANIPULATORS

CROSS-REFERENCE TO RELATED APPLICATIONS

The subject application is a Bypass Continuation of International Patent App. No. PCT/US2020/053803, filed Oct. 1, 2020, which claims priority to and all the benefits of U.S. Provisional Patent App. No. 62/908,915, filed Oct. 1, 2019, the contents of each of the aforementioned applications being hereby incorporated by reference in their entirety.

BACKGROUND

Robotic manipulators are frequently used to assist medical professionals in carrying out various conventional surgical procedures. To this end, a surgeon may use a surgical robot or another type of manipulator to guide, position, move, actuate, or otherwise manipulate various tools, components, prostheses, and the like during surgery.

Surgical robots can be used to assist surgeons in performing a number of different types of surgical procedures, and are commonly used in procedures involving the correction, resection, or replacement of degenerated joints to help improve patient mobility and reduce pain. By way of illustrative example, in hip replacement procedures, the surgeon replaces portions of the patient's hip joint with artificial prosthetic components. To this end, in total hip arthroplasty, the surgeon typically removes portions of the patient's femur to accommodate a prosthetic femoral component comprising a head, and resurfaces the acetabulum of the pelvis with a reamer to facilitate installing a prosthetic cup shaped to receive the head of the prosthetic femoral component.

Depending on the specific procedure being performed, the surgical robot may be used to help the surgeon approach the surgical site, remove portions of joints and/or bone, install prosthetic components, and the like. For example, in order to install the prosthetic cup into the acetabulum of the pelvis, the surgeon connects the cup to an impactor to implant the cup into the prepared acetabulum by striking the impactor to apply force (e.g., such as with a mallet). In order to facilitate installing the cup, the surgical robot helps keep the impactor aligned relative to the acetabulum, and the surgeon closely monitors the trajectory and depth of the cup during impaction to ensure proper alignment of the cup. Here, reaming or resecting the acetabulum generally defines the intended position of the cup which, in turn, defines the trajectory of impaction, which may be monitored via a tracker secured to the pelvis that is tracked via a navigation system.

Depending on the configuration of the prosthetic components, the impaction tools, and the surgical robot, maintaining a set trajectory can be difficult with certain approaches and surgical techniques, whereby misalignment of the cup or other prosthetic components frequently results from improper alignment and/or application of impact force. Furthermore, as the cup is being implanted into the reamed acetabulum, the patient's body effectively becomes physically-attached to the impactor and surgical robot in one or more degrees of freedom. Here, because the surgical robot typically restricts movement of the impactor relative to the trajectory based on the tracker secured to the pelvis, misalignment that may occur during impaction between the cup and the trajectory can sometimes lead to a "runaway" condition where the impactor and the pelvis are moved concurrently by the surgical robot attempting to bring the impactor tool back into alignment with the trajectory. Because of the physical connection between the surgical robot and the pelvis, this type of "runaway" condition may result in undesirable movement of the patient and/or unseating of an implanted or partially-implanted cup.

Similar "runaway" conditions may occur during other surgical procedures which employ different types of tools that are guided by surgical robots. By way of non-limiting example, a tool which comprises a powered surgical device may be used to drive an energy applicator configured to remove tissue at the surgical site. Here, under certain operating conditions, the energy applicator may engage tissue in such a way that effectively creates a lockup condition between the energy applicator to the tissue. For example, a rotary instrument driving a drill bit, or a bur could become misaligned and lodged in bone while forming a pilot hole in a pedicle of a vertebra in the spine. Here too, a "runaway" condition may result in undesirable movement of the patient and/or energy applicator engaged against tissue such as bone.

Accordingly, there remains a need in the art for addressing one or more of these deficiencies.

SUMMARY

This Summary introduces a selection of concepts in a simplified form that are further described below in the Detailed Description below. This Summary is not intended to limit the scope of the claimed subject matter and does not necessarily identify each and every key or essential feature of the claimed subject matter.

According to a first aspect, a surgical system is provided comprising: a tool for engaging a target site; a manipulator configured to support the tool; a sensing system configured to detect one or more system conditions associated with one or more of the tool, the manipulator, the target site, or combinations thereof; and a controller coupled to the manipulator and to the sensing system, the controller being configured to operate the manipulator between: a first mode to maintain alignment of the tool with respect to the target site according to a first constraint criteria, and a second mode to maintain alignment of the tool with respect to the target site according to a second constraint criteria different from the first constraint criteria; and wherein the controller is further configured to change operation of the manipulator from the first mode to the second mode in response to determining that at least one of the one or more system conditions satisfies a predetermined condition.

According to a second aspect, a method of operating the surgical system of the first aspect is provided.

According to a third aspect, a surgical system is provided comprising: a tool for engaging a target site along a trajectory; a manipulator configured to support the tool; at least one sensor configured to obtain measurements indicative of a force occurring between the target site and the manipulator; and a controller coupled to the manipulator and to the at least one sensor, the controller being configured to operate the manipulator between: a first mode to maintain alignment of the tool with respect to the trajectory according to a first constraint criteria, and a second mode to maintain alignment of the tool with respect to the trajectory according to a second constraint criteria different from the first constraint criteria; and wherein the controller is further configured to change operation of the manipulator from the first mode to the second mode in response to determining that the force satisfies a predetermined condition.

According to a fourth aspect, a method of operating the surgical system of the third aspect is provided.

According to a fifth aspect, a surgical system is provided comprising: a tool for engaging a target site; a manipulator configured to support the tool relative to the target site; a patient tracker adapted for attachment relative to the target site; a navigation system configured to track states of the patient tracker; and a controller coupled to the manipulator and to the navigation system, the controller being configured to operate the manipulator between: a first mode to maintain alignment of the tool with respect to the target site according to a first constraint criteria, and a second mode to maintain alignment of the tool with respect to the target site according to a second constraint criteria different from the first constraint criteria; wherein the controller is further configured to compare tracked movement of the tool against movement of the patient tracker based on tracked states received from the navigation system; and wherein the controller is further configured to change operation of the manipulator from the first mode to the second mode in response to determining that tracked movement of the tool corresponds to movement of the patient tracker.

According to a sixth aspect, a method of operating the surgical system of the fifth aspect is provided.

According to a seventh aspect, a method of operating a surgical system is provided comprising an impactor assembly having an interface for releasably securing a prosthesis, a guide having a channel formed to receive the impactor assembly, a manipulator configured to support the guide relative to a target site along a trajectory, at least one sensor, and a controller coupled to the manipulator and to the at least one sensor and being configured to perform the steps of: operating the manipulator in a first mode to maintain alignment of the guide with respect to the trajectory according to a first constraint criteria; operating the manipulator in a second mode to maintain alignment of the guide with respect to the trajectory according to a second constraint criteria different from the first constraint criteria; detecting a force occurring between the target site and the manipulator based on measurements from the at least one sensor; and determining that the force satisfies a predetermined condition and changing operation of the manipulator from the first mode to the second mode in response According to a seventh aspect, a surgical system is provided comprising: a tool for engaging a target site; a manipulator configured to support the tool; a sensing system configured to detect one or more system conditions associated with one or more of the tool, the manipulator, the target site, or combinations thereof; and a controller coupled to the manipulator and to the sensing system, the controller being configured to: operate the manipulator to maintain alignment of the tool with respect to the target site according to a first constraint criteria; and in response to detecting the one or more system conditions, operate the manipulator to maintain alignment of the tool with respect to the target site according to a second constraint criteria that is different from the first constraint criteria.

According to an eighth aspect, a method of operating the surgical system of the seventh aspect is provided.

According to a ninth aspect, a surgical system is provided comprising: a tool for engaging a target site along a trajectory; a manipulator configured to support the tool; at least one sensor configured to obtain measurements indicative of a force occurring between the target site and the manipulator; and a controller coupled to the manipulator and to the at least one sensor, the controller being configured to: operate the manipulator to maintain alignment of the tool with respect to the trajectory according to a first constraint criteria; evaluate the obtained measurements indicative of the force; and in response to the evaluation, operate the manipulator to maintain alignment of the tool with respect to the trajectory according to a second constraint criteria that is different from the first constraint criteria.

According to a tenth aspect, a method of operating the surgical system of the ninth aspect is provided.

According to an eleventh aspect, a surgical system is provided comprising: a tool for engaging a target site; a manipulator configured to support the tool relative to the target site; a patient tracker adapted for attachment relative to the target site; a navigation system configured to track states of the patient tracker; and a controller coupled to the manipulator and to the navigation system, the controller being configured to: operate the manipulator to maintain alignment of the tool with respect to the target site according to a first constraint criteria; evaluate tracked movement of the tool relative to movement of the patient tracker based on tracked states of the patient tracker received from the navigation system; and in response to the evaluation, operate the manipulator to maintain alignment of the tool with respect to the target site according to a second constraint criteria that is different from the first constraint criteria.

According to a twelfth aspect, a method of operating the surgical system of the eleventh aspect is provided.

According to an thirteenth aspect, a surgical system is provided comprising: a tool for engaging a target site; a manipulator configured to support the tool relative to the target site; a patient tracker adapted for attachment relative to the target site; a navigation system configured to track states of the patient tracker; and a controller coupled to the manipulator and to the navigation system, the controller being configured to: operate the manipulator to constrain movement of the tool with respect to a virtual boundary associated with the target site according to a first constraint criteria; evaluate tracked movement of the tool relative to movement of the patient tracker based on tracked states of the patient tracker received from the navigation system; and in response to the comparison, operate the manipulator to constrain movement of the tool with respect to the virtual boundary according to a second constraint criteria different from the first constraint criteria.

According to a fourteenth aspect, a method of operating the surgical system of the thirteenth aspect is provided.

Any of the aspects above can be combined in part, or in whole. Furthermore, any of the aspects above can be implemented with any of the following implementations:

In one implementation, the first constraint criteria comprises a first number of degrees of freedom in which movement of the tool is restricted relative to the target site. In one implementation, the second constraint criteria comprises a second number of degrees of freedom in which movement of the tool is restricted relative to the target site. In one implementation, the second number of degrees of freedom being different from the first number of degrees of freedom. In one implementation, the controller is further configured to operate the manipulator: in the first mode to maintain alignment of the tool with respect to the target site based on the first number of degrees of freedom; and in the second mode to maintain alignment of the tool with respect to the target site based on the second number of degrees of freedom.

In one implementation, the second number of degrees of freedom is smaller than the first number of degrees of freedom such that the controller permits movement of the tool relative to the target site in at least one more degree of freedom in the second mode than in the first mode. In one implementation, the first constraint criteria comprises at least one positional degree of freedom and at least one orientational degree of freedom. In one implementation, the first constraint criteria and the second constraint criteria each comprise at least one orientational degree of freedom. In one implementation, the first constraint criteria comprises at least one more positional degree of freedom than the second constraint criteria. In one implementation, the first constraint criteria and the second constraint criteria comprise at least one common degree of freedom.

In one implementation, the first constraint criteria comprises a first resilience parameter, and the second constraint criteria comprise a second resilience parameter different from the first resilience parameter. In one implementation, the controller is further configured to operate the manipulator: in the first mode to maintain alignment of the tool with respect to the target site based on the first resilience parameter; and in the second mode to maintain alignment of the tool with respect to the target site based on the second resilience parameter. In one implementation, the controller permits more resilient movement of the tool relative to the target site in the second mode than in the first mode. In one implementation, the first resilience parameter and the second resilience parameter are each associated with resilient movement of the tool relative to the target site in a common degree of freedom.

In one implementation, the tool defines a tool center point. In one implementation, the controller is configured to operate the manipulator in the first mode to restrict movement of the tool center point away from the target site according to the first constraint criteria.

In one implementation, the controller is configured to operate the manipulator in the second mode to permit movement of the tool center point away from the target site according to the second constraint criteria.

In one implementation, a mode indicator is coupled to the controller. In one implementation, the controller is configured to activate the mode indicator in response to determining that at least one of the one or more system conditions satisfies the predetermined condition to communicate to a user the change in operation of the manipulator from the first mode to the second mode.

In one implementation, the controller is configured to operate the manipulator in the first mode to permit movement of the tool relative to the target site in at least one degree of freedom according to the first constraint criteria.

In one implementation, the controller is configured to operate the manipulator in the second mode to permit movement of the tool relative to the target site in at least one degree of freedom according to the second constraint criteria.

In one implementation, the controller is further configured to operate the manipulator in a third mode to maintain alignment of the tool with respect to the target site according to a third constraint criteria different from both the first constraint criteria and the second constraint criteria. In one implementation, the predetermined condition is further defined as a first predetermined condition. In one implementation, the controller is further configured to change operation of the manipulator from the second mode to the third mode in response to determining that at least one of the one or more system conditions satisfies a second predetermined condition different from the first predetermined condition.

In one implementation, the first constraint criteria comprises a first number of degrees of freedom in which movement of the tool is restricted relative to the target site.

In one implementation, the second constraint criteria comprises a second number of degrees of freedom in which movement of the tool is restricted relative to the target site. In one implementation, the third constraint criteria comprises a third number of degrees of freedom in which movement of the tool is restricted relative to the target site. In one implementation, the third number of degrees of freedom is different from one or more of the first number of degrees of freedom and the second number of degrees of freedom; and wherein the controller is further configured to operate the manipulator: in the first mode to maintain alignment of the tool with respect to the target site based on the first number of degrees of freedom; in the second mode to maintain alignment of the tool with respect to the target site based on the second number of degrees of freedom; and in the third mode to maintain alignment of the tool with respect to the target site based on the third number of degrees of freedom.

In one implementation, the first constraint criteria further comprises a first resilience parameter. In one implementation, the second constraint criteria further comprises a second resilience parameter. In one implementation, the third constraint criteria further comprises a third resilience parameter different from one or more of the first resilient parameter and the second resilience parameter. In one implementation, the controller is further configured to operate the manipulator: in the first mode to maintain alignment of the tool with respect to the target site based on the first number of degrees of freedom and also based on the first resilience parameter; in the second mode to maintain alignment of the tool with respect to the target site based on the second number of degrees of freedom and also based on the second resilience parameter; and in the third mode to maintain alignment of the tool with respect to the target site based on the third number of degrees of freedom and also based on the third resilience parameter.

In one implementation, the third number of degrees of freedom is smaller than the first number of degrees of freedom such that the controller permits movement of the tool relative to the target site in at least one more degree of freedom in the third mode than in the first mode. In one implementation, the third number of degrees of freedom is smaller than the second number of degrees of freedom such that the controller permits movement of the tool relative to the target site in at least one more degree of freedom in the third mode than in the second mode. In one implementation, the first constraint criteria and the second constraint criteria each comprise at least one positional degree of freedom and at least one orientational degree of freedom. In one implementation, the first constraint criteria, the second constraint criteria, and the third constraint criteria each comprise at least one orientational degree of freedom. In one implementation, the first constraint criteria comprises at least one more positional degree of freedom than the third constraint criteria. In one implementation, the second constraint criteria comprises at least one more positional degree of freedom than the third constraint criteria. In one implementation, the controller permits more resilient movement of the tool relative to the target site in the second mode than in the first mode. In one implementation, the controller permits more resilient movement of the tool relative to the target site in the second mode than in the third mode.

In one implementation, the first constraint criteria comprises a first resilience parameter, the second constraint criteria comprises a second resilience parameter, and the third constraint criteria comprises a third resilience parameter different from one or more of the first resilient parameter and the second resilience parameter; and wherein the controller is further configured to operate the manipulator: in the first mode to maintain alignment of the tool with respect to the target site based on the first resilience parameter; in the second mode to maintain alignment of the tool with respect to the target site based on the second resilience parameter; and in the third mode to maintain alignment of the tool with respect to the target site based on the third resilience parameter.

In one implementation, the sensing system comprises at least one sensor configured to obtain measurements indicative of a force occurring between the target site and the manipulator; and wherein the measurements indicative of the force obtained by the at least one sensor define at least one of the one or more system conditions such that the controller is configured to change operation of the manipulator: from the first mode to the second mode in response to determining that the force detected by the at least one sensor satisfies the first predetermined condition, and from the second mode to the third mode in response to determining that the force detected by the at least one sensor satisfies the second predetermined condition. In one implementation the first predetermined condition is defined by a first force detected by the at least one sensor, the second predetermined condition is defined by a second force detected by the at least one sensor, and the second force is larger than the first force In one implementation, a patient tracker is adapted for attachment relative to the target site. In one implementation, the sensing system comprises a navigation system configured to track states of the patient tracker. In one implementation, tracked states of the patient tracker define at least one of the one or more system conditions such that the controller is configured to change operation of the manipulator from the first mode to the second mode in response to determining that tracked states of the patient tracker satisfy the predetermined condition. In one implementation, the controller is further configured to compare tracked movement of the tool against movement of the patient tracker based on tracked states received from the navigation system. In one implementation, tracked movement of the tool defines at least one of the one or more system conditions. In one implementation, the predetermined condition is defined based on tracked movement of the tool corresponding to tracked states of the patient tracker.

In one implementation, the sensing system comprises at least one sensor configured to obtain measurements indicative of a force occurring between the target site and the manipulator. In one implementation, measurements indicative of the force obtained by the at least one sensor define at least one of the one or more system conditions such that the controller is configured to change operation of the manipulator from the first mode to the second mode in response to determining that the force detected by the at least one sensor satisfies the predetermined condition.

In one implementation, the controller is further configured to operate the manipulator in the first mode to resist movement of the tool relative to the target site with increasing resilience as the measurements indicative of the force obtained by the at least one sensor increases toward the predetermined condition. In one implementation, the tool comprises a guide with a channel formed to receive an impactor assembly and permit limited movement of the impactor assembly relative to the guide, the impactor assembly having an interface for releasably securing a prosthesis. In one implementation, the manipulator is configured to support the guide along a trajectory relative to the target site while the impactor assembly is received in the channel of the guide and while the prosthesis is secured to the impactor assembly. In one implementation, the target site is further defined as an acetabular cup. In one implementation, the at least one sensor is configured to detect the force occurring as a result of a force applied on the impactor assembly to install the prosthesis in the acetabular cup. In one implementation, the controller is further configured to deduce a torque being applied to the acetabular cup based on the detected force. In one implementation, the controller is further configured to change operation of the manipulator from the first mode to the second mode in response to determining that the deduced torque applied to the acetabular cup satisfies the predetermined condition.

In one implementation, the at least sensor is further defined as one or more of a: force torque transducer; joint actuator current sensor; joint force sensor; joint torque sensor; and joint encoder In one implementation, the first constraint criteria comprises a first number of degrees of freedom in which movement of the tool is restricted relative to the trajectory. In one implementation, the second constraint criteria comprises a second number of degrees of freedom in which movement of the tool is restricted relative to the trajectory. In one implementation, the second number of degrees of freedom being different from the first number of degrees of freedom. In one implementation, the controller is further configured to operate the manipulator: in the first mode to maintain alignment of the tool with respect to the trajectory based on the first number of degrees of freedom; and in the second mode to maintain alignment of the tool with respect to the trajectory based on the second number of degrees of freedom.

In one implementation, the second number of degrees of freedom is smaller than the first number of degrees of freedom such that the controller permits movement of the tool relative to the trajectory in at least one more degree of freedom in the second mode than in the first mode. In one implementation, the first constraint criteria comprises at least one positional degree of freedom and at least one orientational degree of freedom. In one implementation, the first constraint criteria and the second constraint criteria each comprise at least one orientational degree of freedom. In one implementation, the first constraint criteria comprises at least one more positional degree of freedom than the second constraint criteria. In one implementation, the first constraint criteria and the second constraint criteria comprise at least one common degree of freedom.

In one implementation, the first constraint criteria comprises a first resilience parameter, and the second constraint criteria comprise a second resilience parameter different from the first resilience parameter. In one implementation, the controller is further configured to operate the manipulator: in the first mode to maintain alignment of the tool with respect to the trajectory based on the first resilience parameter; and in the second mode to maintain alignment of the tool with respect to the trajectory based on the second resilience parameter.

In one implementation, the controller permits more resilient movement of the tool relative to the trajectory in the second mode than in the first mode. In one implementation, the first resilience parameter and the second resilience parameter are each associated with resilient movement of the tool relative to the trajectory in a common degree of freedom.

In one implementation, the controller is further configured to operate the manipulator in the first mode to resist movement of the tool relative to the trajectory with increasing resilience as the measurements indicative of the force obtained by the at least sensor increases toward the predetermined condition.

In one implementation, the tool defines a tool center point and the controller is configured to operate the manipulator in the first mode to restrict movement of the tool center point away from the trajectory according to the first constraint criteria. In one implementation, the controller is configured to operate the manipulator in the second mode to permit movement of the tool center point away from the trajectory according to the second constraint criteria.

In one implementation, a mode indicator is coupled to the controller and the controller is configured to activate the mode indicator in response to determining that the measurements indicative of the force obtained by the at least sensor satisfies the predetermined condition to communicate to a user the change in operation of the manipulator from the first mode to the second mode.

In one implementation, the controller is configured to operate the manipulator in the first mode to permit movement of the tool relative to the trajectory in at least one degree of freedom according to the first constraint criteria.

In one implementation, the controller is configured to operate the manipulator in the second mode to permit movement of the tool relative to the trajectory in at least one degree of freedom according to the second constraint criteria.

In one implementation, the controller is further configured to operate the manipulator in a third mode to maintain alignment of the tool with respect to the trajectory according to a third constraint criteria different from both the first constraint criteria and the second constraint criteria. In one implementation, the predetermined condition is further defined as a first predetermined condition. In one implementation, the controller is further configured to change operation of the manipulator from the second mode to the third mode in response to determining that measurements indicative of force obtained by the at least one sensor satisfies a second predetermined condition different from the first predetermined condition. In one implementation, the first predetermined condition is defined by a first force detected by measurements obtained from the at least one sensor, the second predetermined condition is defined by a second force detected by measurements obtained from the at least one sensor, and the second force is larger than the first force. In one implementation, the first constraint criteria comprises a first number of degrees of freedom in which movement of the tool is restricted relative to the trajectory, the second constraint criteria comprises a second number of degrees of freedom in which movement of the tool is restricted relative to the trajectory, and the third constraint criteria comprises a third number of degrees of freedom in which movement of the tool is restricted relative to the trajectory, the third number of degrees of freedom being different from one or more of the first number of degrees of freedom and the second number of degrees of freedom; and wherein the controller is further configured to operate the manipulator: in the first mode to maintain alignment of the tool with respect to the trajectory based on the first number of degrees of freedom; in the second mode to maintain alignment of the tool with respect to the trajectory based on the second number of degrees of freedom; and in the third mode to maintain alignment of the tool with respect to the trajectory based on the third number of degrees of freedom.

In one implementation, the first constraint criteria further comprises a first resilience parameter, the second constraint criteria further comprises a second resilience parameter, and the third constraint criteria further comprises a third resilience parameter different from one or more of the first resilient parameter and the second resilience parameter; and wherein the controller is further configured to operate the manipulator: in the first mode to maintain alignment of the tool with respect to the trajectory based on the first number of degrees of freedom and also based on the first resilience parameter; in the second mode to maintain alignment of the tool with respect to the trajectory based on the second number of degrees of freedom and also based on the second resilience parameter; and in the third mode to maintain alignment of the tool with respect to the trajectory based on the third number of degrees of freedom and also based on the third resilience parameter.

In one implementation, the third number of degrees of freedom is smaller than the first number of degrees of freedom such that the controller permits movement of the tool relative to the trajectory in at least one more degree of freedom in the third mode than in the first mode. In one implementation, the third number of degrees of freedom is smaller than the second number of degrees of freedom such that the controller permits movement of the tool relative to the trajectory in at least one more degree of freedom in the third mode than in the second mode.

In one implementation, the first constraint criteria and the second constraint criteria each comprise at least one positional degree of freedom and at least one orientational degree of freedom. In one implementation, the first constraint criteria, the second constraint criteria, and the third constraint criteria each comprise at least one orientational degree of freedom. In one implementation, the first constraint criteria comprises at least one more positional degree of freedom than the third constraint criteria. In one implementation, the second constraint criteria comprises at least one more positional degree of freedom than the third constraint criteria. In one implementation, the controller permits more resilient movement of the tool relative to the trajectory in the second mode than in the first mode. In one implementation, the controller permits more resilient movement of the tool relative to the trajectory in the second mode than in the third mode.

In one implementation, the first constraint criteria comprises a first resilience parameter, the second constraint criteria comprises a second resilience parameter, and the third constraint criteria comprises a third resilience parameter different from one or more of the first resilient parameter and the second resilience parameter. In one implementation, the controller is further configured to operate the manipulator: in the first mode to maintain alignment of the tool with respect to the trajectory based on the first resilience parameter; in the second mode to maintain alignment of the tool with respect to the trajectory based on the second resilience parameter; and in the third mode to maintain alignment of the tool with respect to the trajectory based on the third resilience parameter.

In one implementation, a patient tracker is adapted for attachment relative to the target site and a navigation system configured to track states of the patient tracker; and wherein the controller is coupled to the navigation system and is further configured to define the trajectory based on the tracked states of the patient tracker received from the navigation system.

In one implementation, the tool comprises a guide with a channel formed to receive an impactor assembly and permit limited movement of the impactor assembly relative to the guide, the impactor assembly having an interface for releasably securing a prosthesis. In one implementation, the manipulator is configured to support the guide relative to the target site.

In one implementation, the manipulator is configured to support the guide relative to the target site while the impactor assembly is received in the channel of the guide and while the prosthesis is secured to the impactor assembly and wherein the target site is further defined as an acetabular cup. In one implementation, the at least one sensor is configured to obtain measurements indicative of the force occurring as a result of a force applied on the impactor assembly to install the prosthesis in the acetabular cup. In one implementation, the controller is further configured to deduce a torque being applied to the acetabular cup based on the detected force. In one implementation, the controller is further configured to change operation of the manipulator from the first mode to the second mode in response to determining that the deduced torque applied to the acetabular cup satisfies the predetermined condition.

In one implementation, the controller is configured to determine parameters of the second constraint criteria based on the detected system condition from the sensing system.

In one implementation, the controller is configured to determine parameters of the second constraint criteria based on the obtained measurements indicative of the force.

In one implementation, the controller is configured to determine parameters of the second constraint criteria based on the evaluated tracked movement.

Any of the above implementations can be utilized for any of the aspects described above. Any of the above implementations can be combined in whole, or in part, for any one or more aspects described above.

Other features and advantages of the present disclosure will be readily appreciated, as the same becomes better understood, after reading the subsequent description taken in conjunction with the accompanying drawings.

BRIEF DESCRIPTION OF THE DRAWINGS

FIG. 8 depicts a sample constraint equation of the control system of FIG. 2.

FIG. 9 depicts a sample forward dynamics algorithm for carrying out a virtual simulation with the control system of FIG. 2.

FIG. 10 depicts an exemplary set of steps for implementing the forward dynamics algorithm of FIG. 9.

FIG. 22B is another partial perspective view of the guide, the impactor assembly supporting the prosthesis, and the target site of FIG. 22A, shown with the guide coupled to the manipulator having moved toward the trajectory with the shaft of the impactor assembly arranged within the channel of the guide.

FIG. 22C is another partial perspective view of the guide, the impactor assembly supporting the prosthesis, and the target site of FIG. 22B, shown with the guide coupled to the manipulator having moved along the trajectory to bring the flange of the impactor assembly into engagement with the channel of the guide.

FIG. 23 is another partial perspective view of the guide, the impactor assembly supporting the prosthesis, and the target site of FIG. 22C, shown with the guide coupled to the manipulator having moved about the trajectory in one rotational degree of freedom from a previous arrangement depicted in phantom.

FIG. 24A is another partial perspective view of the guide, the impactor assembly supporting the prosthesis, and the target site of FIG. 22B, shown with the guide coupled to the manipulator arranged along the trajectory with the flange of the impactor assembly disposed in engagement with the channel of the guide, and with an applied force acting on the head of the impactor assembly transverse to the trajectory.

FIG. 26 illustrates a runaway condition occurring as a result of a bur being trapped between a virtual boundary and a target site bone.

Any one or more of the embodiments depicted throughout the drawings may have certain components, structural features, and/or assemblies removed, depicted schematically, and/or shown in phantom for illustrative purposes.

DETAILED DESCRIPTION

Figure 1:
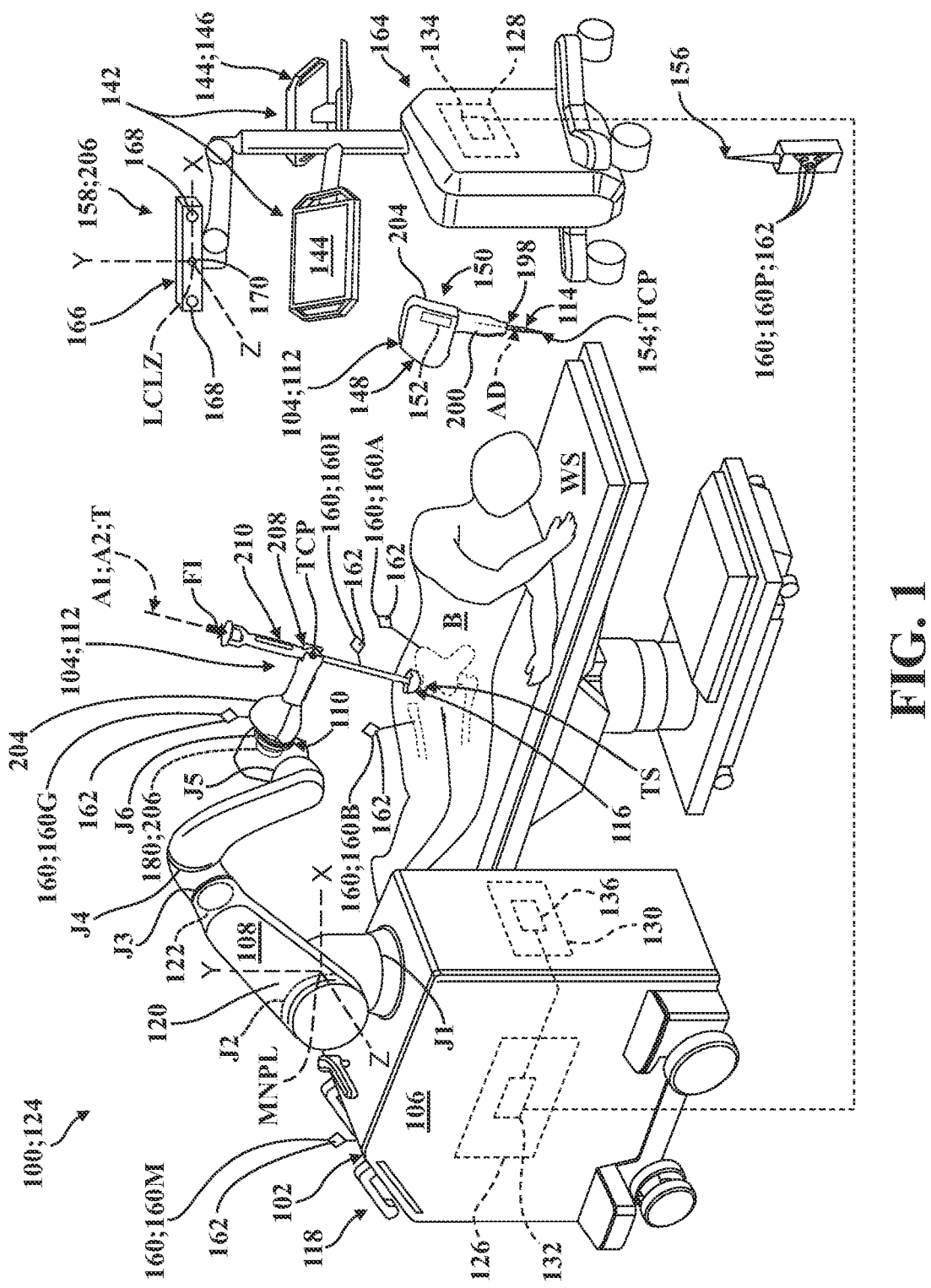
FIG. 1 is a perspective view of a surgical system comprising a manipulator, a navigation system, and tools for engaging a target site, with one of the tools shown having a powered surgical device for driving an energy applicator, and with another of the tools shown having an impactor assembly coupled to a prosthesis and supported along a trajectory by a guide attached to the manipulator.

Referring now to FIG. 1, a surgical system 100 comprising a robotic manipulator 102 supporting a tool 104 is shown. The surgical system 100 is useful for treating an anatomical volume or target site TS of a patient's P body B, such as bone or soft tissue. To this end, the manipulator 102 generally comprises a base 106, a robotic arm 108, and a coupling 110. The robotic arm 108 is supported by the base 106 and is configured to move, maintain, or otherwise control the position and/or orientation of the coupling 110 relative to the base 106 during use. The coupling 110 is adapted to releasably secure one or more types of tools 104 which, in turn, generally support or otherwise include an instrument 112 utilized in connection with various types of surgical procedures. In some embodiments, the instrument 112 may be configured to support, drive, rotate, oscillate, vibrate, and/or otherwise direct energy to an energy applicator 114 (e.g., drill bits, taps, burs, blades, saws, reamers, and the like) used to effect treatment at or adjacent to the target site TS. In some embodiments, the instrument 112 may be configured to support, position, align, and/or guide implantable components 116 (e.g., cups, stems, screws, pins, rods, wires, anchors, prostheses, and the like) at or with respect to the target site TS, such as along a trajectory T maintained by the manipulator 102.

In FIG. 1, the patient P is undergoing an illustrative surgical procedure where the target site TS includes or is otherwise defined by portions of the patient's hip and femur. However, that various types of surgical procedures are contemplated by the present disclosure, including without limitation surgical procedures involving partial or total knee or hip replacement surgery, shoulder replacement surgery, spine surgery, ankle surgery, and the like. The surgical procedure may involve tissue removal or other forms of treatment (e.g., cutting, drilling, reaming, coagulating, lesioning, other in-situ tissue treatments, and the like). In some embodiments, the surgical system 100 may be designed to facilitate cutting away material to be replaced by implantable components 116 (also referred to as "implants"), such as hip and knee implants, including unicompartmental, bicompartmental, multicompartmental, or total knee implants. Some types of implantable components 116 are shown in U.S. Pat. No. 9,381,085, entitled "Prosthetic Implant and Method of Implantation," the disclosure of which is hereby incorporated by reference in its entirety. However, and as will be appreciated from the subsequent description below, other configurations are contemplated, and the surgical system 100 could be utilized in connection with a number of different surgical procedures and may employ various types, styles, and configurations of manipulators 102, tools 104, instruments 112, energy applicators 114, and/or implantable components 116 without departing from the scope of the present disclosure. Furthermore, the surgical system 100 and techniques disclosed herein may be used to perform other procedures, surgical or non-surgical, or may be used in industrial applications or other applications where robotic systems are utilized.

The manipulator 102 (also referred to as a "surgical robot") moves the tool 104 relative to the target site TS and relative to the base 106 via the robotic arm 108 to, among other things, assist medical professionals in carrying out various types of surgical procedures with precise control over movement and positioning of the tool 104, the instrument 112, the energy applicator 114, and/or the implantable component 116. As noted above, the manipulator 102 generally comprises the base 106, the robotic arm 108, and the coupling 110. The base 106 is fixed to a manipulator cart 118 and supports the robotic arm 108 which, in turn, is configured to move, maintain, or otherwise control the position and/or orientation of the coupling 110 relative to the base 106 during use. To this end, the robotic arm 108 illustrated in FIG. 1 comprises a plurality of links 120 and joints J arranged in a serial arm configuration. However, the manipulator 102 could employ a different configuration without departing from the scope of the present disclosure. By way of non-limiting example, the manipulator 102 may have a parallel arm configuration, or any other suitable configuration. In some embodiments, more than one manipulator 102 may be utilized in a multiple arm configuration. One exemplary arrangement of the robotic arm 108 is described in U.S. Pat. No. 9,119,655, entitled "Surgical Manipulator Capable of Controlling a Surgical Instrument in Multiple Modes," the disclosure of which is hereby incorporated by reference in its entirety. The robotic arm 108 and other portions of the manipulator 102 may be arranged in a number of different configurations without departing from the scope of the present disclosure.

In the example shown in FIG. 1, the manipulator 102 comprises a plurality of joint encoders 122 located at the joints J for determining position data of the joints J. For simplicity, only one joint encoder 122 is labeled in FIG. 1, although other joint encoders 122 may be similarly illustrated. In the representative embodiment illustrated herein, the robotic arm 108 has six joints J1, J2, J3, J4, J5, J6 implementing at least six degrees of freedom (DOF) for the manipulator 102. However, the manipulator 102 may have any suitable number of degrees of freedom, may have any suitable number of joints J, and may have redundant joints J. The manipulator 102 need not require joint encoders 122 but may alternatively, or additionally, utilize motor encoders present on motors at each joint J. Furthermore, the manipulator 102 need not require rotary joints, but may alternatively, or additionally, utilize one or more prismatic joints. Any suitable combination of joint types are contemplated.

The surgical system 100 is able to monitor, track, and/or determine changes in the relative position and/or orientation of one or more parts of the manipulator 102, the robotic arm 108, the tool 104, the instrument 112, the energy applicator 114, and/or the implantable component 116, as well as various parts of the patient's body B, within a common coordinate system by utilizing various types of trackers (e.g., multiple degree-of-freedom optical, inertial, and/or ultrasonic sensing devices), navigation systems (e.g., machine vision systems, charge coupled device cameras, tracker sensors, surface scanners, and/or range finders), anatomical computer models (e.g., magnetic resonance imaging scans of the patient's P anatomy), data from previous surgical procedures and/or previously-performed surgical techniques (e.g., data recorded during prior steps of the surgical procedure), and the like. To these ends, and as is depicted schematically in FIG. 1, the surgical system 100 employs a control system 124 (also referred to as a "controller" 124) which may comprise or otherwise communicate with one or more of a robotic control system 126, a navigation system 128, and a tool control system 130 which cooperate to facilitate positioning, moving, and/or driving the tool 104 relative to the target site TS and other parts of the surgical system 100 via the manipulator 102, as described in greater detail below. Exemplary control methodologies are described in U.S. Pat. No. 10,327,849, entitled "Robotic System and Method for Backdriving the Same," the disclosure of which is hereby incorporated by reference in its entirety.

The base 106, or another portion of the manipulator 102, generally provides a fixed reference coordinate system for other components of the manipulator 102 and/or other components of the surgical system 100. Generally, the origin of a manipulator coordinate system MNPL is defined at the fixed reference of the base 106. The base 106 may be defined with respect to any suitable portion of the manipulator 102, such as one or more of the links 120. Alternatively, or additionally, the base 106 may be defined with respect to the manipulator cart 118, such as where the manipulator 102 is physically attached to the cart 118. In some embodiments, the base 106 is defined at an intersection of the axis of joint J1 and the axis of joint J2. Thus, although joint J1 and joint J2 are moving components in reality, the intersection of the axes of joint J1 and joint J2 is nevertheless a virtual fixed reference pose, which provides both a fixed position and orientation reference and which does not move relative to the manipulator 102 and/or the manipulator cart 118. In some embodiments, the manipulator 102 could be hand-held such that the base 106 would be defined by a base portion of a tool (e.g., a portion held free-hand by the user) with a tool tip (e.g., an end effector) movable relative to the base portion. In this embodiment, the base portion has a reference coordinate system that is tracked, and the tool tip has a tool tip coordinate system that is computed relative to the reference coordinate system (e.g., via motor and/or joint encoders and forward kinematic calculations). Movement of the tool tip can be controlled to follow a path since its pose relative to the path can be determined. One example of this type of hand-held manipulator 102 is shown in U.S. Pat. No. 9,707,043, entitled "Surgical Instrument Including Housing, A Cutting Accessory that Extends from the Housing and Actuators that Establish the Position of the Cutting Accessory Relative to the Housing," the disclosure of which is hereby incorporated by reference in its entirety. The forgoing is a non-limiting, illustrative example, and other configurations are contemplated by the present disclosure.

As is depicted schematically in FIG. 1, the robotic control system 126 comprises a manipulator controller 132, the navigation system 128 comprises a navigation controller 134, and the tool control system 130 comprises a tool controller 136. In the illustrated embodiment, the manipulator controller 132, the navigation controller 134, and the tool controller 136 are generally disposed in communication with each other (e.g., directly or indirectly), and/or with other components of the surgical system 100, such as via physical electrical connections (e.g., a tethered wire harness) and/or via one or more types of wireless communication (e.g., with a WiFi™ network, Bluetooth®, a radio network, and the like). The manipulator controller 132, the navigation controller 134, and/or the tool controller 136 may be realized as or with various arrangements of computers, processors, control units, and the like, and may comprise discrete components or may be integrated (e.g., sharing hardware, software, inputs, outputs, and the like). Other configurations are contemplated.

The manipulator controller 132, the navigation controller 134, and/or the tool controller 136 may each be realized as a computer with a processor 138 (e.g., a central processing unit) and/or other processors, memory 140, and/or storage (not shown), and are generally loaded with software as described in greater detail below. The processors 138 could include one or more processors to control operation of the manipulator 102, the navigation system 128, or the tool 104. The processors 138 could be any type of microprocessor, multi-processor, and/or multi-core processing system. The manipulator controller 132, the navigation controller 134, and/or the tool controller 136 may additionally or alternatively comprise one or more microcontrollers, field programmable gate arrays, systems on a chip, discrete circuitry, and/or other suitable hardware, software, and/or firmware capable of carrying out the functions described herein. The term "processor" is not intended to limit any embodiment to a single processor. The robotic control system 126, the navigation system 128, and/or the tool control system 130 may also comprise, define, or otherwise employ a user interface 142 with one or more output devices 144 (e.g., screens, displays, status indicators, and the like) and/or input devices 146 (e.g., push button, keyboard, mouse, microphone, voice-activation devices, gesture control devices, touchscreens, foot pedals, pendants, and the like). Other configurations are contemplated.

As noted above, one or more tools 104 (sometimes referred to as "end effectors") releasably attach to the coupling 110 of the manipulator 102 and are movable relative to the base 106 to interact with the anatomy of the patient P (e.g., the target site TS) in certain modes. The tool 104 may be grasped by the user (e.g., a surgeon). The tool 104 generally includes a mount 148 that is adapted to releasably attach to the coupling 110 of the manipulator 102. The mount 148 may support or otherwise be defined by the instrument 112 which, in some embodiments, may be configured as a powered surgical device 150 which employs a power generation assembly 152 (e.g., a motor, an actuator, gear trains, and the like) used to drive the energy applicator 114 attached thereto (e.g., via a chuck, a coupling, and the like). One exemplary arrangement of this type of manipulator 102, tool 104, and instrument 112 is described in U.S. Pat. No. 9,119,655, entitled "Surgical Manipulator Capable of Controlling a Surgical Instrument in Multiple Modes," previously referenced. The manipulator 102, the tool 104, and/or the instrument 112 may be arranged in alternative configurations. In some embodiments, the tool 104 and/or the instrument 112 may be like that shown in U.S. Pat. No. 9,566,121, entitled "End Effector of a Surgical Robotic Manipulator," the disclosure of which is hereby incorporated by reference in its entirety. In some embodiments, the tool 104 and/or the instrument 112 may be like that shown in U.S. Patent Application Publication No. US 2019/0231447 A1, entitled "End Effectors And Methods For Driving Tools Guided By Surgical Robotic Systems," the disclosure of which is hereby incorporated by reference in its entirety. Other configurations are contemplated. In some embodiments, and as is described in greater detail below, the instrument 112 may not be configured as a powered surgical device 150.

In some embodiments, the energy applicator 114 is designed to contact and remove the tissue of the patient P at the target site TS. To this end, the energy applicator 114 may comprise a bur 154 in some embodiments. The bur 154 may be substantially spherical and comprise a spherical center, a radius, and a diameter. Alternatively, the energy applicator 114 may be a drill bit, a saw blade, an ultrasonic vibrating tip, and the like. The tool 104, the instrument 112, and/or the energy applicator 114 may comprise any geometric feature, including without limitation a perimeter, a circumference, a radius, a diameter, a width, a length, a volume an area, a surface/plane, a range of motion envelope (along any one or more axes), and the like. The geometric feature may be considered to determine how to locate the tool 104 relative to the tissue at the target site TS to perform the desired treatment. In some of the embodiments described herein, a spherical bur 154 having or otherwise defining tool center point (TCP) will be described for convenience and ease of illustration, but is not intended to limit the tool 104, the instrument 112, and/or the energy applicator 114 to any particular form. In some of the embodiments described herein, the tool center point TCP is defined by a portion of the instrument 112 or the tool 104 rather than the energy applicator 114. Other configurations are contemplated.

In some embodiments, such as where the instrument 112 is realized as a powered surgical device 150, the tool 104 may employ the tool controller 136 to facilitate operation of the tool 104, such as to control power to the power generation assembly 152 (e.g., a rotary motor), control movement of the tool 104, control irrigation/aspiration of the tool 104, and the like. The tool controller 136 may be in communication with the manipulator controller 132 and/or other components of the surgical system 100. In some embodiments, the manipulator controller 132 and/or the tool controller 136 may be housed in the manipulator 102 and/or the manipulator cart 118. In some embodiments, parts of the tool controller 136 may be housed in the tool 104. Other configurations are contemplated. The tool control system 130 may also comprise the user interface 142, with one or more output devices 144 and/or input devices 146, which may formed as a part of the tool 104 and/or may be realized by other parts of the surgical system 100 and/or the control system 124 (e.g., the robotic control system 126 and/or the navigation system 128). Other configurations are contemplated.

The manipulator controller 132 controls a state (position and/or orientation) of the tool 104 (e.g., the tool center point TCP) with respect to a coordinate system, such as the manipulator coordinate system MNPL. The manipulator controller 132 can control (linear or angular) velocity, acceleration, or other derivatives of motion of the tool 104. The tool center point TCP, in one example, is a predetermined reference point defined at the energy applicator 114. However, as noted above, other components of the tool 104 and/or instrument 112 could define the tool center point TCP in some embodiments. In any event, the tool center point TCP has a known pose relative to other coordinate systems. The pose of the tool center point TCP may be static or may be calculated. In some embodiments, the geometry of the energy applicator 114 is known in or defined relative to a tool center point TCP coordinate system. The tool center point TCP may be located at the spherical center of the bur 154 of the energy applicator 114 supported or defined by the instrument 112 of the tool 104 such that only one point is tracked. The tool center point TCP may be defined in various ways depending on the configuration of the energy applicator 114, the instrument 112, the tool 104, and the like.

The manipulator 102 could employ the joint encoders 122 (and/or motor encoders, as noted above), or any other non-encoder position sensing method, to enable a pose of the tool center point TCP to be determined. The manipulator 102 may use joint J measurements to determine the tool center point TCP pose, and/or could employ various techniques to measure the tool center point TCP pose directly. The control of the tool 104 is not limited to a center point. For example, any suitable primitives, meshes, and the like can be used to represent the tool 104. Other configurations are contemplated.

With continued reference to FIG. 1, as noted above, the surgical system 100 also includes the navigation system 128 which, among other things, is configured to track, monitor, detect, or otherwise sense movement of various objects, such as the tool 104, a pointer 156 used for registering objects (e.g., portions of the anatomy, trackers, and the like), and parts of the patient's body B (e.g., bones or other anatomy at or adjacent to the target site TS). To this end, the navigation system 128 employs a localizer 158 configured to sense the position and/or orientation of trackers 160 within a localizer coordinate system LCLZ. The navigation controller 134 is disposed in communication with the localizer 158 and gathers position and/or orientation data for each tracker 160 sensed within a field of view of the localizer 158 in the localizer coordinate system LCLZ.

The localizer 158 can sense the position and/or orientation of a plurality of trackers 160 to track a corresponding plurality of objects within the localizer coordinate system LCLZ. By way of example, and as is depicted in FIG. 1, trackers 160 may comprise a pointer tracker 160P coupled to the pointer 156, a manipulator tracker 160M coupled to the base 106 of the manipulator 102, one or more tool trackers 160G, 160I coupled to portions of the tool 104, a first patient tracker 160A coupled to one portion of the anatomy of the patient P, and a second patient tracker 160B coupled to another portion of the anatomy of the patient P, as well as additional patient trackers, trackers for additional medical and/or surgical tools, instruments, and the like.

In some embodiments, and as is shown in FIG. 1, the one or more tool trackers 160G, 160I may each be firmly affixed to different portions of the tool 104, such as those that may be configured to move relative to each other and/or to the manipulator tracker 160M, which is firmly affixed to the base 106 of the manipulator 102. By way of non-limiting example, and as is described in greater detail below, a first tool tracker 160G could be coupled to the mount 148 (or to another part of the tool 104) for concurrent movement with the coupling 110 via the manipulator 102, and a second tool tracker 160I could be coupled to a different portion of the tool 104 which moves relative to the mount 148 and/or the coupling 110 in one or more degrees of freedom. While the first tool tracker 160G and the second tool tracker 160I depicted in FIG. 1 can be used by the navigation system 128 to readily determine the relative positions and/or orientations of different parts of the tool 104 via the localizer 158, certain embodiments of the present disclosure may be configured to facilitate this determination in other ways (e.g., such as with one or more sensors). Here, other configurations are contemplated by the present disclosure, and various combinations of trackers 160, sensors, predetermined geometric relationships, and the like can be utilized in order to track certain objects or otherwise relate those objects to a tracked object.

With continued reference to FIG. 1, the first patient tracker 160A is firmly affixed to one bone of the patient's body B at or adjacent to the target site TS (e.g., to the pelvis near the acetabulum), and the second patient tracker 160B is firmly affixed to a different bone (e.g., to a portion of the femur). While not shown in detail, the patient trackers 160A, 160B can be coupled to a number of different bones in the patient's body B in various ways, such as by threaded engagement, clamping, or by other techniques. Similarly, the first tool tracker 160G and/or the second tool tracker 160I could be fixed to portions of the tool 104 in various ways, such as by integration during manufacture or by releasable attachment ahead of or during a surgical procedure. Various trackers 160 may be firmly affixed to different types of tracked objects (e.g., discrete bones, tools, pointers, and the like) in a number of different ways. For example, trackers 160 may be rigidly fixed, flexibly connected (optical fiber), or not physically connected at all (ultrasound), as long as there is a suitable (e.g., supplemental) way to determine the relationship (e.g., measurement) of that respective tracker 160 to the object or anatomy that it is associated with.

The position and/or orientation of the trackers 160 relative to the objects or anatomy to which they are attached can be determined by utilizing known registration techniques. For example, determining the pose of the patient trackers 160A, 160B relative to the portions of the patient's body B to which they are attached can be accomplished with various forms of point-based registration, such as where a distal tip of the pointer 156 is used to engage against specific anatomical landmarks (e.g., touching specific portions of bone) or is used to engage several parts of a bone for surface-based registration as the localizer 158 monitors the position and orientation of the pointer tracker 160P. Conventional registration techniques can then be employed to correlate the pose of the patient trackers 160A, 160B to the patient's anatomy (e.g., to each of the femur and the acetabulum).

Other types of registration are also possible, such as by using patient trackers 160A, 160B with mechanical clamps that attach to bone and have tactile sensors (not shown) to determine a shape of the bone to which the clamp is attached. The shape of the bone can then be matched to a three-dimensional model of bone for registration. A known relationship between the tactile sensors and markers 162 on the patient tracker 160A, 160B may be entered into or otherwise known by the navigation controller 134 (e.g., stored in memory 140). Based on this known relationship, the positions of the markers 162 relative to the patient's anatomy can be determined. Position and/or orientation data may be gathered, determined, or otherwise handled by the navigation controller 134 using a number of different registration/navigation techniques to determine coordinates of each tracker 160 within the localizer coordinate system LCLZ or another suitable coordinate system. These coordinates are communicated to other parts of the control system 124, such as to the robotic control system 126 to facilitate articulation of the manipulator 102 and/or to otherwise assist the surgeon in performing the surgical procedure, as described in greater detail below.

In the representative embodiment illustrated herein, the manipulator controller 132 and the tool controller 136 are operatively attached to the base 106 of the manipulator 102, and the navigation controller 134 and the localizer 158 are supported on a mobile cart 164 which is movable relative to the base 106 of the manipulator 102. The mobile cart 164 may also support the user interface 142 to facilitate operation of the surgical system 100 by displaying information to, and/or by receiving information from, the surgeon or another user. While shown as a part of the navigation system 128 in the representative embodiment illustrated in FIG. 1, the user interface 142 could form part of, or otherwise communicate with, other parts of the control system 124 such as the robotic control system 126 and/or the tool control system 130. To this end, the user interface 142 may be disposed in communication with navigation controller 134, the manipulator controller 132, and/or the tool controller 136, and may likewise comprise one or more output devices 144 (e.g., monitors, indicators, display screens, and the like) to present information to the surgeon or other users (e.g., images, video, data, graphics, navigable menus, and the like), and one or more input devices 146 (e.g., physical or virtual input controls, buttons, touch screens, keyboards, mice, gesture or voice-based input devices, and the like). One type of mobile cart 164 and user interface 142 utilized in this type of navigation system 128 is described in U.S. Pat. No. 7,725, 162, entitled "Surgery System," the disclosure of which is hereby incorporated by reference in its entirety.

Because the mobile cart 164 and the base 106 of the manipulator 102 can be positioned relative to each other and also relative to the patient's body B, one or more portions of the surgical system 100 are generally configured to transform the coordinates of each tracker 160 sensed via the localizer 158 from the localizer coordinate system LCLZ into the manipulator coordinate system MNPL (or to other coordinate systems), or vice versa, so that articulation of the manipulator 102 can be performed based at least partially on the relative positions and/or orientations of certain trackers 160 within a common coordinate system (e.g., the manipulator coordinate system MNPL, the localizer coordinate system LCLZ, or another common coordinate system). Coordinates within the localizer coordinate system LCLZ can be transformed into coordinates within the manipulator coordinate system MNPL (or other coordinate systems), and vice versa, using a number of different transformation techniques. One example of the translation or transformation of data between coordinate systems is described in U.S. Pat. No. 8,675,939, entitled "Registration of Anatomical Data Sets", the disclosure of which is hereby incorporated by reference in its entirety.

In the illustrated embodiment, the localizer 158 is an optical localizer and includes a camera unit 166 with one or more optical sensors 168 and, in some embodiments, a video camera 170. The localizer 158 may also comprise a localizer controller (not shown) which communicates with the navigation controller 134 or otherwise forms part of the navigation system 128. The navigation system 128 employs the optical sensors 168 of the camera unit 166 to sense the position and/or orientation of the trackers 160 within the localizer coordinate system LCLZ. In the representative embodiment illustrated herein, the trackers 160 each employ a plurality of markers 162 (see FIG. 2) which can be sensed by the optical sensors 168 of the camera unit 166. One example of a navigation system 128 of this type is described in U.S. Pat. No. 9,008,757, entitled "Navigation System Including Optical and Non-Optical Sensors," the disclosure of which is hereby incorporated by reference in its entirety. In some embodiments, the markers 162 are active markers (e.g., light emitting diodes "LEDs") which emit light that can be sensed by the localizer 158. In some embodiments, the trackers 160 may employ passive markers (e.g., reflectors) which reflect light emitted from the localizer 158 or another light source. Although one embodiment of the navigation system 128 is illustrated throughout the drawings, the navigation system 128 could have any suitable configuration for monitoring trackers 160 which, as will be appreciated from the subsequent description below, may be of various types and configurations. For example, the navigation system 128 may comprise multiple localizers 158 and/or trackers 160 of the same or different type.

In some embodiments, the navigation system 128 and/or the localizer 158 are radio frequency (RF) based. For example, the navigation system 128 may comprise an RF transceiver coupled to the navigation controller 134 and/or to another computing device, controller, and the like. Here, the trackers 160 may comprise RF emitters or transponders, which may be passive or may be actively energized. The RF transceiver transmits an RF tracking signal, and the RF emitters respond with RF signals such that tracked states are communicated to (or interpreted by) the navigation controller 134. The RF signals may be of any suitable frequency. The RF transceiver may be positioned at any suitable location to track the objects using RF signals effectively. Furthermore, embodiments of RF-based navigation systems may have structural configurations that are different than the active marker-based navigation system 128 illustrated herein.

In some embodiments, the navigation system 128 and/or localizer 158 are electromagnetically (EM) based. For example, the navigation system 128 may comprise an EM transceiver coupled to the navigation controller 134 and/or to another computing device, controller, and the like. Here, the trackers 160 may comprise EM components attached thereto (e.g., various types of magnetic trackers, electromagnetic trackers, inductive trackers, and the like), which may be passive or may be actively energized. The EM transceiver generates an EM field, and the EM components respond with EM signals such that tracked states are communicated to (or interpreted by) the navigation controller 134. The navigation controller 134 may analyze the received EM signals to associate relative states thereto. Here too, embodiments of EM-based navigation systems may have structural configurations that are different than the active marker-based navigation system 128 illustrated herein.

In some embodiments, the navigation system 128 and/or the localizer 158 could be based on one or more types of imaging systems that do not necessarily require trackers 160 to be fixed to objects in order to determine location data associated therewith. For example, an ultrasound-based imaging system could be provided to facilitate acquiring ultrasound images (e.g., of specific known structural features of tracked objects, of markers or stickers secured to tracked objects, and the like) such that tracked states (e.g., position, orientation, and the like) are communicated to (or interpreted by) the navigation controller 134 based on the ultrasound images. The ultrasound images may be three-dimensional, two-dimensional, or a combination thereof. The navigation controller 134 may process ultrasound images in near real-time to determine the tracked states. The ultrasound imaging device may have any suitable configuration and may be different than the camera unit 166 as shown in FIG. 1. By way of further example, a fluoroscopy-based imaging system could be provided to facilitate acquiring X-ray images of radio-opaque markers (e.g., stickers, tags, and the like with known structural features that are attached to tracked objects) such that tracked states are communicated to (or interpreted by) the navigation controller 134 based on the X-ray images. The navigation controller 134 may process X-ray images in near real-time to determine the tracked states. Similarly, other types of optical-based imaging systems could be provided to facilitate acquiring digital images, video, and the like (e.g., via a charge-coupled device "CCD" sensor such as the video camera 170) of specific known objects (e.g., based on a comparison to a virtual representation of the tracked object or a structural component or feature thereof) and/or markers (e.g., stickers, tags, and the like that are attached to tracked objects) such that tracked states are communicated to (or interpreted by) the navigation controller 134 based on the digital images. The navigation controller 134 may process digital images in near real-time to determine the tracked states.

Accordingly, various types of imaging systems, including multiple imaging systems of the same or different type, may form a part of the navigation system 128 without departing from the scope of the present disclosure. The navigation system 128 and/or localizer 158 may have other suitable components or structure not specifically recited herein. For example, the navigation system 128 may utilize solely inertial tracking or any combination of tracking techniques, and may additionally or alternatively comprise fiber optic-based tracking, machine-vision tracking, and the like. Furthermore, any of the techniques, methods, and/or components associated with the navigation system 128 illustrated in FIG. 1 may be implemented in a number of different ways, and other configurations are contemplated by the present disclosure.

In some embodiments, the surgical system 100 is capable of displaying a virtual representation of the relative positions and orientations of tracked objects to the surgeon or other users of the surgical system 100, such as with images and/or graphical representations of the anatomy of the patient's body B, the tool 104, the instrument 112, the energy applicator 114, and the like presented on one or more output devices 144 (e.g., a display screen). The manipulator controller 132 and/or the navigation controller 134 may also utilize the user interface 142 to display instructions or request information such that the surgeon or other users may interact with the robotic control system 126 (e.g., using a graphical user interface GUI) to facilitate articulation of the manipulator 102. Other configurations are contemplated.

As noted above, the localizer 158 tracks the trackers 160 to determine a state of each of the trackers 160 which corresponds, respectively, to the state of the object respectively attached thereto. The localizer 158 may perform known triangulation techniques to determine the states of the trackers 160 and associated objects. The localizer 158 provides the state of the trackers 160 to the navigation controller 134. In some embodiments, the navigation controller 134 determines and communicates the state of the trackers 160 to the manipulator controller 132. As used herein, the state of an object includes, but is not limited to, data that defines the position and/or orientation of the tracked object, or equivalents/derivatives of the position and/or orientation. For example, the state may be a pose of the object, and may include linear velocity data, and/or angular velocity data, and the like. Other configurations are contemplated.

Figure 2:
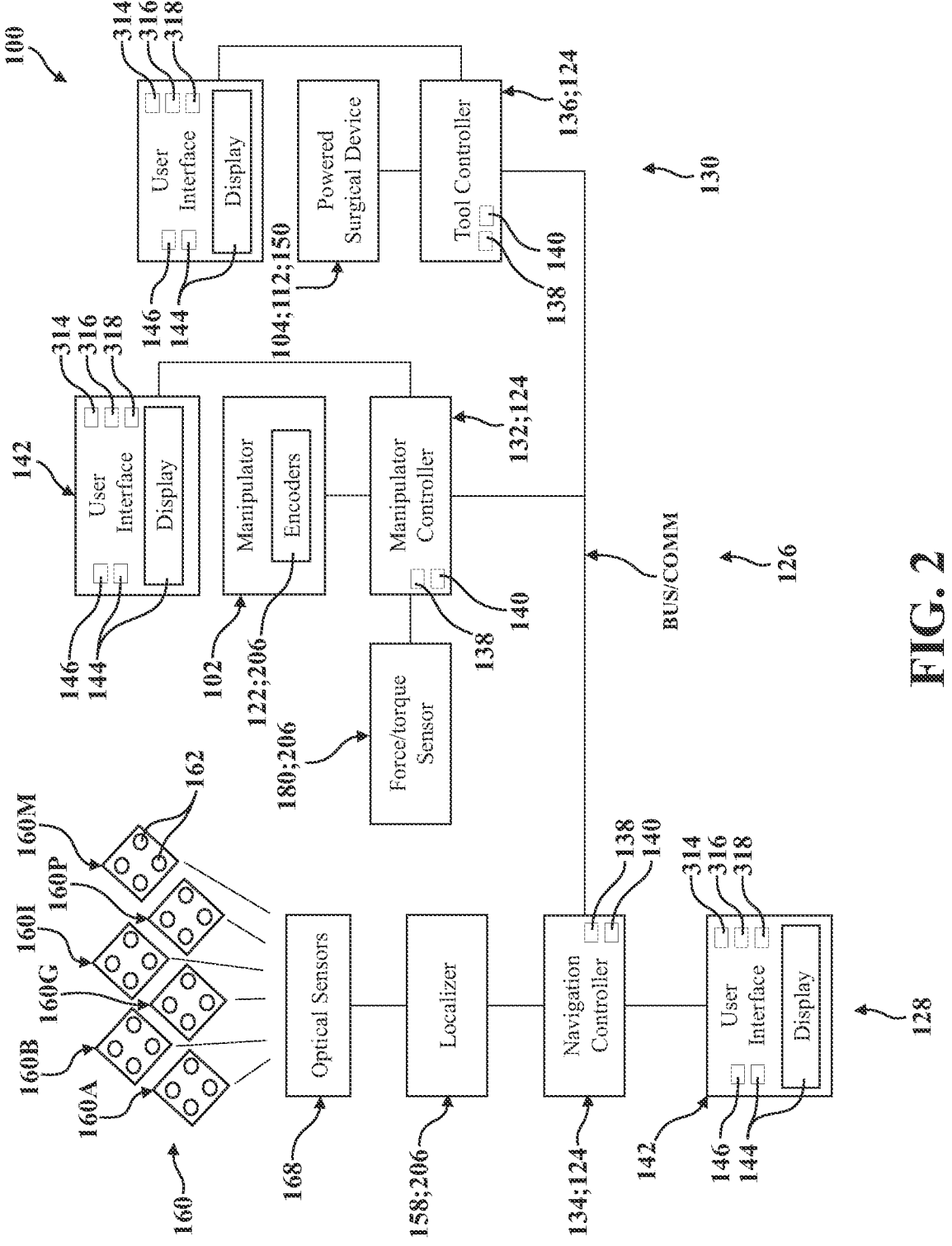
FIG. 2 is a block diagram of a control system for controlling the surgical system of FIG. 1.

Referring to FIG. 2, the surgical system 100 generally comprises the control system 124 which, among other components, may include or otherwise be defined as the manipulator controller 132, the navigation controller 134, the tool controller 136, and/or various components of the robotic control system 126, the navigation system 128, and/or the tool control system 130 as noted above. The control system 124 may also include one or more software modules shown in FIG. 3. The software modules may be part of one or more programs that operate on the manipulator controller 132, the navigation controller 134, the tool controller 136, or any combination thereof, to process data used to facilitate or otherwise assist with control of the surgical system 100. The software programs and/or modules include computer readable instructions stored in non-transitory memory 140 on the manipulator controller 132, the navigation controller 134, the tool controller 136, or a combination thereof, to be executed by one or more processors 138 of one or more of the controllers 136, 132, 134.

The memory 140 may be of any suitable configuration, such as random-access memory (RAM), non-volatile memory, and the like, and may be implemented locally or from a remote location (e.g., a database, a server, and the like). Additionally, software modules for prompting and/or communicating with the user may form part of the modules or programs, and may include instructions stored in memory 140 on the manipulator controller 132, the navigation controller 134, the tool controller 136, or any combination thereof. The user may interact with any of the input devices 146 and/or output devices 144 of any of the user interfaces 142 (e.g., the user interface 142 of the navigation system 128 shown in FIG. 1) to communicate with the software modules and/or programs. The control system 124 may also comprise user interfaces 142 (e.g., a graphical user interface GUI) or other software or modules that could run on a separate device from the manipulator controller 132, the navigation controller 134, and/or the tool controller 136 (e.g., a portable electronic device such as a tablet computer). Other configurations are contemplated.

The control system 124 may comprise any suitable arrangement and/or configuration of input, output, and processing devices suitable for carrying out the functions and methods described herein. The surgical system 100 may comprise the manipulator controller 132, the navigation controller 134, or the tool controller 136, or any combination thereof, or may comprise only some of these controllers, or additional controllers, any of which could form part of the control system 124 as noted above. The controllers 132, 134, 136 may communicate via a wired bus or communication network as shown in FIG. 2, via wireless communication, or otherwise. The control system 124 may also be referred to as a controller, and may likewise comprise one or more micro-controllers, field programmable gate arrays, systems on a chip, discrete circuitry, sensors, displays, user interfaces, indicators, and/or other suitable hardware, software, or firmware that is capable of carrying out the functions described herein. Other configurations are contemplated.

Figure 3:
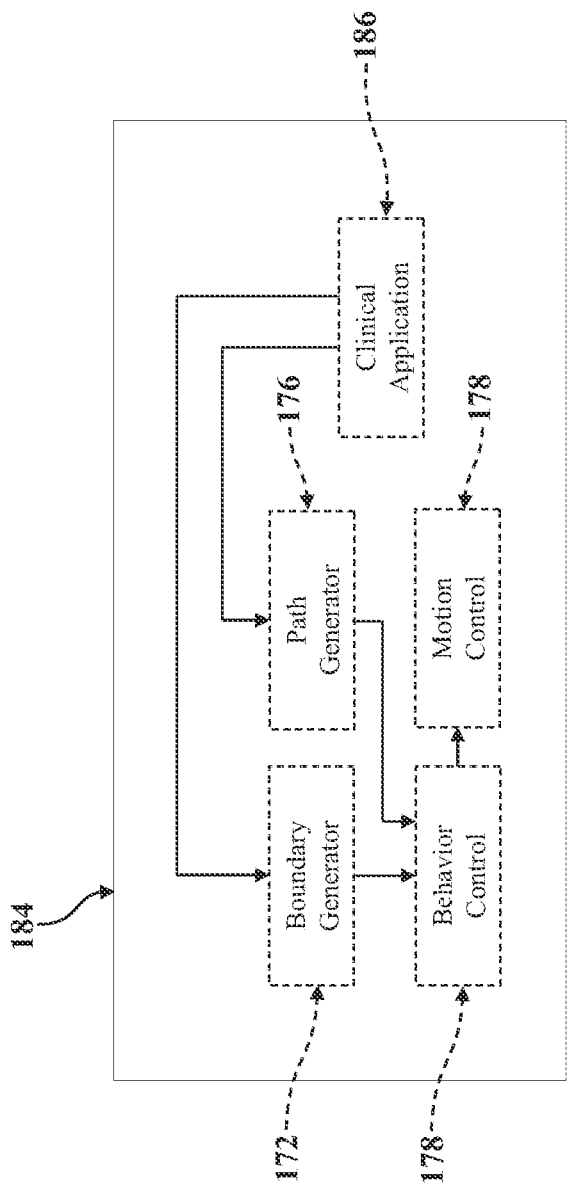
FIG. 3 is a functional block diagram of a software program of the control system of FIG. 2.
Figures 4, 5:
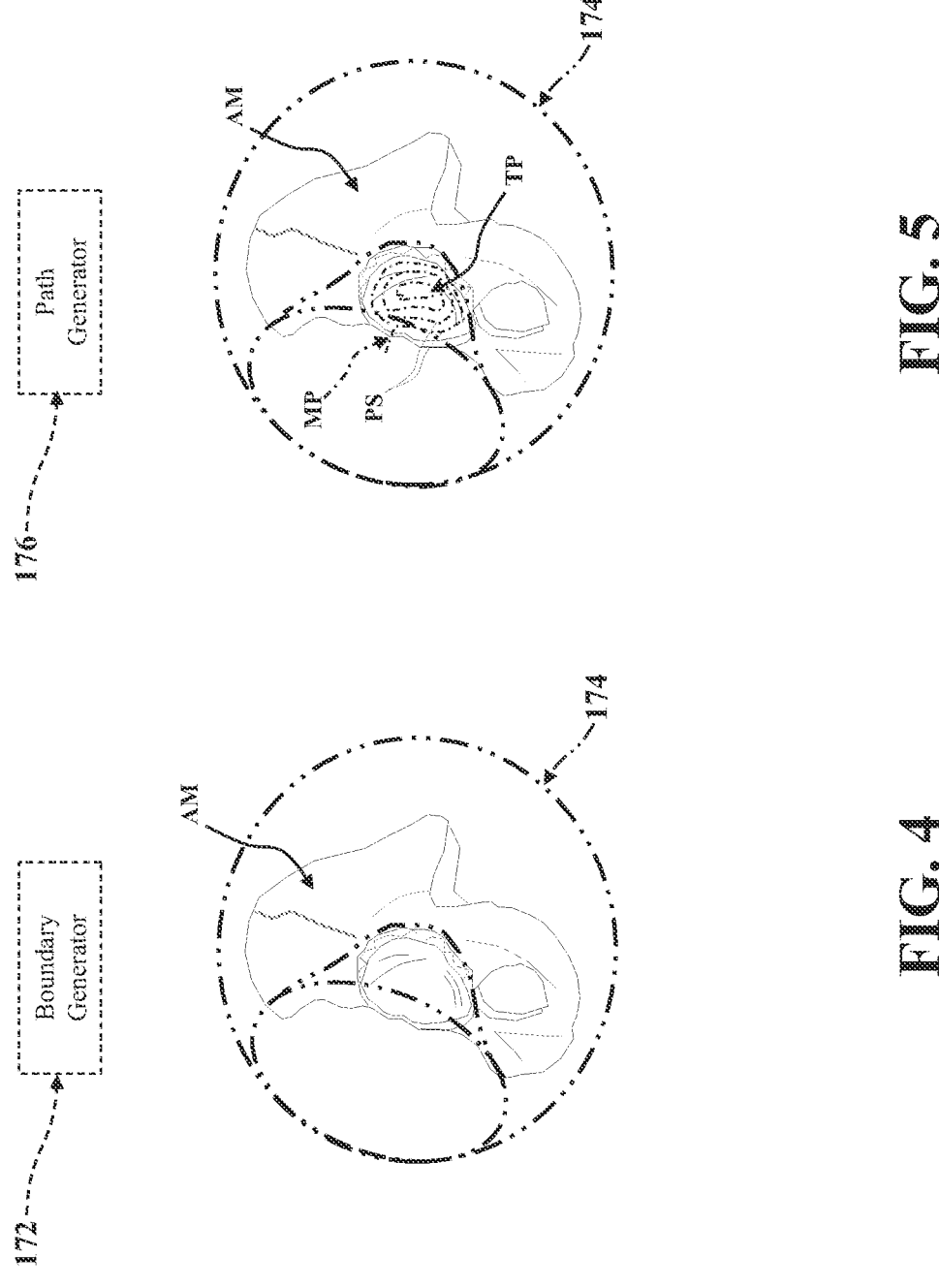
FIG. 4 is an illustrative view of a target site realized as an acetabulum depicting an output of a boundary generator of the software program of FIG. 3.
FIG. 5 is an illustrative view of the target site of FIG. 4 depicting an output of a path generator of the software program of FIG. 3.

Referring to FIG. 3, in some embodiments, the software employed by the control system 124 may include a boundary generator 172. As shown in FIG. 4, the boundary generator 172 is a software program or module that generates a virtual boundary 174 for constraining movement and/or operation of the tool 104. The virtual boundary 174 may be one-dimensional, two-dimensional, or three-dimensional, and may comprise a point, line, axis, trajectory, plane, or other shapes, including complex geometric shapes. In some embodiments, the virtual boundary 174 is a surface defined by a triangle mesh. Such virtual boundaries 174 may also be referred to as virtual objects. The virtual boundaries 174 may be defined with respect to an anatomical model AM, such as a three-dimensional bone model. The anatomical model Am is associated with the real anatomy of the patient P by virtue of the anatomical model AM being mapped to the anatomy of the patient P via registration or other processes. In the example of FIG. 4, the virtual boundaries 174 comprises a generally spherical mesh substantially surrounding an acetabulum with an entry portion (e.g., an opening) that provides access to the acetabulum. The entry portion has a funnel or conical shape. In this representative embodiment, the virtual boundary 174 is associated with a three-dimensional model of the acetabulum of the pelvis.

The anatomical model AM and associated virtual boundaries 174 are registered to one or more patient trackers 160A, 160B. Thus, the anatomical model AM (and the associated real anatomy of the patient P) and the virtual boundaries 174 fixed to the anatomical model AM can be tracked by the patient trackers 160A, 160B. The virtual boundaries 174 may be implant-specific (e.g., defined based on a size, shape, volume, and the like of an implantable component 116) and/or patient-specific (e.g., defined based on the anatomy of the patient P). The virtual boundaries 174 may be boundaries that are created pre-operatively, intra-operatively, or combinations thereof. In other words, the virtual boundaries 174 may be defined before the surgical procedure begins, during the surgical procedure (including during tissue removal), or combinations thereof. In any event, the control system 124 obtains the virtual boundaries 174 by storing/retrieving the virtual boundaries 174 in/from memory 140, obtaining the virtual boundaries 174 from memory 140, creating the virtual boundaries 174 pre-operatively, creating the virtual boundaries 174 intra-operatively, and the like.

The manipulator controller 132 and/or the navigation controller 134 may track the state of the tool 104 relative to the virtual boundaries 174. In some embodiments, the state of the tool center point TCP is measured relative to the virtual boundaries 174 for purposes of determining haptic forces to be applied to a virtual rigid body VRB model via a virtual simulation VS so that the tool 104 remains in a desired positional relationship to the virtual boundaries 174 (e.g., not moved beyond them). The results of the virtual simulation VS are commanded to the manipulator 102. The control system 124 (e.g., the manipulator controller 132 of the robotic control system 126) controls/positions the manipulator 102 in a manner that emulates the way a physical handpiece would respond in the presence of physical boundaries/barriers. The boundary generator 172 may be implemented on the manipulator controller 132. Alternatively, the boundary generator 172 may be implemented on other components, such as the navigation controller 134, or other portions of the control system 124. Other configurations are contemplated.

Referring to FIG. 3 and FIG. 5, a path generator 176 is another software program or module that may be run by the control system 124. In some embodiments, the path generator 176 is run by the manipulator controller 132. The path generator 176 generates a tool path TP for the tool 104 to traverse, such as for removing sections of the anatomy of the patient P at the target site TS to receive an implantable component 116. The tool path TP may comprise a plurality of path segments PS, or may comprise a single path segment PS. The path segments PS may be straight segments, curved segments, combinations thereof, and the like. The tool path TP may also be defined with respect to the anatomical model AM. The tool path TP may be implant-specific (e.g., defined based on a size, shape, volume, and the like of an implantable component 116) and/or patient-specific (e.g., defined based on the anatomy of the patient P). Other configurations are contemplated.

In some embodiments described herein, the tool path TP is defined as a tissue removal path adjacent to the target site TS. However, in some embodiments, the tool path TP may be used for treatment other than tissue removal. One example of the tissue removal path described herein comprises a milling path MP. It should be understood that the term "milling path" generally refers to the path of the tool 104 in the vicinity of the target site TS for milling the anatomy, and is not intended to require that the tool 104 be operably milling the anatomy throughout the entire duration of the path. For instance, the milling path MP may comprise sections or segments where the tool 104 transitions from one location to another without milling. Additionally, other forms of tissue removal along the milling path MP may be employed, such as tissue ablation, and the like. The milling path MP may be a predefined path that is created pre-operatively, intra-operatively, or combinations thereof. In other words, the milling path MP may be defined before the surgical procedure begins, during the surgical procedure (including during tissue removal), or combinations thereof. In any event, the control system 124 obtains the milling path MP by storing/retrieving the milling path MP in/from memory 140, obtaining the milling path MP from memory 140, creating the milling path MP pre-operatively, creating the milling path MP intra-operatively, and the like. The milling path MP may have any suitable shape, or combinations of shapes, such as circular, helical/corkscrew, linear, curvilinear, combinations thereof, and the like. Other configurations are contemplated.

One example of a system and method for generating the virtual boundaries 174 and/or the milling path MP is described in U.S. Pat. No. 9,119,655, entitled "Surgical Manipulator Capable of Controlling a Surgical Instrument in Multiple Modes," previously referenced. Further examples are described in U.S. Pat. No. 8,010,180, entitled "Haptic Guidance System and Method;" and U.S. Pat. No. 7,831, 292, entitled "Guidance System and Method for Surgical Procedures with Improved Feedback," the disclosures of which are each hereby incorporated by reference in their entirety. In some embodiments, the virtual boundaries 174 and/or the milling paths MP may be generated offline rather than on the manipulator controller 132, navigation controller 134, or another component of the surgical system 100. Thereafter, the virtual boundaries 174 and/or milling paths MP may be utilized at runtime by the manipulator controller 132.

Referring back to FIG. 3, another software program or module which may be run on the manipulator controller 132 and/or the navigation controller 134 is shown for performing behavior control 178. Behavior control 178 is the process of computing data that indicates the next commanded position and/or orientation (e.g., pose) for the tool 104. In some cases, only the position or orientation of the tool center point TCP is output from the behavior control 178, while in other cases, the position and the orientation of the tool center point TCP is output from the behavior control 178. In some embodiments, output from the boundary generator 172, the path generator 176, and a sensor 180 (e.g., a six degree of freedom DOF force/torque transducer) may feed as inputs into the behavior control 178 to determine the next commanded position and/or orientation for the tool 104. The behavior control 178 may process these inputs, along with one or more virtual constraints VC as described in greater detail below, to determine a commanded pose CP.

With continued reference to FIG. 3, another software program or module which may be run on the manipulator controller 132 and/or the navigation controller 134 is shown for performing motion control 182. One aspect of motion control 182 is the control of the manipulator 102. The motion control 182 receives data defining the next commanded pose CP from the behavior control 178. Based on these data, the motion control 182 determines the next position of the joint angles of the joints J of the robotic arm 108 of the manipulator 102 (e.g., via inverse kinematics and Jacobian calculators) so that the manipulator 102 is able to position the tool 104 as commanded by the behavior control 178 (e.g., at the commanded pose CP). In other words, the motion control 182 processes the commanded pose CP, which may be defined in Cartesian space, into joint angles of the manipulator 102, so that the manipulator controller 132 can command the joint motors accordingly in order to move the joints J of the manipulator 102 to commanded joint angles corresponding to the commanded pose CP of the tool 104. In some embodiments, the motion control 182 regulates the joint angle of each joint J of the robotic arm 108 and continually adjusts the torque that each joint motor outputs in order to, as closely as possible, ensure that the joint motor drives the associated joint J to the commanded joint angle.

The boundary generator 172, the path generator 176, the behavior control 178, and the motion control 182 may be sub-sets (e.g., modules) of a software program 184. Alternatively, each may be a software program that operates separately and/or independently, or any combination thereof. The term "software program" is used herein to describe the computer-executable instructions that are configured to carry out the various capabilities of the technical solutions described. For simplicity, the term "software program" is intended to encompass, at least, any one or more of the boundary generator 172, the path generator 176, the behavior control 178, and/or the motion control 182. The software program 184 can be implemented on the manipulator controller 132, navigation controller 134, or any combination thereof, or may be implemented in any suitable manner by the control system 124.

In some embodiments, a clinical application 186 may be provided to facilitate user interaction and coordinate the surgical workflow, including pre-operative planning, implant placement, registration, bone preparation visualization, post-operative evaluation of implant fit, and the like. The clinical application 186 may be configured to output data to the output devices 144 (e.g., displays, screens, monitors, and the like), to receive input data from the input devices 146, or to otherwise interact with the user interfaces 142, and may include or form part of a graphical user interface GUI. The clinical application 186 may run on its own separate processor or may run alongside the navigation controller 134, the manipulator controller 132, and/or the tool controller 136, or any other suitable portion of the control system 124.

In some embodiments, the clinical application 186 interfaces with the boundary generator 172 and/or path generator 176 after implant placement is set by the user, and then sends the virtual boundary 174 and/or the tool path TP returned by the boundary generator 172 and/or the path generator 176 to the manipulator controller 132 for execution. Here, the manipulator controller 132 executes the tool path TP as described herein. The manipulator controller 132 may additionally create certain segments (e.g., lead-in segments) when starting or resuming machining to smoothly get back to the generated tool path TP. The manipulator controller 132 may also process the virtual boundaries 174 to generate corresponding virtual constraints VC as described in greater detail below.

The surgical system 100 may operate in a manual mode, such as described in U.S. Pat. No. 9,119,655, entitled "Surgical Manipulator Capable of Controlling a Surgical Instrument in Multiple Modes," previously referenced. Here, the user manually directs, and the manipulator 102 executes movement of the tool 104 and its energy applicator 114 at the surgical site. The user (e.g., the surgeon) physically contacts the tool 104 to cause movement of the tool 104 in the manual mode. In some embodiments, the manipulator 102 monitors forces and torques placed on the tool 104 by the user in order to position the tool 104. To this end, the surgical system 100 may employ the sensor 180 (e.g., a multiple degree of freedom DOF force/torque transducer) that detects and measures the forces and torques applied by the user to the tool 104 and generates corresponding input used by the control system 124 (e.g., one or more corresponding input/output signals). The forces and torques applied by the user at least partially define an external force $F_{ext}$ that is used to determine how to move the tool 104 in the manual mode (or other modes). The external force $F_{ext}$ may comprise other forces and torques, aside from those applied by the user, such as gravity-compensating forces, backdrive forces, and the like, as described in U.S. Pat. No. 9,119,655, entitled "Surgical Manipulator Capable of Controlling a Surgical Instrument in Multiple Modes," previously referenced. Thus, the forces and torques applied by the user at least partially define the external force $F_{ext}$, and in some cases may fully define the external force $F_{ext}$ that influences overall movement of the tool 104 in the manual mode and/or in other modes as described in greater detail below.

The sensor 180 may comprise a six degree of freedom DOF force/torque transducer arranged to detect forces and/or torque occurring between the manipulator 102 and the target site TS (e.g., forces applied to the tool 104 by the user). For illustrative purposes, the sensor 180 is generically-depicted adjacent to or otherwise as a part of the coupling 110 of the manipulator 102 (e.g., coupled to joint J6 of the robotic arm 108). However, other configurations and arrangements are contemplated. The manipulator controller 132, the navigation controller 134, the tool controller 136, and/or other components of the surgical system 100 may receive signals (e.g., as inputs) from the sensor 180. In response to the user-applied forces and torques, the manipulator 102 moves the tool 104 in a manner that emulates the movement that would have occurred based on the forces and torques applied by the user. Movement of the tool 104 in the manual mode may also be constrained in relation to the virtual boundaries 174 generated by the boundary generator 172. In some embodiments, measurements taken by the sensor 180 are transformed from a sensor coordinate system SN of the sensor 180 to another coordinate system, such as a virtual mass coordinate system VM, in which a virtual simulation VS is carried out on a virtual rigid body VRB model of the tool 104 so that the forces and torques can be virtually applied to the virtual rigid body VRB in the virtual simulation VS to ultimately determine how those forces and torques (among other inputs) would affect movement of the virtual rigid body VRB, as described below.

The surgical system 100 may also operate in a semi-autonomous mode in which the manipulator 102 moves the tool 104 in an automated manner along the milling path MP, such as by operating active joints J of the manipulator 102 to move the tool 104 without requiring force/torque on the tool 104 from the user. Examples of operation in the semi-autonomous mode are also described in U.S. Pat. No. 9,119,655, entitled "Surgical Manipulator Capable of Controlling a Surgical Instrument in Multiple Modes," previously referenced. In some embodiments, when the manipulator 102 operates in the semi-autonomous mode, the manipulator 102 is capable of moving the tool 104 free of user assistance. Here, "free of user assistance" may mean that the user does not physically contact the tool 104 or the robotic arm 108 to move the tool 104. Instead, the user may use some form of remote control (e.g., a pendant; not shown) to control starting and stopping of movement. For example, the user may hold down a button of the remote control to start movement of the tool 104 and release the button to stop movement of the tool 104. Examples of this type of remote control embodied in user pendant are described in U.S. Pat. No. 10,117,713, entitled "Robotic Systems and Methods for Controlling a Tool Removing Material from Workpiece," the disclosure of which is hereby incorporated herein by reference in its entirety. Other configurations are contemplated.

In the manual mode, it may be challenging for the user to move the tool 104 from a current state SC to a target state ST (e.g., to a target position PT, a target orientation OT, or a target pose). It may be desirable for the tool 104 to be moved to a particular target state ST for any number of reasons, such as to place the tool 104 in a desired proximity to the milling path MP, to place the tool 104 at an orientation suitable for preparing tissue to receive an implantable component 116, for aligning the tool 104 with a particular trajectory/plane, and the like. However, it may be difficult for the user to place the tool 104 with sufficient precision. This can be especially difficult when the anatomy of the patient P is partially obstructed from the user's view by soft tissue, fluids, and the like. Here, the surgical system 100 may be switched from the manual mode to the semi-autonomous mode, such as in the manner described in U.S. Pat. No. 9,119,655, entitled "Surgical Manipulator Capable of Controlling a Surgical Instrument in Multiple Modes," previously referenced. Accordingly, to place the tool 104 at the target state ST, the manipulator 102 may autonomously move the tool 104 from the current state SC to the target state ST.

Should the user wish to maintain manual contact with the tool 104 to effect control of the tool 104 during movement toward the target state ST, the surgical system 100 may also operate in a guided-haptic mode. The guided-haptic mode may be used to help guide the user into placing the tool 104 at or otherwise in the target state ST (attractive) or to guide the user away from the target state (repulsive). In the guided-haptic mode, aspects of control used in both the manual mode and the semi-autonomous mode are utilized. For example, forces and torques applied by the user are still detected by the sensor 180 to determine the external force $F_{ext}$ that is fed into the virtual simulation VS to at least partially influence overall movement of the tool 104. Additionally, in the guided-haptic mode, the surgical system 100 generates virtual attractive (or repulsive) forces VF (or torques) embodied in a virtual constraint VC force $F_c$ that is fed, along with the external force $F_{ext}$, into the virtual simulation VS. The guided-haptic mode may be used to keep the tool 104 from the target state ST (repulsive haptics), and/or to attract the tool 104 toward the target state ST (attractive haptics).

The virtual attractive force VF comprises forces and/or torques that can be virtually applied to the virtual rigid body VRB in the virtual simulation VS and that are adapted to attract or otherwise urge the tool 104 toward the target state ST. The virtual attractive force VF influences overall movement of the tool 104 in a way that provides the user with haptic feedback to indicate to the user how the tool 104 should be moved to reach the target state ST. More specifically, in the virtual simulation VS, the forces and/or torques associated with the virtual attractive force VF may counteract the effects of the forces and/or torques of the external force $F_{ext}$ (and/or other forces and/or torques) such that the tool 104 is ultimately moved in a way that provides the user with haptic interaction effects which indicate the direction/rotation in which the tool 104 needs to be moved in order to reach the target state ST. Thus, the guided-haptic mode relies on manual manipulation to move the tool 104, but such movement, instead of merely emulating the movement that would have occurred based on the forces and torques applied by the user, is actively controlled so as to guide the user toward the target state ST. Therefore, the guided-haptic mode allows direct user engagement with the tool 104 while affording the benefits associated with autonomous (or semi-autonomous) movement of the tool 104.

In the guided-haptic mode, the tool 104 is effectively attracted toward the target state ST to provide haptic interaction effects to the user. These effects may be generated in one or more degrees of freedom DOF to attract the tool 104 toward the target state ST. Thus, the target state ST may be defined such that the tool 104 is being attracted in only one degree of freedom DOF, or may be defined such that the tool 104 is being attracted in more than one degree of freedom DOF. Accordingly, the target state ST may comprise a target position PT, target orientation OT, or both (e.g., a target pose TP), defined in a target coordinate system TF. The target position PT may comprise one or more position components with respect to x, y, and/or z axes of the target coordinate system TF (e.g., an x position XP, a y position YP, and/or a z position ZP). In some cases, the target position PT can be represented as the origin of the target coordinate system TF. Similarly, the target orientation OT may comprise one or more orientation components with respect to the x, y, and/or z axes of the target coordinate system TF (e.g., an x orientation XO, a y orientation YO, and/or a z orientation ZO). The x position XP, the y position YP, the z position ZP, the x orientation XO, the y orientation YO, and the z orientation ZO each represent a respective degree of freedom DOF (e.g., of a coordinate system). In some cases, the target orientation OT can be represented as the orientation of the x, y, and z axes of the target coordinate system TF. The term "target pose" TP means a combination of the one or more position components XP, YP, ZP and the one or more orientation components XO, YO, ZO. In some cases, the target pose TP may comprise a target position PT and target orientation OT in all six degrees of freedom DOF of the target coordinate system TF. In some cases, the target position PT and/or the target orientation OT may also be referred to as starting position and/or starting orientation.

The target coordinate system TF can be any coordinate system in which the target state ST is defined, and the target state ST can be transformed to any other coordinate system desired for monitoring the current state SC of the tool 104 relative to the target state ST of the tool 104. The target state ST can be tracked in a tracker coordinate system, the localizer coordinate system LCLZ, the manipulator coordinate system MNPL, the virtual mass coordinate system VM, the tool center point TCP coordinate system, and the like. The target state ST may be defined with respect to an anatomical model AM for the patient P and may be fixed with respect to the anatomy of the patient P in an anatomical model coordinate system, an anatomy tracker coordinate system (e.g., tracked by one or more patient trackers 160A, 160B), and the like. The current state SC of the tool 104 may be defined with respect to a guided coordinate system GF. The guided coordinate system GF may be tied to another coordinate system, or the current state SC may be transformed to any the guided coordinate system GF to enable tracking of the current state SC relative to the target state ST. For example, the current state SC can be tracked in a tracker coordinate system, the localizer coordinate system LCLZ, the manipulator coordinate system MNPL, the virtual mass coordinate system VM, the tool center point TCP coordinate system, and the like. In some of the embodiments, the current state SC of the tool 104 may initially be defined by to the tool center point TCP coordinate system (e.g., where the TCP coordinate system and the guided coordinate system GF are shown as being the same for illustrative purposes) and the target state ST may initially be defined with respect to an anatomical model coordinate system, but both the guided coordinate system GF and the target coordinate system TF can be transformed to a common coordinate system for tracking purposes. The target state ST may be defined pre-operatively, intraoperatively, or both. Various aspects of intraoperative planning, anatomical models, and the like are described in U.S. Patent Application Publication No. US 2018/0333207 A1, entitled "Surgical Systems and Methods for Facilitating Ad-hoc Intraoperative Planning of Surgical Procedures," the disclosure of which is hereby incorporated by reference in its entirety. Other configurations are contemplated.

The control system 124 employs virtual constraints VC that are defined to yield the virtual attractive forces VF (e.g., forces and/or torques) employed in the virtual simulation VS that attract the tool 104 to the target state ST. These virtual constraints VC are referred to herein as guide constraints GC. The guide constraints GC are defined to ultimately influence movement of the tool 104 toward the target state ST so that the user is provided with one or more of the haptic interaction effects described above. Generally, virtual constraints VC are restrictions on the motion of rigid bodies that are considered by the control system 124, along with other motion-related information, to determine how to command the manipulator 102 to move the tool 104. The guide constraints GC, as described further below, have configurable spring parameters PS and damping parameters PD so that the guide constraints GC are not infinitely stiff. More specifically, in some versions, the guide constraints GC are defined as "soft constraints" such that they do not prevent motion that violates them, such as motion resulting from forces and torques applied by the user in opposite directions to the target state ST. Thus, in the guided-haptic mode or other modes, the user may still be able to influence motion of the tool 104 into a direction opposing the target state ST, in violation of the guide constraints GC, yet the guide constraints GC still act to generate attractive forces and torques opposing the user that the user feels (e.g., haptic interaction effects) so that the user knows which direction the tool 104 should be moved to reach the target state ST. For example, the user may feel these haptic interaction effects by virtue of the ease in which the tool 104 may be moved toward the target state ST, as compared to moving away from the target state ST (e.g., the user may feel as though more work is needed to move the tool 104 away from the target state ST as compared to moving toward the target state ST). In other words, it may feel to the user as though a physical spring interconnects the guided coordinate system GF of the tool 104 with the target coordinate system TF (see illustration of spring and damper in FIG. 6).

One or more guide constraints GC may be used by the control system 124 to guide the user, including up to three guide constraints GC associated with the target position PT and up to three guide constraints GC associated with the target orientation OT. As described in greater detail below, the control system 124 operates to calculate the constraint force $F_c$ that satisfies the guide constraints GC (and other virtual constraints VC, if used). The constraint force $F_c$ incorporates the virtual attractive forces VF (e.g., forces and/or torques) therein to attract the tool 104 to the target state ST. Each of the guide constraints GC are considered one-dimensional, virtual constraints VC. In some embodiments, the guide constraints GC are velocity impulse constraints. In some embodiments, the constraints are similar to those used in the impulse modeling described in U.S. Pat. No. 9,119,655, entitled "Surgical Manipulator Capable of Controlling a Surgical Instrument in Multiple Modes," previously referenced. In some embodiments, these virtual constraints VC are defined exclusively in the guided-haptic mode, and not in the manual mode or the semi-autonomous mode. In some embodiments, virtual constraints VC are used in all modes. Other configurations are contemplated.

Figure 6:
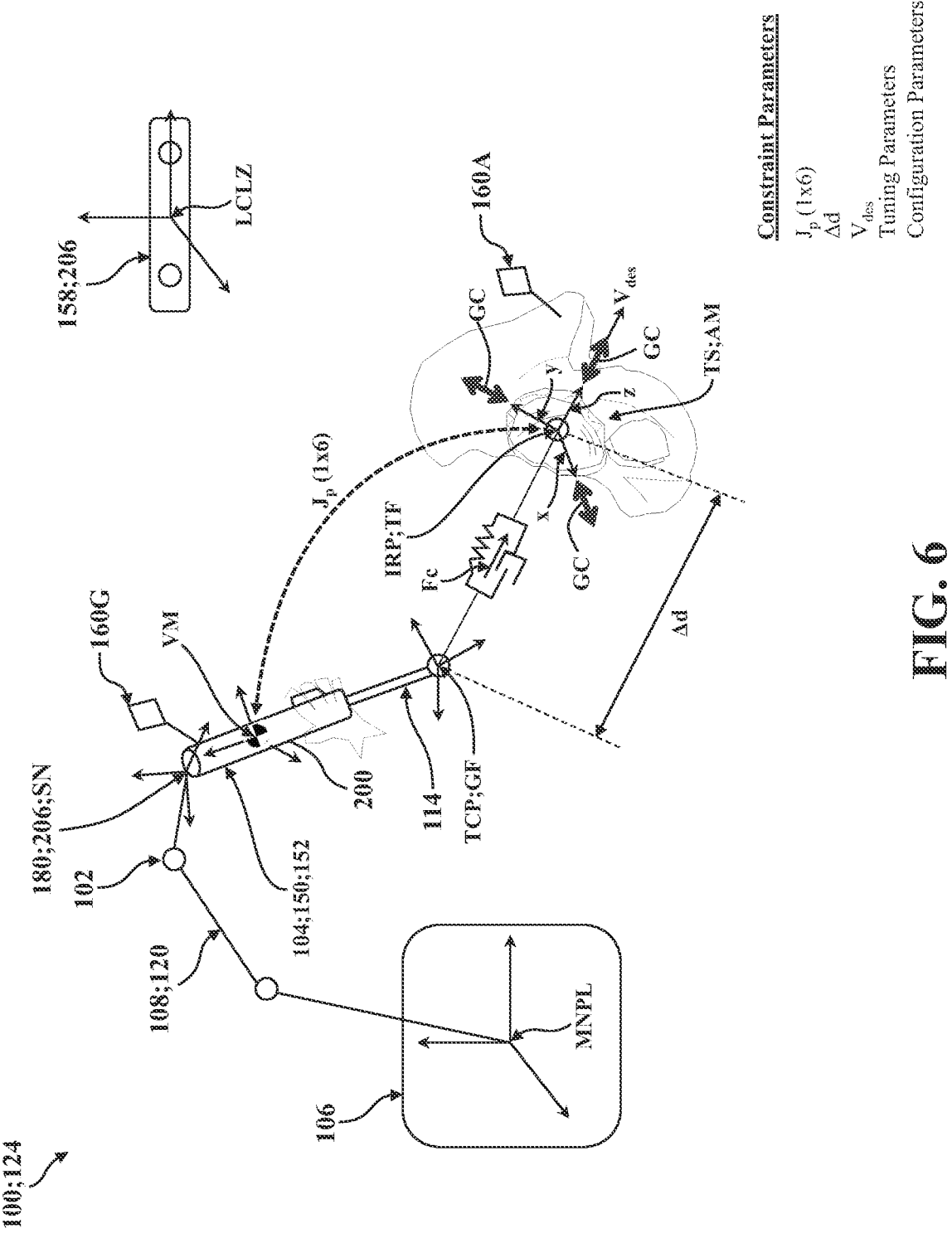
FIG. 6 is an illustrative view of a target site and one of the tools of FIG. 1, depicting virtual constraints of the surgical system.

In FIG. 6, three guide constraints GC associated with a target position PT are illustratively represented as being defined in the target coordinate system TF. The constraint force $F_c$ that is ultimately calculated as a result of these three guide constraints GC is illustrated as comprising an attractive force that incorporates spring parameters PS and damping parameters PD that guides the tool center point TCP of the tool 104 to the target position PT (e.g., to the origin of the target coordinate system TF). This is merely one example. The constraint force $F_c$ may comprise components of force and torque to also align the tool 104 with a target orientation.

The guide constraints GC (and other virtual constraints VC, if used) are defined primarily by three runtime parameters: a constraint Jacobian Jp, a desired velocity $V_{des}$ (or Vp2), and a constraint distance Δd. The Jacobian Jp maps each one-dimensional, guide constraint GC to a coordinate system employed for the virtual simulation VS (e.g., the virtual mass coordinate system VM). The desired velocity $V_{des}$ (or Vp2) is a scalar velocity of the guide constraint GC in the target coordinate system TF. Here, the desired velocity $V_{des}$ may be zero when the patient P is immobile and the associated target state ST defined relative to the patient P is not moving, but may not be zero when the patient P moves since the target state ST may be tied to the patient P. The constraint distance Δd refers to how close the guided coordinate system GF is to the constraint and dictates whether the constraint is being violated. In some cases, Δd refers to a distance/angle of the current state SC from the target state ST, and a guide constraint GC is violated any time the current state SC does not match the target state ST for the associated degree of freedom.

The guide constraints GC are not perfectly rigid, but instead each of the guide constraints GC has tuning parameters TPA to adjust the stiffness of the virtual constraints VC (e.g., by incorporating spring parameters PS and/or damping parameters PD). Such tuning parameters TPA may include a constraint force mixing parameter C and an error reduction parameter E. The spring parameters PS and damping parameters PD may be adjusted during operation in the guided-haptic mode, or during other modes as described in greater detail below. In some embodiments, values for the tuning parameters TPA may change based on a relationship between the current state SC and the target state ST. For example, the tuning parameters TPA may be configured to increase in stiffness the closer the tool 104 gets to the target state ST, or the tuning parameters TPA may decrease in stiffness as the tool 104 approaches the target state ST. The tuning parameters TPA may be different for different guide constraints GC. For example, the guide constraints GC may comprise a first virtual constraint VC that has a first value for a tuning parameter TP1 and a second virtual constraint VC that has a second value for the tuning parameter TPA, the first value being greater than the second value so that the resulting virtual attractive force VF (e.g., forces and/or torques) embodied in the constraint force $F_c$ is adapted to attract the tool 104 more strongly as a result of the first virtual constraint VC as compared the second virtual constraint VC. The values of the tuning parameters TPA may be greater (e.g., stiffer) for position constraints than for orientation constraints, or vice versa. Other configurations are contemplated.

The tuning parameters TPA may also be set to: remain constant regardless of the distance/angle from the current state SC to the target state ST; rise/fall exponentially with distance between the current state SC to the target state ST; vary linearly with distance between the current state SC and the target state ST; vary with constraint direction; take gravitational effects into account; and the like. A tuning parameter TPA for one virtual constraint VC associated with one degree of freedom DOF may be set based on a relationship associated with another degree of freedom DOF (e.g., the stiffness of an x-axis constraint may change based on the distance along the y-axis between the current state SC and the target state ST). The tuning parameters TPA may also vary depending on the direction in which the tool 104 needs to move in order to reach the target state ST (e.g., more stiff when moving in one direction along the x-axis when compared to the opposite direction along the x-axis). The tuning parameters TPA can also be scaled depending on the constraint force $F_c$ that is ultimately computed based on the guide constraints GC, such as by increasing/decreasing the stiffness depending on the magnitude of the constraint force $F_c$, or any components thereof. Fixed values for one or more virtual attractive forces VF could also be added into the virtual simulation VS in some cases.

The tuning parameters TPA for the guide constraints GC may be set so that the user can easily cause the tool 104 to move away from the target position PT and/or target orientation OT. In other words, the tuning parameters TPA may be set so that, in the virtual simulation VS, the influence of the forces and torques applied by the user may outweigh the influence of the virtual attractive forces VF (e.g., forces and torques). Thus, the control system 124 may be configured to enable the user to reposition and/or reorient the tool 104 away from the target position PT and/or the target orientation OT even when the guide constraints GC are enabled. The tuning parameters TPA for the guide constraints GC may be set preoperatively or intraoperatively, may be updated intraoperatively, or combinations thereof. The tuning parameters TPA and their values, their correlation to a particular relationship, and the manner in which they may be scaled, could be stored in one or more look-up tables in any suitable memory 140 of the control system 124 for later retrieval.

Each guide constraint GC also has configuration parameters CPA. The configuration parameters CPA may comprise: information regarding the tuning parameters TPA such as the constraint force mixing parameter C and the error reduction parameter E; upper force limits FLU and/or lower force limits FLL; and/or upper constraint distance offsets DOU and/or lower constraint distance offsets DOL. The upper and lower force limits FLU, FLO refer to limits on the forces computed for each guide constraint GC that are ultimately solved by the constraint solver 192 to produce the constraint force $F_c$, as described further below. The guide constraints GC are two-sided constraints (e.g., the forces computed to satisfy the constraints can be positive or negative), the force limits FLU, FLO can be set high in positive and negative directions (e.g., $-100,000/+100,000$ Newtons) or at any desired limit. The upper and lower constraint distance offsets DOU, DOL dictate when the constraint is active. With respect to the guide constraints GC, the upper and lower constraint distance offsets DOU, DOL can be set so that the constraint is active any time the current state SC is different than the target state ST.

Figure 7:
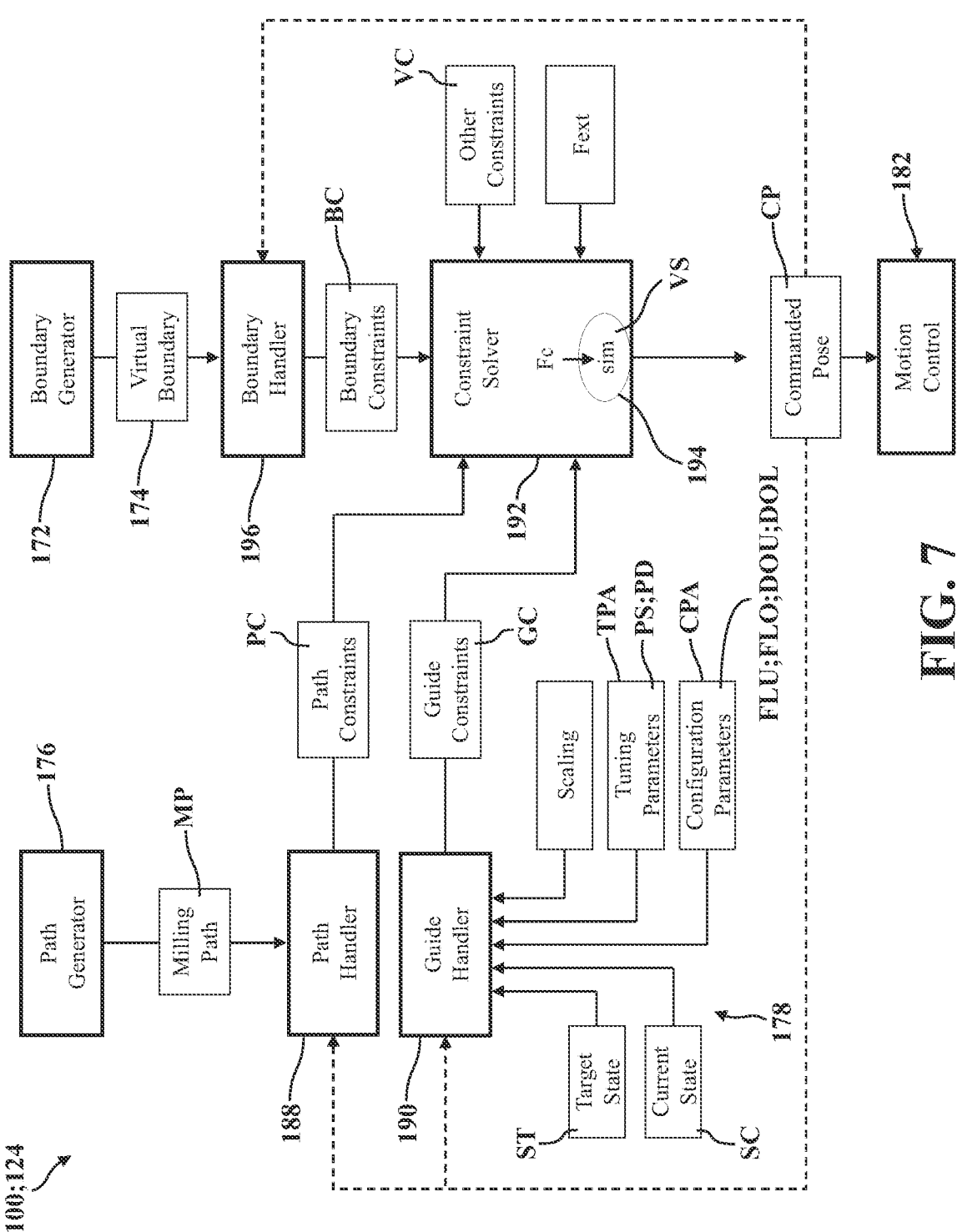
FIG. 7 is a block diagram of modules operable by the control system of FIG. 2.

FIG. 7 illustrates processes carried out to execute the guided-haptic mode in some embodiments. Here, the behavior control 178 comprises a path handler 188, a guide handler 190, a constraint solver 192, and a virtual simulator 194. The behavior control 178 further comprises a boundary handler 196 to generate virtual boundary constraints BC based on the one or more virtual boundaries 174 generated by the boundary generator 172. The path handler 188, guide handler 190, constraint solver 192, virtual simulator 194, and boundary handler 196 each comprise executable software stored in a non-transitory memory 140 of any one or more of the aforementioned controllers 132, 134, 136 and implemented by the control system 124. Each of the portions of the behavior control 178 introduced above will be described in greater detail below.

The guide handler 190 obtains the target state ST for the tool 104 and generates one or more guide constraints GC based on the target state ST and the current state SC of the tool 104. As shown in FIG. 7, two inputs into the guide handler 190 comprise the current state SC and the target state ST. The current state SC may be defined with respect to the last commanded pose CP, since the last commanded pose CP correlates to the current pose of the tool 104. The target state ST may be defined in the anatomical coordinate system, anatomy tracker coordinate system, and the like, and transformed to a common coordinate system with the current state SC. Other inputs into the guide handler 190 comprise the configuration parameters CPA and tuning parameters TPA for the guide constraints GC. The guide handler 190 defines the one or more guide constraints GC based on the relationship between the currents state SC and the target state ST, and the configuration parameters CPA and the tuning parameters TPA. The guide constraints GC are output from the guide handler 190 into the constraint solver 192.

Various virtual constraints VC may be fed into the constraint solver 192, including guide constraints GC, path constraints PC, boundary constraints BC, and other constraints. These virtual constraints VC may be turned on/off by the control system 124. For example, in some cases, there may be no path constraints PC, no boundary constraints BC, and no other constraints being generated. Similarly, there may be no guide constraints GC being generated in some instances, and in certain modes of operation. All of the virtual constraints VC employed in the behavior control 178 may affect movement of the tool 104. For purposes of illustration, only the guide constraints GC will be described in detail.

The constraint solver 192 calculates the constraint force $F_c$ to be virtually applied to the tool 104 in the virtual simulator 194 based on the virtual constraints VC fed into the constraint solver 192. In the guided-haptic mode, the constraint force $F_c$ comprises components of force and/or torque adapted to attract the tool 104 toward the target state ST from the current state SC based on the one or more guide constraints GC. In cases where only the guide constraints GC are input into the constraint solver 192, the constraint force $F_c$ can be considered to be the virtual attractive force VF described above. However, when other virtual constraints VC are employed, the constraint solver 192 is ultimately tasked with providing a solution for the constraint force Fc that satisfies all of the virtual constraints VC, and thus other virtual constraints VC may also influence the magnitude/direction of the constraint force $F_c$. In those cases, the virtual attractive forces VF (e.g., forces and/or torques) are considered those force and torque components of the constraint force $F_c$ that are directed toward the target state ST as a result of the guide constraints GC.

Referring to the constraint equation CEQ shown in FIG. 8, the constraint solver 192 places the constraint data for each virtual constraint VC into a corresponding row of a constraint equation CEQ, in matrix form, to solve for $F_p$. Here, $F_p$ is a force vector in the target coordinate system TF, whereby each component of $F_p$ is a scalar constraint force acting in the corresponding constraint direction. In order to solve for $F_p$, as described in greater detail below, the equation shown in FIG. 8 is converted into a matrix equation where each row represents a single, one-dimensional virtual constraint VC. The constraint data are placed in the constraint equation CEQ, along with other information known by the constraint solver 192 such as the external force $F_{cgext}$, a damping force $F_{damping}$, an inertial force $F_{inertial}$, a virtual mass matrix M, a virtual mass velocity $V_{cg1}$, and the time step $\Delta t$ (e.g., 125 microseconds).

The virtual mass matrix M combines 3×3 mass and inertia matrices. The damping and inertial forces $F_{damping}$ and $F_{inertial}$ are calculated or otherwise known by the virtual simulator 194 and are based on the virtual mass velocity $V_{cg1}$ (e.g., the velocity of the virtual mass coordinate system VM) output by the virtual simulator 194 in a prior time step. The virtual mass velocity $V_{cg1}$ is a six degree of freedom DOF velocity vector comprising linear and angular velocity components. The damping force $F_{damping}$ is a six degree of freedom DOF force/torque vector computed as a function of the virtual mass velocity $V_{cg1}$ and a damping coefficient matrix (linear and rotational coefficients may not be equal). Damping is applied to the virtual mass to improve its stability. The inertial force $F_{inertial}$ is also a six degree of freedom DOF force/torque vector computed as a function of the virtual mass velocity $V_{cg1}$ and the virtual mass matrix M. The damping and inertial forces, $F_{damping}$ and $F_{inertial}$, can be determined in the manner described in U.S. Pat. No. 9,566, 122, entitled "Robotic System and Method for Transitioning Between Operating Modes," the disclosure of which is hereby incorporated herein by reference in its entirety.

The constraint solver 192 may be configured with any suitable algorithmic instructions (e.g., an iterative constraint solver, a Projected Gauss-Seidel solver, and the like) to solve the system of constraint equations CEQ in order to provide a solution which best satisfies the system of equations (e.g., best satisfying the various virtual constraints VC). In some cases, all virtual constraints VC may not simultaneously be met. For example, in the case where motion is over-constrained by the various virtual constraints VC, the constraint solver 192 will essentially find a "best fit" solution given the relative stiffness/damping of the various virtual constraints VC. The constraint solver 192 solves the system of equations and ultimately outputs the constraint force $F_c$.

When a Projected Gauss-Seidel solver is employed, the constraint solver 192 constructs A and b matrices based on the virtual constraints VC, and uses Projected Gauss-Seidel to solve the system of equations to determine the resulting force vector $F_p$. The constraint solver 192 then takes the output of Projected Gauss-Seidel and transforms it from the target coordinate system TF (e.g., the constraint coordinate system) to the virtual mass coordinate system VM. For example, using the equation $F_c = J_p^T F_p$, wherein $F_c$ is the constraint force, each resulting force vector $F_p$ is converted to a force/torque vector applied to the virtual mass coordinate system VM.

Methods of using Project Gauss-Seidel to solve a system of equations for multiple constraints is shown, for example, in "Constraint based physics solver" by Marijn Tamis and Giuseppe Maggiore, dated Jun. 15, 2015 (v1.02), which can be found at http://www.mft-spirit.nl/files/MTamis_ConstraintBasedPhysicsSolver.pdf; or in "Comparison between Projected Gauss-Seidel and Sequential Impulse Solvers for Real-Time Physics Simulations," by Marijn Tamis, dated Jul. 1, 2015 (v1.01), which can be found at http://www.mft-spirit.nl/files/MTamis_PGS_SI_Comparison.pdf; both of which are hereby incorporated herein by reference in their entirety.

The Projected Gauss-Seidel method addresses Linear Complementarity Problems LCP. Inequality associated with LCP arises since some constraint types (e.g., one-sided virtual constraints VC such as the boundary constraints BC) can only push or "apply force" in one direction (e.g., positive constraint force). If the calculated force for such a virtual constraint VC is negative (or, more broadly, is outside of its allowed range) for a given iteration of the constraint solver 192, which is invalid, the given virtual constraint VC must be pruned (or alternately limited/capped at its upper or lower allowed value FLU, FLO) and the remaining virtual constraints VC solved until a suitable result (e.g., convergence) is found. In this manner, the constraint solver 192 determines the active set of virtual constraints VC for a given time step, and then solves for their values. Other virtual constraint VC types can apply forces in both positive and negative directions (e.g., two-sided virtual constraints VC). Such virtual constraints VC include the guide constraints GC used to guide the user into moving the tool 104 toward the target state ST. Such two-sided virtual constraints VC, when enabled, are usually active and not pruned/limited during the constraint solver 192 iterations.

The constraint force $F_c$ calculated by the constraint solver 192 comprises three components of force along x, y, z axes and three components of torque about the x, y, z axes. The virtual simulator 194 utilizes the constraint force $F_c$, along with the external force $F_{cgext}$, the damping force $F_{damping}$, and the inertial force $F_{inertial}$ (all of which may comprise six components of force/torque), in its virtual simulation VS. In some cases, these components of force/torque are first transformed into a common coordinate system (e.g., the virtual mass coordinate system VM) and are then summed to define a total force $F_T$. The resulting six degree of freedom DOF force (e.g., force and torque) is applied to the virtual rigid body VRB and the resulting motion is calculated by the virtual simulator 194. The virtual simulator 194 thus acts to effectively simulate, among other things, how the various virtual constraints VC affect motion of the virtual rigid body VRB. The virtual simulator 194 performs forward dynamics to calculate the resulting six degree of freedom DOF pose and velocity of the virtual rigid body VRB based on the given total force $F_T$ being applied to the virtual rigid body VRB. In some embodiments, the virtual simulator 194 comprises a physics engine realized as executable software stored in a non-transitory memory 140 of any one or more of the aforementioned controllers 132, 134, 136 and implemented by the control system 124.

For the virtual simulation VS, the virtual simulator 194 models the tool 104 as the virtual rigid body VRB in the virtual mass coordinate system VM, with the origin of the virtual mass coordinate system VM being located at the center of mass of the virtual rigid body VRB, and with the coordinate axes being aligned with the principal axes of the virtual rigid body VRB. The virtual rigid body VRB is a dynamic object and a rigid body representation of the tool 104 for purposes of the virtual simulation VS. The virtual rigid body VRB is free to move according to six degrees of freedom DOF in Cartesian space according to the virtual simulation VS. The virtual simulation VS may be processed computationally without visual or graphical representations. Thus, it is not required that the virtual simulation VS display dynamics of the virtual rigid body VRB. In other words, the virtual rigid body VRB need not be modeled within a graphics application executed on a processing unit. The virtual rigid body VRB may exist only for the virtual simulation VS. However, other configurations are contemplated.

The virtual rigid body VRB and its properties (e.g., mass, inertia matrix, center of mass, principal axes, and the like) define how the tool 104 will move in response to applied forces and torques (e.g., from the total force $F_T$, which incorporates forces and torques applied by the user and virtual attractive forces VF and/or torques). The virtual rigid body VRB governs whether the tool 104 will feel heavy or light and how it will move (e.g., accelerate in translation and/or rotation) in response to applied forces and torques. By adjusting the properties of the virtual rigid body VRB, the control system 124 can adjust how the tool 104 feels to the user. It may be desirable to have the properties of the virtual rigid body VRB modeled so as to be reasonably close to the actual properties of the tool 104, such as to afford motion/feel that is as realistic as possible, but that is not required. For control stability reasons (e.g., given the finite acceleration of the manipulator, control latencies, and the like), the virtual mass and inertia may be modeled to be somewhat higher than that of the physical tool 104.

The virtual rigid body VRB may correspond to components which may be on or within the tool 104. Additionally, or alternatively, the virtual rigid body VRB may extend, in part, beyond the physical tool 104. The virtual rigid body VRB may consider the tool 104 with the energy applicator 114, or may consider the tool 104 without the energy applicator 114. Furthermore, the virtual rigid body VRB may be based on the tool center point TCP. In one example, the center of mass of the virtual rigid body VRB is understood to be the point around which the virtual rigid body VRB would rotate if a virtual force were applied to another point of the virtual rigid body VRB and the virtual rigid body VRB were otherwise unconstrained (e.g., not constrained by the manipulator 102). The center of mass of the virtual rigid body VRB may be close to, but need not be the same as, the actual center of mass of the tool 104. The center of mass of the virtual rigid body VRB can be determined empirically. Once the tool 104 is attached to the manipulator

102, the position of the center of mass can be reset to accommodate the preferences of the individual users.

The virtual simulator 194 effectively simulates rigid body dynamics of the tool 104 by virtually applying forces and/or torques on the virtual rigid body VRB in the virtual simulation VS, such as by virtually applying the components of force and torque from the total force $F_T$ on the center of mass of the virtual rigid body VRB in the virtual mass coordinate system VM. Thus, the forces/torques virtually applied to the virtual rigid body VRB may comprise forces/torques associated with the external force $F_{cgext}$ (e.g., based on input from one or more sensors 180), the damping force $F_{damping}$, the inertial force $F_{inertial}$, and the forces/torques from the constraint force $F_c$ associated with the various virtual constraints VC (by virtue of being embodied in the constraint force $F_c$).

Rigid body Jacobians can be used to transform velocities and forces from one coordinate system (or "reference frame") to another on the same virtual rigid body VRB, and may be employed here to transform the forces and torques of the external force $F_{ext}$ to the virtual mass coordinate system VM (e.g., to yield the external force $F_{cgext}$ used in the constraint equation CEQ). The virtual simulator 194 then internally calculates the damping force $F_{damping}$ and the inertial force $F_{inertial}$ to determine the total force $F_T$, and also to output the damping force $F_{damping}$ and the inertial force $F_{inertial}$ for use by the constraint solver 192 in its system of equations in the next time step.

A virtual forward dynamics algorithm VFA, as shown in FIGS. 9 and 10, may be employed in the virtual simulation VS to simulate the motion of the virtual rigid body VRB as it would move upon application of the total force $F_T$. Effectively, the virtual forward dynamics algorithm VFA solves the equation F=ma (or a=F/M) in six degrees of freedom DOF and integrates the acceleration to yield velocity, which is then used to determine a new pose, as shown in FIG. 10. The control system 124 inputs the virtual forces and/or torques (e.g., the total force $F_T$) into the virtual simulator 194 and these virtual forces and/or torques are applied to the virtual rigid body VRB at the center of mass (e.g., the CG) in the virtual simulation VS when the virtual rigid body VRB is in the initial pose with the initial velocity. The virtual rigid body VRB is moved to a final pose having a different state (e.g., position and/or orientation) and with a final velocity within Cartesian space in response to the control system 124 satisfying the inputted virtual forces and/or torques. The next commanded pose CP to be sent to the motion control 182 is based on the final pose calculated by the virtual simulator 194. Thus, the virtual simulator 194 operates to determine the next commanded pose CP by simulating the effects of applying the total force $F_T$ on the virtual rigid body VRB using virtual forward dynamics as shown in FIG. 10.

Velocity limits VL may be imposed on the virtual rigid body VRB in the virtual simulation VS. In some cases, the velocity limits VL may be set high so that they generally don't affect the virtual simulation VS, or they may be set at any desired value. The virtual rigid body VRB is in an initial pose (e.g., an initial state) and has an initial velocity at commencement of each iteration of the virtual simulation VS (e.g., at each time step/interval dt). The initial pose and the initial velocity may be defined as the final pose and the final velocity output by the virtual simulator 194 in the previous time step.

Ultimately, the virtual simulator 194 calculates and outputs the next commanded pose CP based on its virtual simulation VS. The control system 124 is configured to command the manipulator 102 to move the tool 104 based on the commanded pose CP, which ideally causes movement of the tool 104 in a manner that guides the user into placing the tool 104 at the target state ST by providing haptic feedback to the user that guides the user toward placing the tool 104 at the target state ST. Thus, the user is able to manually manipulate the tool 104, while the control system 124 assists in guiding the tool movement, by utilizing the guide constraints GC. The forces and torques applied to the tool 104 by the user (e.g., detected by the sensor 180) may still influence the overall movement of the tool 104 because the external force $F_{ext}$ is combined with the constraint force $F_c$ before running the virtual simulation VS to determine the commanded pose CP. In some instances (e.g., time steps), the total force $F_T$ includes components of force and torque form the external force $F_{ext}$ with magnitude and direction sufficient to overcome the forces and torques of the constraint force $F_c$ such that the tool 104 is movable away from the target state ST. However, as noted above, the guide constraints GC have configurable stiffness and damping (e.g., based on the spring parameters PS and the damping parameters PD) that can be tuned such that the external force $F_{ext}$ has less influence in certain situations.

Figure 11:
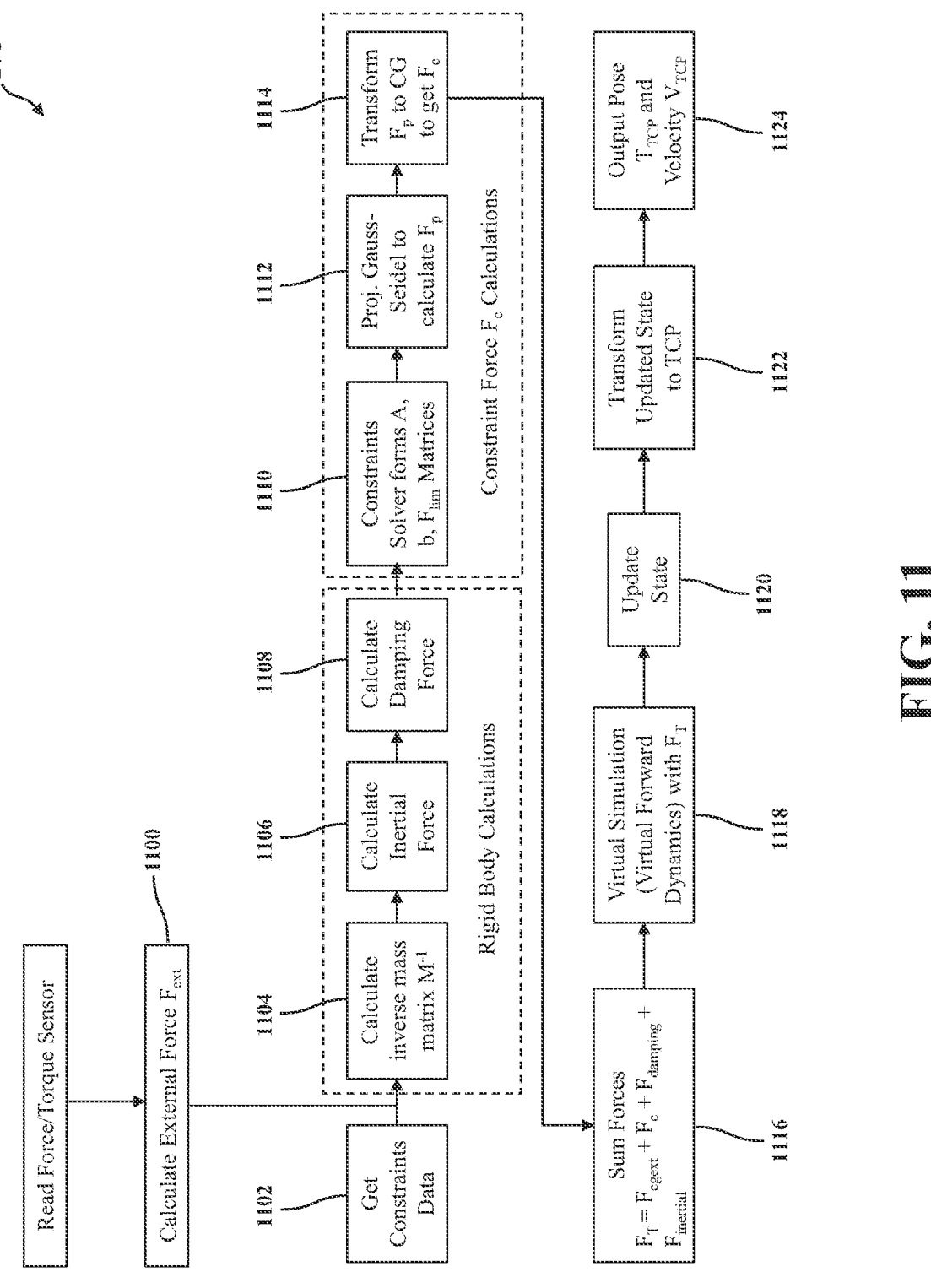
FIG. 11 depicts an exemplary set of steps carried out by the control system of FIG. 2 to solve constraints, perform forward dynamics, and determine a commanded pose.

FIG. 11 summarizes various steps carried out by the behavior control 178. These include steps performed by the constraint solver 192 and the virtual simulator 194 as described above. In step 1100, the external force $F_{ext}$ is calculated based on readings taken from the sensor 180. In step 1102, the constraints data associated with the various virtual constraints VC are fed into the constraint solver 192 from the path handler 188, from the guide handler 190, from the boundary handler 196, and/or from other constraint sources.

In steps 1104-1108, rigid body calculations are carried out by the virtual simulator 194 to determine the inverse mass matrix $M^{-1}$, the inertial force $F_{inertial}$, and the damping force $F_{damping}$ of the virtual rigid body VRB. In steps 1110-1114, the constraint solver 192 utilizes the output from the rigid body calculations performed in steps 1104-1108 and the constraints data provided in step 1102 to perform the constraint force calculations previously described to ultimately yield the constraint force $F_c$. In step 1116, the constraint force $F_c$ is summed with the external force $F_{ext}$ transformed to the virtual mass coordinate system VM ($F_{cgext}$), the damping force $F_{damping}$, and the inertial force $F_{inertial}$ to yield the total force $F_T$. In step 1118, the total force $F_T$ is applied to the virtual rigid body VRB in the virtual simulation VS conducted by the virtual simulator 194 to determine a new pose and velocity of the virtual rigid body VRB in step 1120, and ultimately to transform the new pose and velocity to the tool center point TCP in step 1122. The new commanded pose CP (TTCP) and velocity ($V_{TCP}$) are output by the virtual simulator 194 in step 1124.

Figure 12:
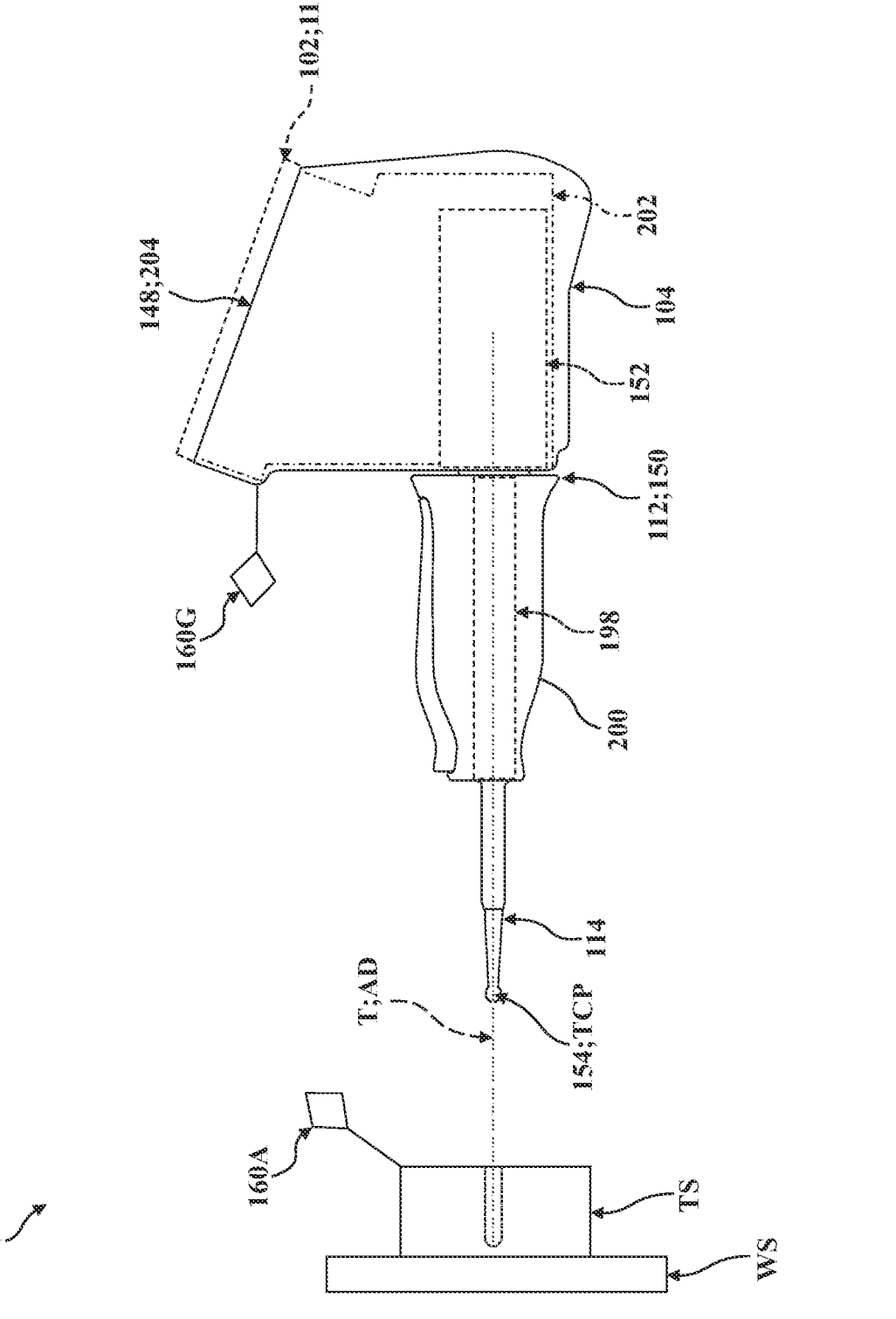
FIG. 12 is an illustrative schematic view of the tool of FIG. 1 shown supporting the energy applicator along an axis aligned with the trajectory of the target site, and shown with the energy applicator spaced from the target site.

Referring now to FIG. 12, portions of the surgical system 100, including one of the tools 104 of FIG. 1, and a generically-depicted target site TS are shown schematically, with the target site TS shown supported on a work surface WS such as a surgical table (not shown in detail). Here, the target site TS represents a portion of the anatomy of the patient P, such as a bone or another type of tissue, that is to be treated during a surgical procedure. To this end, the tool 104 is shown spaced from the target site TS along the trajectory T which, as noted above, is monitored or otherwise known by the navigation system 128 from tracked states of the first patient tracker 160A secured to the target site TS. For illustrative purposes, the first tool tracker 160G is shown firmly fixed to the tool 104. However, while the navigation system 128 can track states of multiple trackers 160 within a common coordinate system as noted above, the pose of a tracked object (e.g., the tool 104) can be determined in other ways (e.g., based on known geometric relationships) and transformed between coordinate systems (e.g., between the manipulator coordinate system MNPL and the localizer coordinate system LCLZ). Put differently, the surgical system 100 can determine changes in the pose of the tool 104 relative to the first patient tracker 160A without necessarily utilizing the illustrated first tool tracker 160G because, among other things, the geometry of the tool 104 and the energy applicator 114 are known.

In this representative example, the tool 104 similarly comprises the mount 148 (depicted in phantom) to facilitate releasable attachment to the coupling 110 of the manipulator 102, and the instrument 112 is realized as a powered surgical device 150 with a power generation assembly 152 (depicted in phantom) that is driven by the tool controller 136 or another part of the control system 124. Here, the power generation assembly 152 is realized as an electric motor configured to selectively generate rotational torque about a drive axis AD to drive one or more types of energy applicators 114. To this end, the powered surgical device 150 comprises a chuck assembly 198 (see FIG. 12; depicted in phantom) disposed in rotational communication with the power generation assembly 152 to facilitate releasable attachment of the energy applicator 114 which, in this illustrative embodiment, is realized by the bur 154 (attachment not shown in detail). However, the tool 104, the instrument 112, and/or the energy applicator 114 could be of a number of different configurations without departing from the scope of the present disclosure. Here, the tool 104 comprises a handling region 200 arranged to be grasped by the user, with a trigger that may serve as an input device 146 (e.g., to start and stop rotation of the energy applicator 114). In some embodiments, tool 104 and/or the powered surgical device 150 may be like that shown in U.S. Pat. No. 9,566, 121, entitled "End Effector of a Surgical Robotic Manipulator," previously referenced. In some embodiments, the tool 104 and/or the powered surgical device 150 may be like that shown in U.S. Patent Application Publication No. US 2018/ 0110572 A1, entitled "Systems and Tools for Use With Surgical Robotic Manipulators," the disclosure of which is hereby incorporated by reference in its entirety. Other configurations are contemplated.

With continued reference to FIG. 12, the power generation assembly 152 of the powered surgical device 150 is operatively attached to the mount 148 by a frame 202 (generically depicted in phantom), such as by one or more fasteners (not shown). While the frame 202 is formed separately from the mount 148 in the illustrated embodiment, other configurations are contemplated, and the mount 148 could be formed from or otherwise realized by any suitable number of components sufficient to facilitate coupling to the manipulator 102. Similarly, the frame 202 could similarly be defined by a number of different components which cooperate to support the power generation assembly 152 and other parts of the tool 104. In some embodiments, one or more covers 204 may be employed by tool 104 to conceal, protect, or otherwise shield certain components (e.g., the mount 148) from the outside environment. The covers 204 may also conceal electrical components (e.g., wires, electrical connectors, printed circuit boards, and the like), and may be shaped and arranged to permit access to a sterile interface system (not shown, but generally known in the related art) arranged between the mount 148 and the coupling 110 of the manipulator 102 to facilitate removably attaching the tool 104 to the manipulator 102. Here, releasable attachment of the coupling 110 to the mount 148 could be achieved in a number of different ways sufficient to secure the tool 104 to the manipulator 102.

In FIG. 12, a portion of the target site TS is shown in phantom to depict the intended volume of tissue (e.g., bone) to be removed by the bur 154 along the trajectory T which, for illustrative purposes, serves as the milling path MP in this representative example. Here too, the intended "depth" of tissue removal at the target site TS is represented by a target reference point TRP which, like the tool center point TCP, could be defined as a coordinate system. Here, both the tool center point TCP and the target reference point TRP are shown arranged along the trajectory T.

Figure 13A:
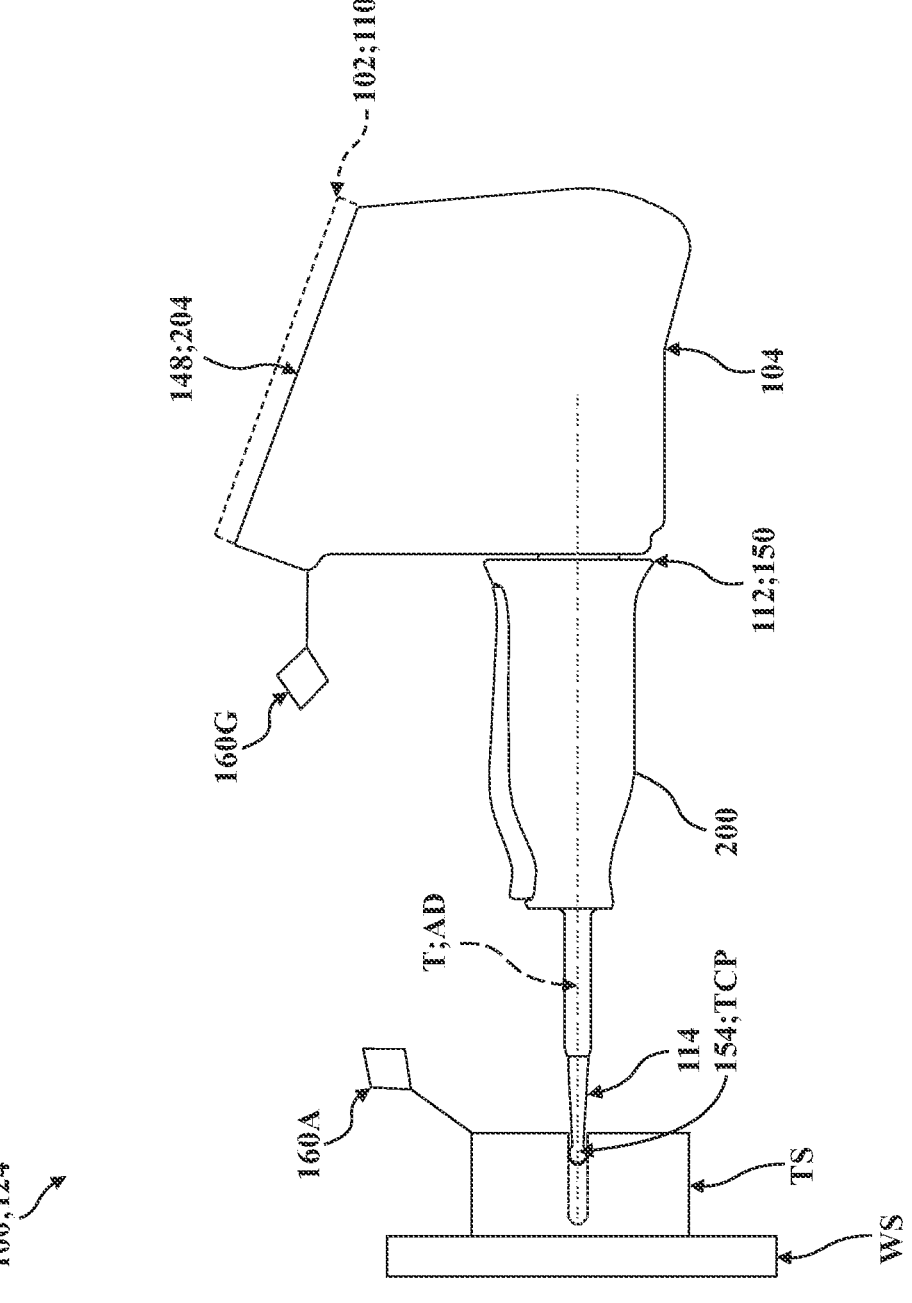
FIG. 13A is another illustrative schematic view of the tool, the energy applicator, and the target site of FIG. 12, shown with the energy applicator engaging the target site along the trajectory.
Figure 13B:
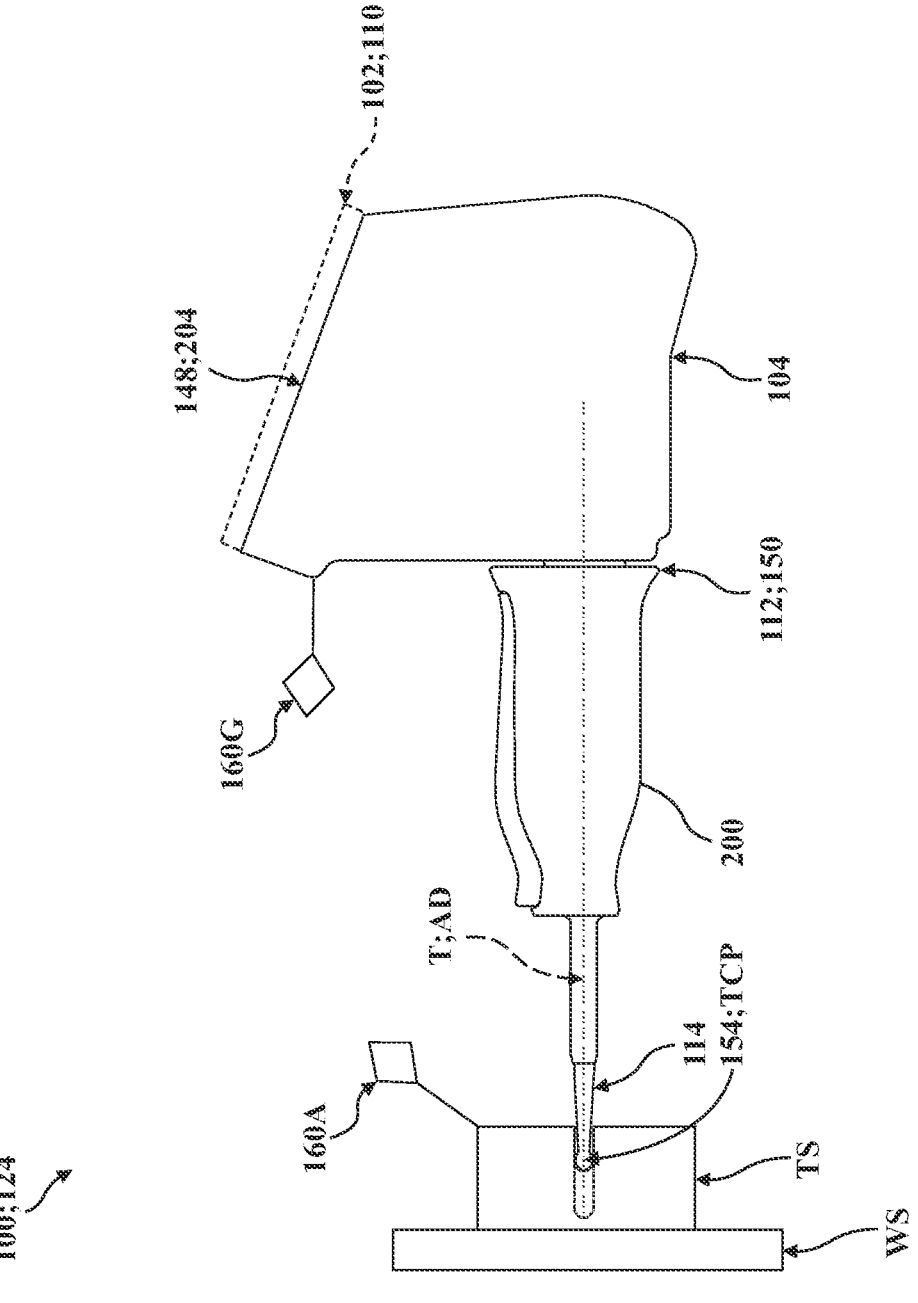
FIG. 13B is another illustrative schematic view of the tool, the energy applicator, and the target site of FIG. 13A, shown with the energy applicator advanced along the trajectory and engaging deeper into the target site.

Continuing to FIG. 13A from FIG. 12, the tool 104 has been advanced along the trajectory T into engagement with the target site TS, such as by operating the manipulator 102 in one or more of the various modes described herein, with the bur 154 of the energy applicator 114 disposed along the trajectory T maintained by the manipulator 102. More specifically, the tool center point TCP of the energy applicator 114 defined by the bur 154 is disposed along the trajectory T, with the energy applicator 114 rotating about the drive axis AD, which is likewise aligned with the trajectory T. Here, the tool center point TCP is spaced from the target reference point TRP to illustrate the remaining volume of tissue (e.g., bone) to be removed by the bur 154 as the tool 104 is advanced along the trajectory T. This is depicted in FIG. 13B, which shows the tool center point TCP arranged closer to the target reference point TRP (compare FIG. 13B with FIG. 13A).

FIGS. 14A-14D sequentially illustrate a hypothetical "runaway" condition of the surgical system 100 which may occur under certain use cases which result in the energy applicator 114 or another part of the tool 104 becoming effectively "attached" to the manipulator 102 such that the target site TS and tool 104 move together in one or more degrees of freedom DOF, either momentarily or for an extended duration. Here, by way of illustrative example, the energy applicator 114 could potentially encounter changes in tissue types or properties, irregularities, or other types of increased resistance caused such as by friction and/or heat, reduced cutting performance, the accumulation of tissue fragments (e.g., "swarf"), and the like, which may be significant enough to interrupt tissue removal and result in the energy applicator 114 becoming "locked" to the tissue at the target site TS, either momentarily or for an extended period. In some cases, the resistance described above can result in the energy applicator 114 being "locked" to tissue at the target site TS off of the trajectory T.

The hypothetical scenario described above may be illustrated by comparing FIGS. 14A-14B. Here, in FIG. 14A, the energy applicator 114 is engaging the target site TS and encounters a significant resistance to rotation about the drive axis AD which brings the tool center point TCP off of the trajectory T maintained by the manipulator 102 and results in the energy applicator 114 becoming "locked" to the target site TS, as is depicted by the exaggerated misalignment between the trajectory T and the drive axis AD illustrated in FIG. 14B. While the target state ST of the tool 104 could be defined in a number of different ways, for illustrative purposes in this representative example, the target state ST includes coincident alignment between the drive axis AD and the trajectory T. However, because the current state SC of the tool 104 shown in FIG. 14B includes misalignment between the drive axis AD and the trajectory T with the energy applicator 114 "locked" to the target site TS, a "runaway" condition may occur as the manipulator 102 attempts to move from the current state SC to the target state ST. The "runaway" condition may also occur as a result of the patient tracker 160 becoming loose from the target site TS thereby causing a loss of tracking accuracy.

Figure 14A:
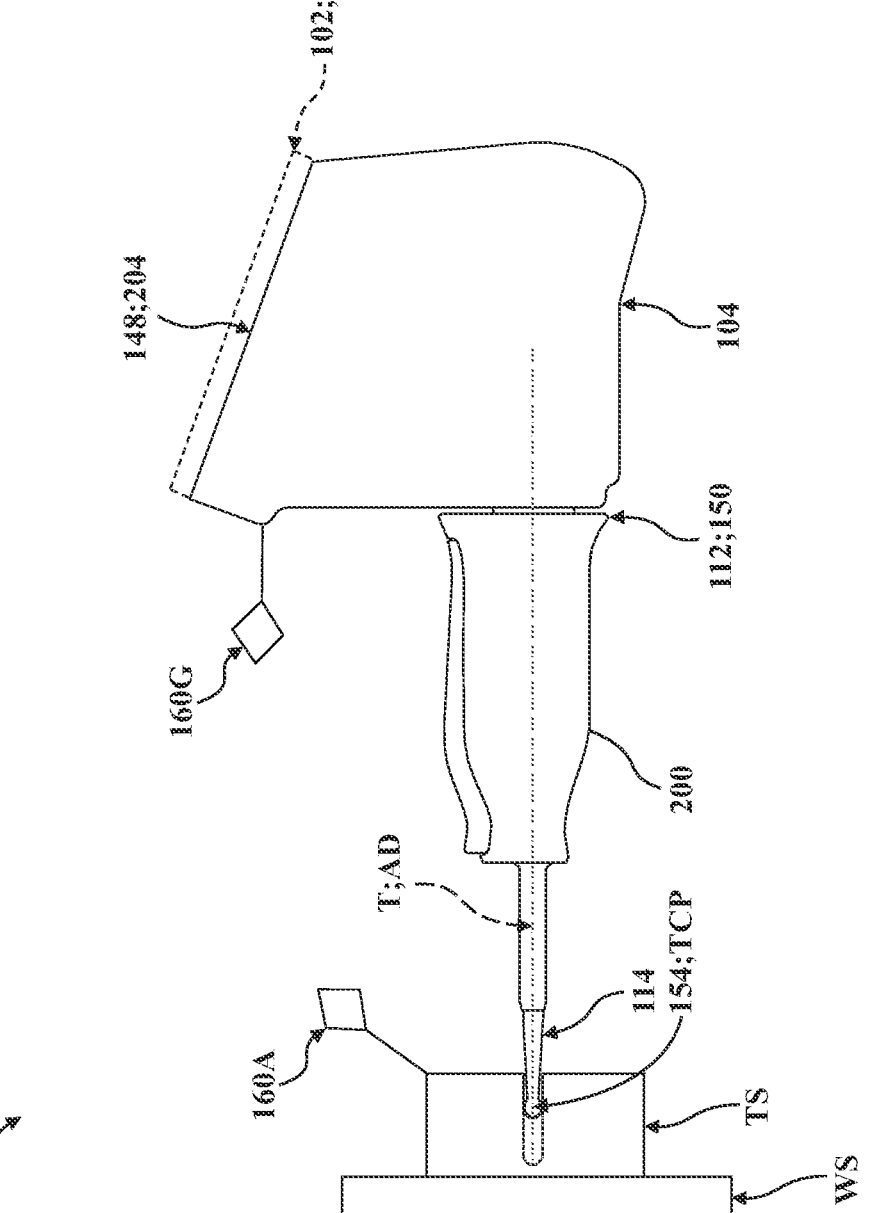
FIG. 14A is another illustrative schematic view of the tool, the energy applicator, and the target site of FIG. 13B, shown with the energy applicator encountering resistance to rotation about the axis while in engagement with the target site.
Figure 14B:
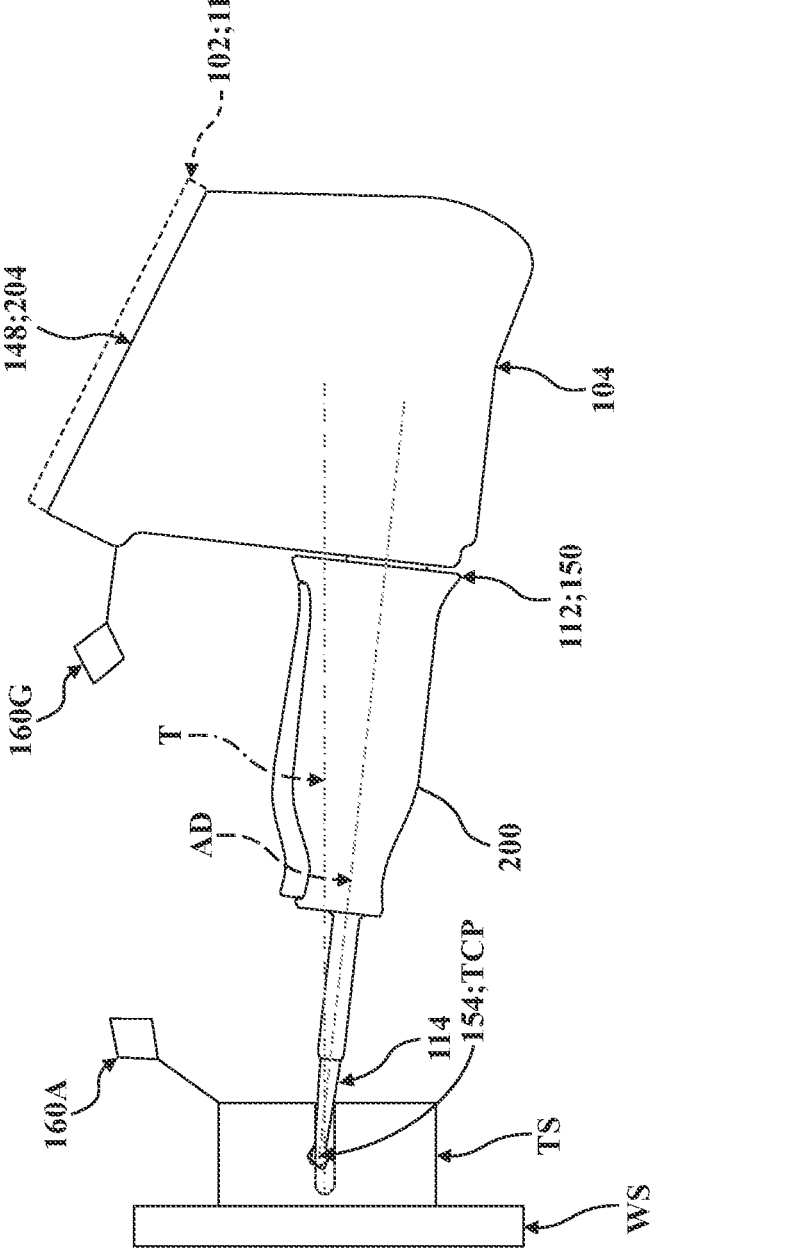
FIG. 14B is another illustrative schematic view of the tool, the energy applicator, and the target site of FIG. 14A, shown with the energy applicator engaging the target site misaligned relative to the trajectory in response to the resistance to rotation illustrated in FIG. 14A, with the tool and the energy applicator arranged in an exaggerated misalignment relative to the trajectory to illustrate a runaway condition.
Figure 14C:
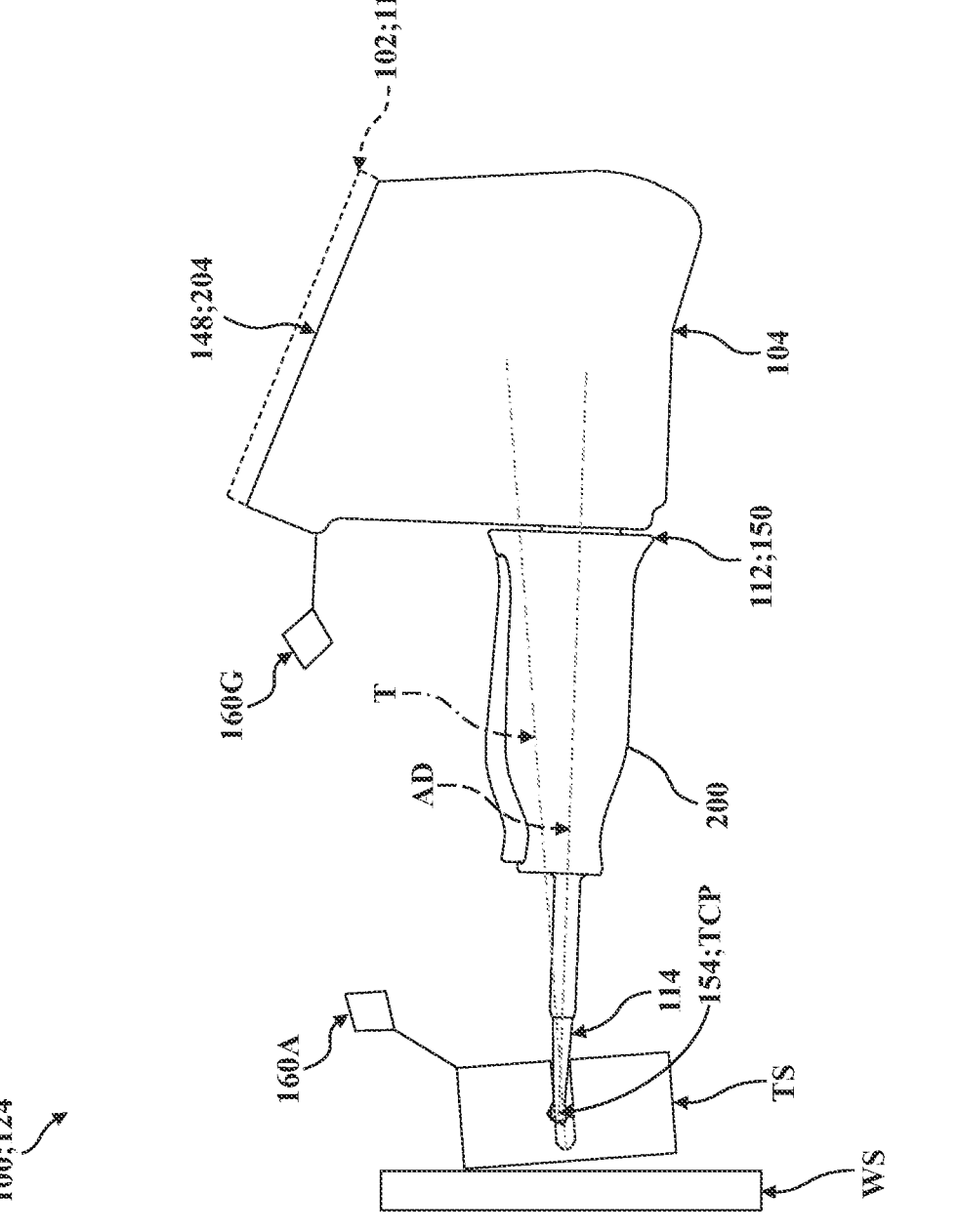
FIG. 14C is another illustrative schematic view of the tool, the energy applicator, and the target site of FIG. 14B, shown with the tool moved together with the energy applicator and the target site away from a support surface to illustrate the runaway condition as the manipulator of FIG. 1 attempts to bring the tool into alignment with the trajectory defined by the target site.
Figure 14D:
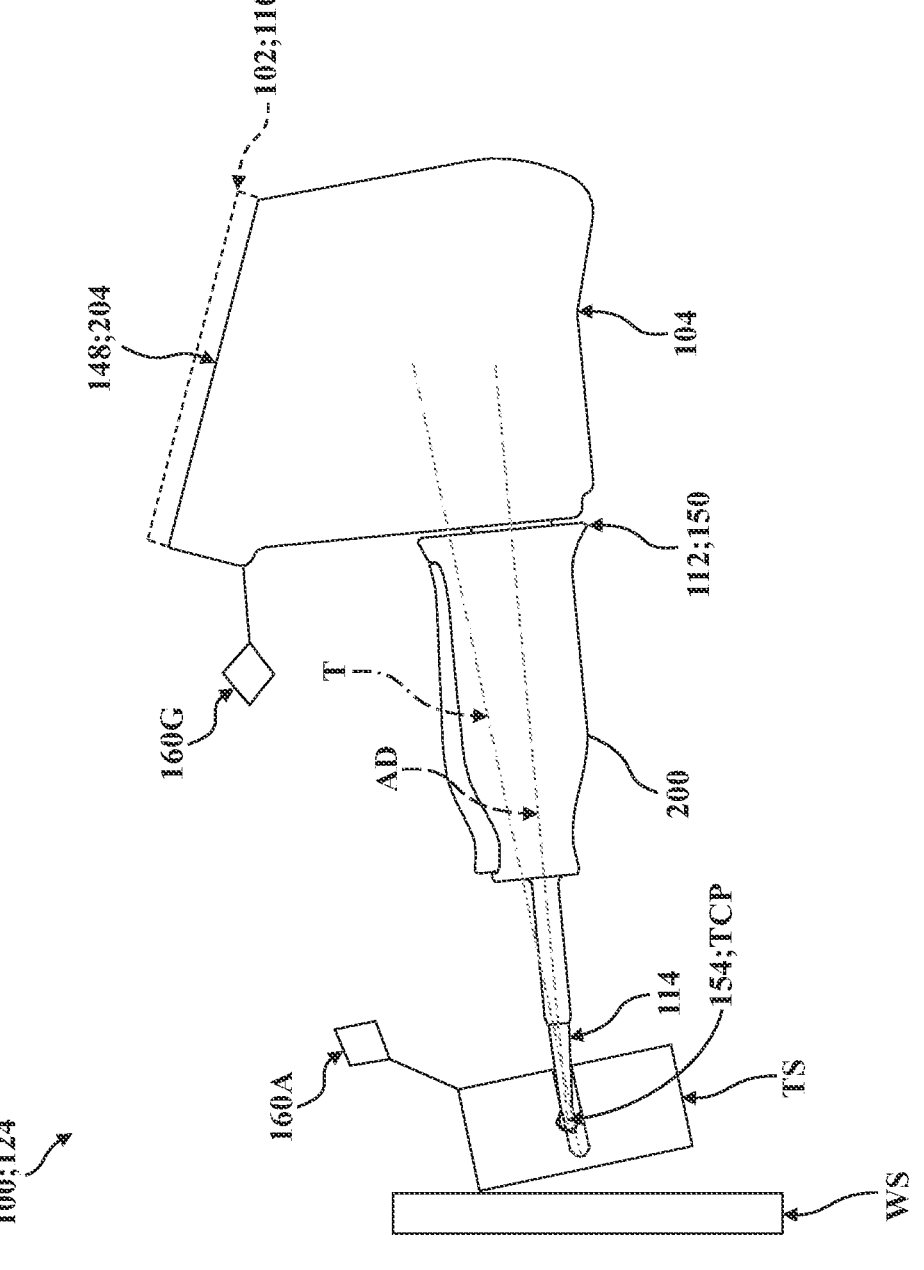
FIG. 14D is another illustrative schematic view of the tool, the energy applicator, and the target site of FIG. 14C, shown with the tool moved further together with the energy applicator and the target site away from a support surface to illustrate the runaway condition as the manipulator of FIG. 1 continues to attempt to bring the tool into alignment with the trajectory defined by the target site.

In this illustrative example, and as is shown by successively comparing FIGS. 14B-14D, movement of the tool 104 toward the target state ST also results in corresponding movement of the target site TS which, as noted above, defines the trajectory T (and, thus, the target state ST) based on the tracked states of the first patient tracker 160A monitored by the navigation system 128. Put differently, as the manipulator 102 attempts to move the tool 104 from the current state SC to the target state ST (e.g., such that the drive axis AD comes back into coincident alignment with the trajectory T), the target site TS moves together with the tool 104 and the target state ST is not reached (e.g., coincident alignment does not occur). As is depicted in FIGS. 14C-14D, this may ultimately result in the target site TS being "lifted off" of the work surface WS.

Figure 15:
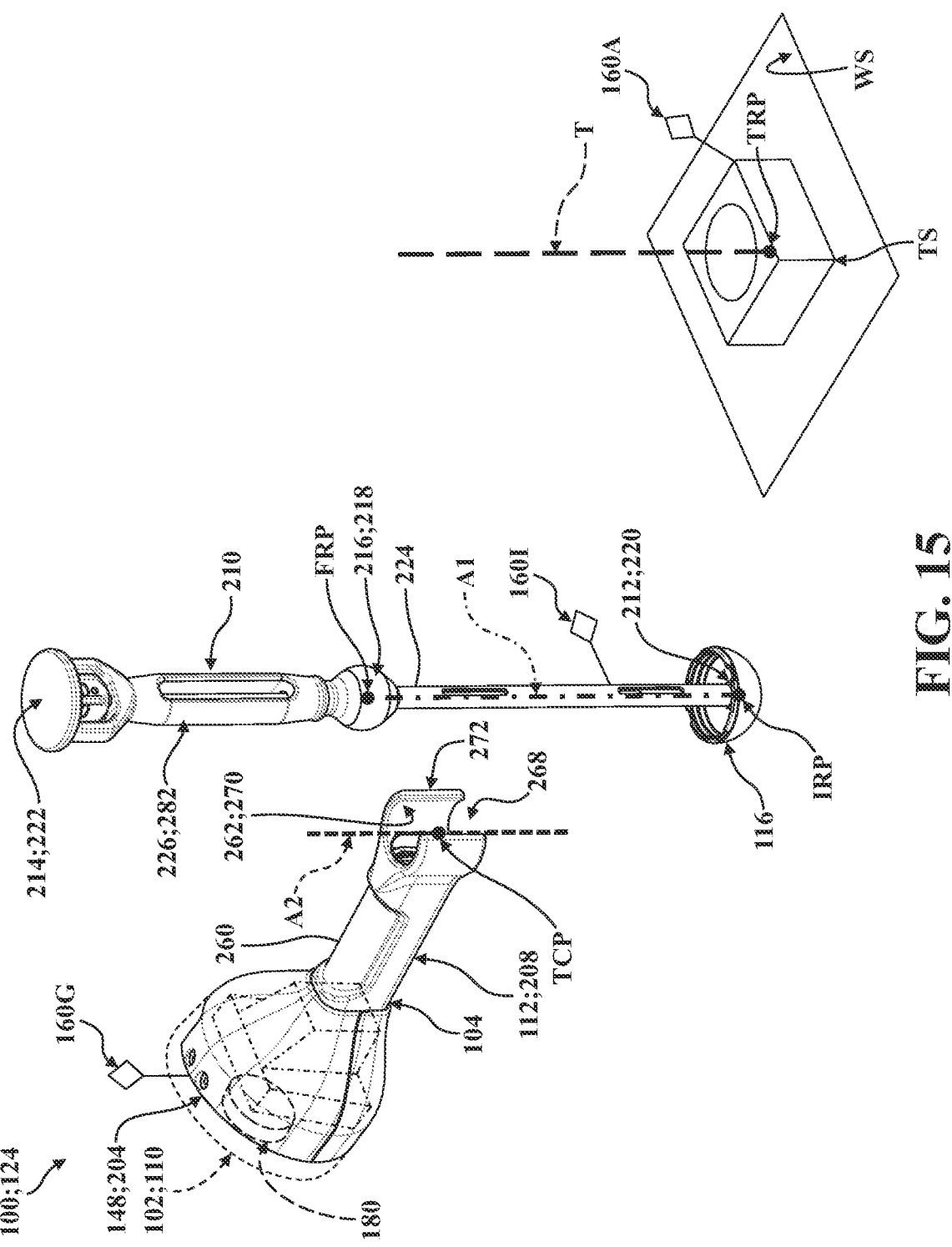
FIG. 15 is a partial perspective view of portions of the surgical system of FIG. 1, depicting the tool comprising guide and the impactor assembly supporting the prosthesis spaced from the trajectory defined by a target site monitored by the navigation system via a tracker.
Figure 25:
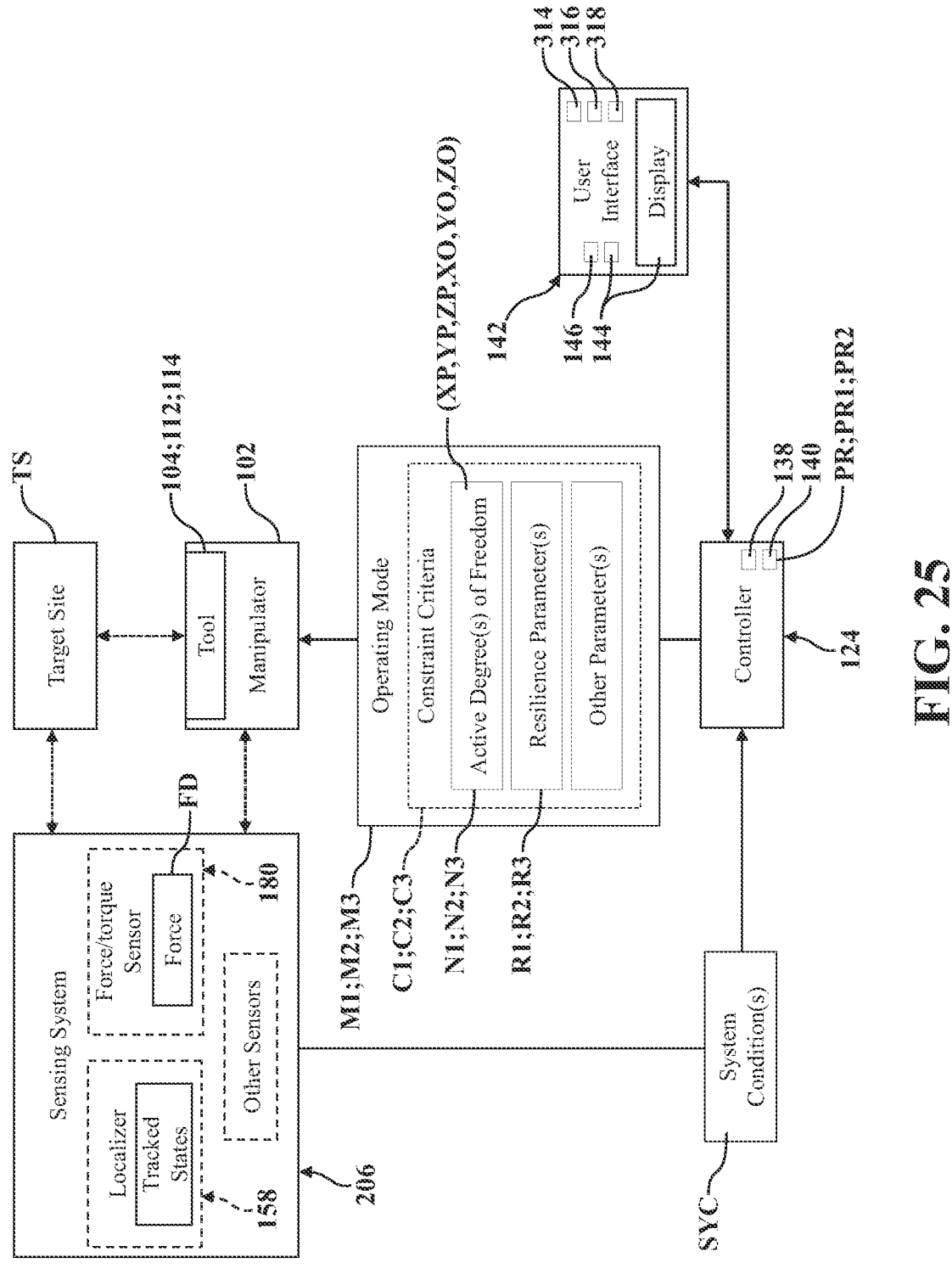
FIG. 25 is a block diagram depicting interaction between a sensing system, a controller, and the manipulator of FIG. 1 according to embodiments of the present disclosure.

Various techniques for detecting and/or responding to "runaway" conditions as they occur are disclosed herein. To this end, and as is described in greater detail below, in some embodiments, the surgical system 100 employs the tool 104 for engaging the target site TS, with the manipulator 102 configured to support the tool 104 relative to the target site TS (e.g., in a target state ST where the tool center point TCP is positioned along the trajectory T). As is described in greater detail below, a sensing system 206 (see FIGS. 1-2) is configured to detect one or more system conditions SYC associated with one or more of the tool 104, the manipulator 102, the target site TS, or combinations thereof. The controller 124 (e.g., the manipulator controller 132, the tool controller 136, or another suitable controller of the surgical system 100; see FIG. 25) coupled to the manipulator 102 and the sensing system 206 is configured to operate the manipulator 102 between: a first mode M1 to maintain alignment of the tool 104 with respect to the target site TS according to a first constraint criteria C1; and a second mode M2 to maintain alignment of the tool 104 with respect to the target site TS according to a second constraint criteria C2 different from the first constraint criteria C1. The controller 124 is further configured to change operation of the manipulator 102 from the first mode M1 to the second mode M2 in response to determining that at least one of the one or more system conditions SYC satisfies a predetermined condition PR. While the sensing system 206, the system conditions SYC, the first and second modes M1, M2, the first and second constraint criteria C1, C2, and the predetermined condition PR are each described in greater detail below, the techniques described herein can be utilized both in connection with tools 104 which engage the target site TS via energy applicators 114, as well as in connection with tools 104 which engage the target site TS via implantable components 116, such as is depicted in FIG. 15. However, other configurations are contemplated, and additional techniques are described in greater detail below.

In some implementations, the first mode M1 and second mode M2 are separate and discrete operating modes of the manipulator 102 that can be activated and deactivated and such as wherein the user can be directly informed of the mode change or wherein there is a pause between mode changes. Alternatively, however, in another implementation, the first and second modes M1 and M2 can be understood as different manners of controlling the manipulator 102 according to a feedback control scheme. For example, the constraint criteria C1, C2 can be changed in real-time or near real-time without activating or deactivating any particular mode, without directly informing the user, or without pausing between mode changes. In other words, the constraint criteria C1, C2 can be changed in a seamless transition with or without the user even being aware or initiating any of the modes M1, M2. Any combination of these implementations is contemplated and the terms "first mode" and "second mode" should understood to include either of these implementations without limitation.

In one implementation, the first and second constraint criteria C1, C2, and values of any parameters associated therewith, are preoperatively determined or predetermined based on information such as clinical data, experimental data, surgeon preferences, or system default settings. In another implementation, the first and second constraint criteria C1, C2, and values of any parameters associated therewith, can be dynamically and intraoperatively determined and/or adjusted by the controller based on measurements from the sensing system, sensor, navigation system or the like, detecting the system conditions SYC or force occurring between the target site and the manipulator. In other implementations, one of the first and second constraint criteria C1, C2 are preoperatively determined or predetermined and the other one of the first and second constraint criteria C1, C2 are intraoperatively determined.

Referring now to FIG. 15, portions of the surgical system 100, including one of the tools 104 of FIG. 1, is shown adjacent to a generically-depicted target site TS. In this embodiment, the tool 104 is configured to facilitate impacting an implantable component 116 (e.g., a prosthetic acetabular cup) at the target site TS (e.g., a reamed acetabulum) along the trajectory T maintained by the manipulator 102. To this end, the instrument 112 of the tool 104 is realized as a guide 208 which, among other things, is configured to attach to the coupling 110 of the robotic arm 108 and supports an impactor assembly 210 for relative movement in one or more degrees of freedom, as described in greater detail below. The impactor assembly 210 comprises, among other things, an interface 212 to releasably secure the implantable component 116, and a head 214 arranged to receive impact force FI (e.g., applied such as by striking the head 214 with a mallet).

In the representative embodiments illustrated herein, the implantable component 116 is a generally hemispherical-shaped cup which forms part of an artificial hip joint adapted for impaction into the patient's P acetabulum. Prior to impaction, the patient's P acetabulum is reamed or otherwise prepared so as to define the target site TS. The reaming, preparing, and impaction processes are described in detail in U.S. Pat. No. 8,979,859 entitled "Depth of Impaction;" and U.S. Pat. No. 8,753,346 entitled "Tool, Kit-of-Parts for Multi-Functional Tool, and Robotic System for Same," the disclosures of which are each hereby incorporated by reference in their entirety. While the present disclosure describes various orthopedic procedures involving hip joints, the subject matter described herein may be applicable to other joints in the patient's P body B, such as for example, shoulders, elbows, wrists, spines, knees, ankles, and the like. Furthermore, the surgical system 100 of the present disclosure may be utilized in connection with a number of different types of orthopedic procedures, and the implantable component 116 could be of a number of different types, styles, configurations, and the like (e.g., cups, stems, screws, pins, rods, wires, anchors, prostheses, and the like). Accordingly, various tools 104 are contemplated, and various styles, types, and/or configurations of guides 208, impactor assemblies 210, and/or implantable components 116 could be utilized without departing from the scope of the present disclosure.

Referring now to FIGS. 15-17B, the representative embodiment of the guide 208 is configured to facilitate advantageous positioning of the implantable component 116 together with the impactor assembly 210 before movement of the impactor assembly 210 and the implantable component 116 is limited by support from the guide 208 (and, thus, the manipulator 102). Put differently, the user (e.g., a surgeon) can approach the target site TS with the implantable component 116 manually and without initially having to support the impactor assembly 210 with the guide 208. After the approach has been completed manually and the implantable component 116 has been disposed at the target site TS, the surgeon can subsequently articulate the implantable component 116 and the impactor assembly 210 into engagement with the guide 208 in a quick, efficient, and reliable manner to facilitate aligning the implantable component 116 with the trajectory T maintained by the manipulator 102. With proper alignment maintained, the surgeon can apply impact force FI to the head 214 of the impactor assembly 210 to install the implantable component 116 into the target site TS. To this end, and as is described in greater detail below, the guide 208 is configured to permit movement of the impactor assembly 210 in one or more degrees of freedom relative to the guide 208 under certain operating conditions of the surgical system 100.

Figure 16A:
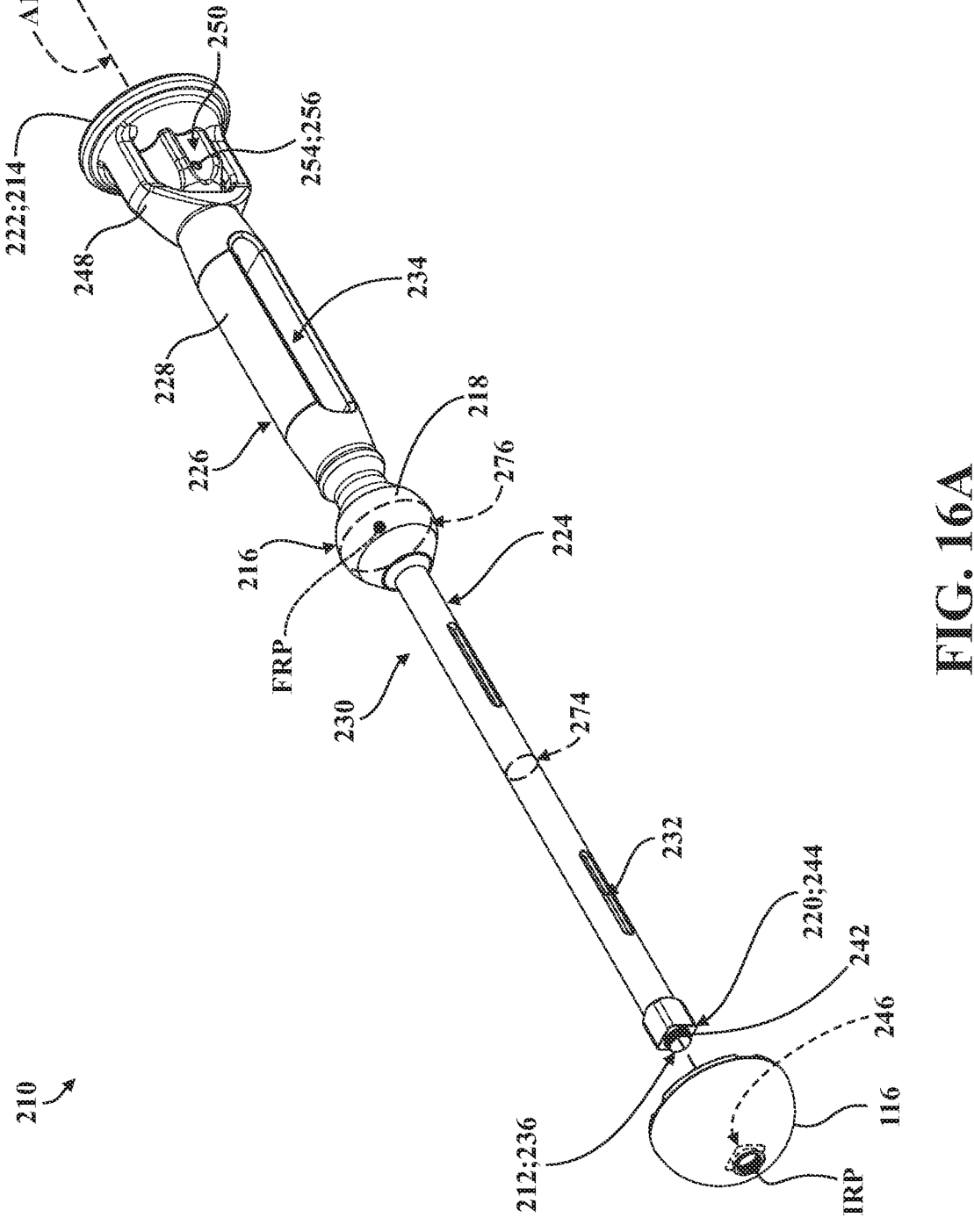
FIG. 16A is a perspective view of the impactor assembly of FIG. 15 shown having an interface spaced from the prosthesis with a shaft extending between the interface and a flange arranged adjacent to a handle extending between the flange and a head.
Figure 16B:
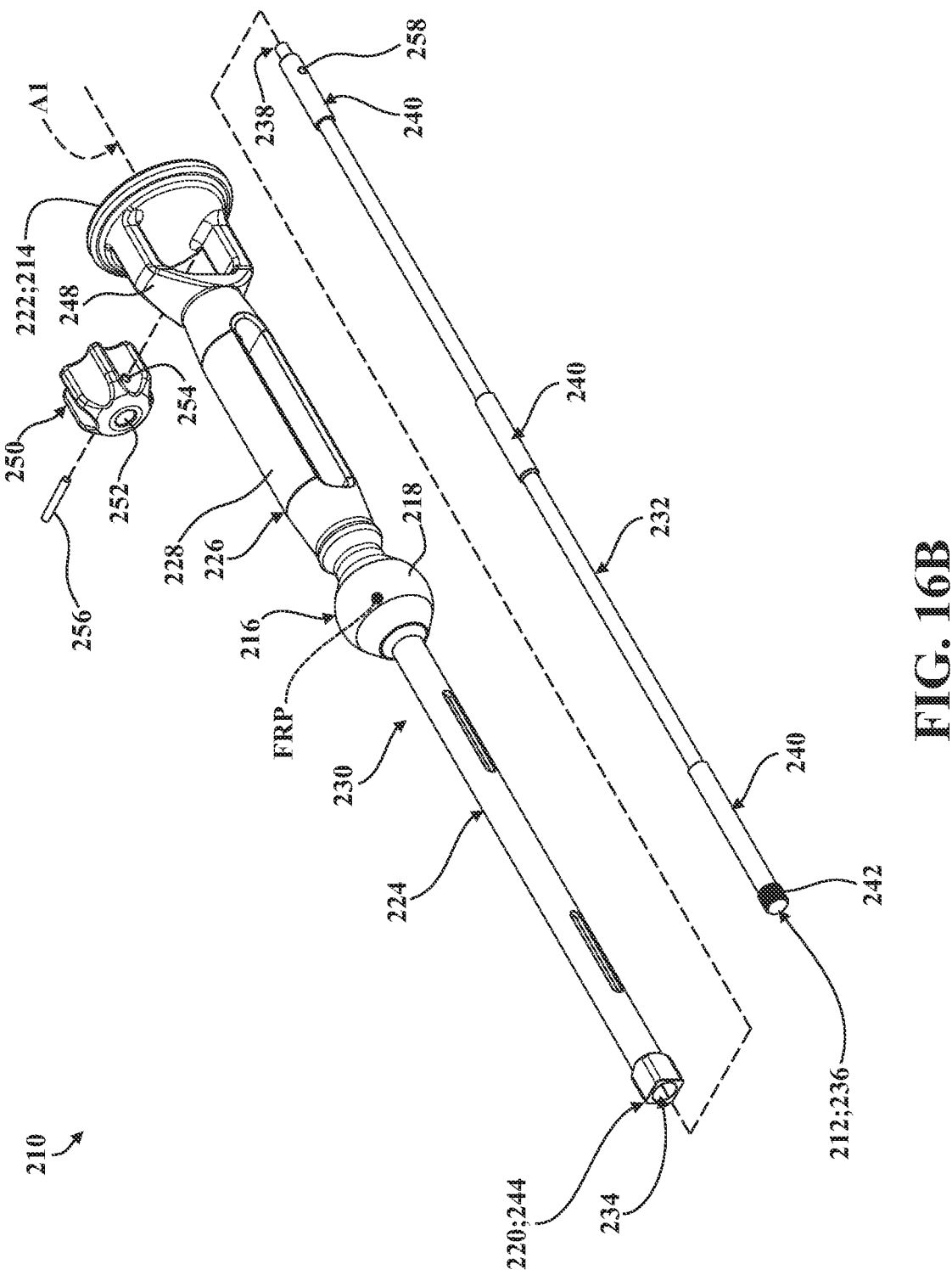
FIG. 16B is an exploded perspective view of the impactor assembly of FIG. 16A.

Referring now to FIGS. 16A-16B, the impactor assembly 210 generally comprises the interface 212 to releasably secure the implantable component 116, and the head 214 arranged to receive impact force FI, as noted above. The impactor assembly 210 also comprises a flange 216 defining a first engagement surface 218 which, as described in greater detail below, abuts the guide 208 to limit movement of the impactor assembly 210 during use. The impactor assembly 210 generally extends along a first axis A1 between a distal end 220 adjacent to the interface 212, and a proximal end 222 adjacent to the head 214. The flange 216 is arranged between the interface 212 and the head 214, has a spherical profile defining the first engagement surface 218, and defines a flange reference point FRP along the first axis A1 that is arranged in the center of the flange 216 (e.g., at the geometric center of the spherical profile which defines the first engagement surface 218). Similarly, the implantable component 116 defines a implant reference point IRP along the first axis A1 of the impactor assembly 210 to which the prosthesis is releasably attached (see FIG. 15), and the target site TS defines a target reference point TRP along the trajectory T (see FIG. 15). A shaft 224 extends along the first axis A1 from the distal end 220 to the flange 216, and a handle 226 with a grip 228 extends between the flange 216 and the head 214. Each of the components of the impactor assembly 210 introduced above will be described in greater detail below.

In the representative embodiment illustrated herein, the head 214, the flange 216, and the shaft 224 are defined by an impactor body, generally indicated at 230, and the interface 212 is defined by a carrier shaft 232 which is accommodated within the impactor body 230. More specifically, the impactor body 230 defines a hollow region 234 which extends along the first axis A1 from the distal end 220, through the shaft 224 and the handle 226 towards the head 214. The carrier shaft 232 generally extends along the first axis A1 between a distal shaft end 236 and a proximal shaft end 238, with one or more bearing regions 240 provided therebetween to facilitate rotation and force distribution. The interface 212 is arranged at the distal shaft end 236, and releasably engages the implantable component 116 such that the impactor assembly 210 and the implantable component 116 move together when attached. To this end, the interface 212 and the implantable component 116 are each provided with a respective threaded engagement, generally indicated at 242 (e.g., internal and external threads; see FIG. 16A), which allows the implantable component 116 to be releasably attached to the impactor assembly 210.

Adjacent to the threaded engagement 242 of the carrier shaft 232, the impactor body 230 is provided with key portion 244 formed at the distal end 220 of the shaft 224. The key portion 244 has a generally rectangular profile shaped to engage a correspondingly-shaped notch portion 246 formed in the implantable component 116 (see FIG. 15A; depicted in phantom). This configuration permits the implantable component 116 to be indexed relative to the shaft 224 (and, thus, the handle 226), which may be advantageous for applications where the implantable component 116 has certain features that need to be aligned relative to the target site TS. Furthermore, this configuration also helps facilitate releasable attachment between the implantable component 116 and the impactor assembly 210 in that rotation and translation of the carrier shaft 232 relative to the shaft 224 can be used to disengage the threaded engagement 242 without also rotating the shaft 224 about the first axis A1. To this end, the handle 226 is also provided with a cage 248 disposed between the head 214 and the grip 228 shaped to accommodate and facilitate access to a knob 250 which, in turn, is operatively attached to the proximal shaft end 238 of the carrier shaft 232. In the illustrated embodiment, the knob 250 comprises an axial knob aperture 252 formed along the first axis A1, and a transverse knob aperture 254 formed transverse to the first axis A1 and disposed in communication with the axial knob aperture 252. The axial knob aperture 252 is shaped to receive the proximal shaft end 238 of the carrier shaft 232, and the transverse knob aperture 254 is shaped to receive a transverse pin 256 which is also received within a transverse shaft aperture 258 formed in the carrier shaft 232 (see FIG. 16B). In addition to ensuring retention of the carrier shaft 232, this configuration also permits the knob 250 and the carrier shaft 232 rotate and translate concurrently about the first axis A1. Here, the cage 248 of the handle 226 has a generally U-shaped profile and is configured to permit limited translation of the knob 250 along the first axis A1 while also providing the surgeon with access to the knob 250.

Figure 17A:
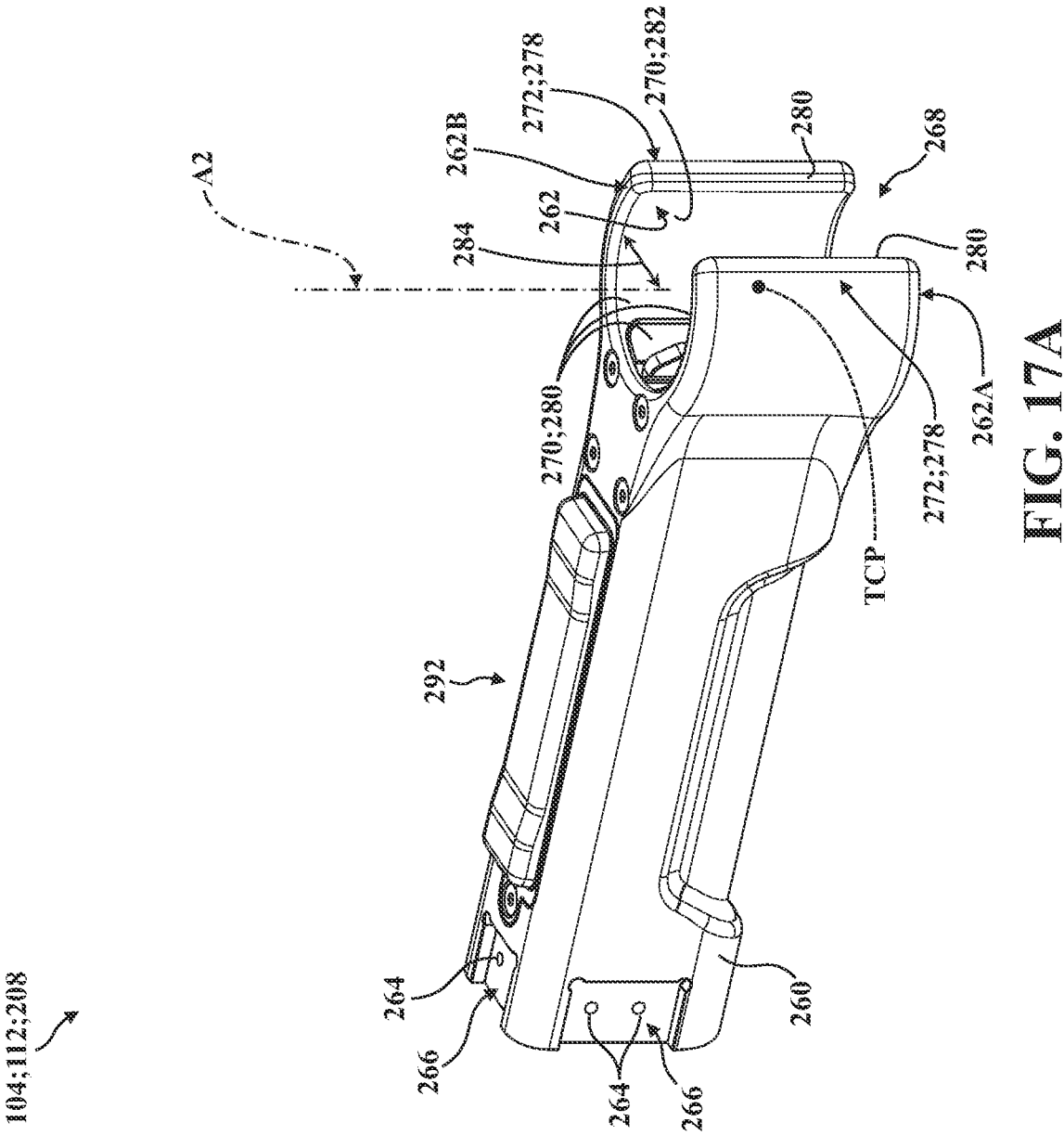
FIG. 17A is a perspective view of the guide of FIG. 15.
Figure 17B:
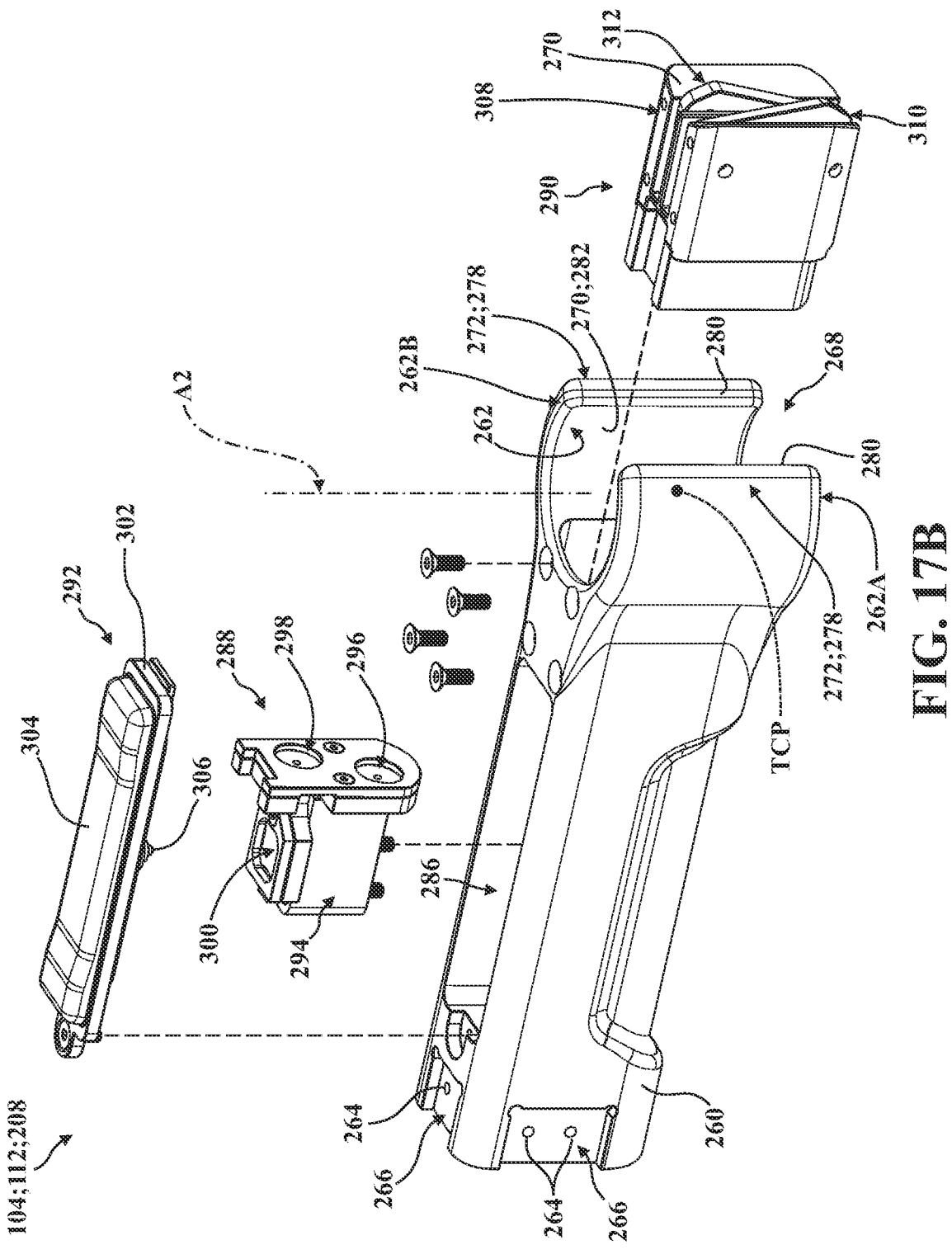
FIG. 17B is a partially-exploded perspective view of the guide of FIG. 17A, shown comprising a body defining a channel.

Referring now to FIGS. 15 and 17A-17B, as noted above, the illustrated embodiment of the tool 104 comprises the guide 208 to releasably secure the impactor assembly 210 in order to, among other things, facilitate maintaining alignment of the first axis A1 with the trajectory T via the robotic arm 108 of the manipulator 102. To this end, the guide 208 generally comprises a mount 148 (see FIG. 15; generically depicted in phantom) adapted to attach to the manipulator 102, and a body 260 operatively attached to the mount 148 and having a channel 262 that extends along a second axis A2. In the representative embodiment illustrated herein, the body 260 of the guide 208 is provided with one or more threaded holes 264 and recessed regions 266 (see FIGS. 17A-17B) which are shaped and arranged to secure to the mount 148 (see FIG. 15; depicted generically) such as via fasteners (not shown). While the mount 148 depicted in FIG. 15 is formed separately from the body 260 in the illustrated embodiment, other configurations are contemplated, and the guide 208 could be formed from or otherwise realized by any suitable number of components sufficient to facilitate coupling to the manipulator 102. Here too, in some embodiments, one or more covers 204 may be employed by the guide 208 of the tool 104 to conceal, protect, or otherwise shield certain components (e.g., the mount 148) from the outside environment. The covers 204 may also conceal electrical components (e.g., wires, electrical connectors, printed circuit boards, and the like), and may be shaped and arranged to permit access to a sterile interface system (not shown, but generally known in the related art) arranged between the mount 148 and the coupling 110 of the robotic arm 108 to facilitate removably attaching the tool 104 to the manipulator 102. Here too, releasable attachment of the coupling 110 to the mount 148 could be achieved in a number of different ways sufficient to secure the tool 104 to the manipulator 102.

As shown in FIGS. 17A-17B, the channel 262 formed in the body 260 of the guide 208 defines an opening 268 arranged to receive a portion of the shaft 224 of the impactor assembly 210 therethrough. The guide 208 also comprises a second engagement surface, generally indicated at 270 (see also FIG. 15), and a limiter 272. The second engagement surface 270 is shaped to abut the first engagement surface 218, and the limiter 272 is configured to maintain abutment between the engagement surfaces 218, 270 and to facilitate coaxial alignment of the axes A1, A2 with the trajectory T maintained by the manipulator 102. The opening 268 of the guide 208 is arranged to permit the shaft 224 of the impactor assembly 210 to pass therethrough when the guide 208 is disposed between the flange 216 and the interface 212 of the impactor assembly 210 so as to facilitate bringing the first axis A1 into alignment with the second axis A2. As is depicted with phantom lines in FIG. 16A, the shaft 224 of the impactor assembly 210 has a first perimeter 274, and the flange 216 of the impactor assembly 210 has a second perimeter 276 which is larger than the first perimeter 274. Put differently, the flange 216 is larger than the shaft 224 and cannot pass through the opening 268 of the guide 208, but the shaft 224 is sized so as to be able to pass through the opening 268.

With continued reference to FIGS. 17A-17B, as noted above, the limiter 272 of the guide 208 is configured to maintain abutment between the first engagement surface 218 and the second engagement surface 270 during impaction, and helps facilitate achieving coaxial alignment of the axes A1, A2 with the trajectory T maintained by the manipulator 102. To this end, the limiter 272 of the illustrated embodiment comprises a pair of fingers, generally indicated at 278, disposed adjacent to the channel 262. The fingers 278 extend from the body 260 of the guide 208 to respective finger ends 280 spaced from each other so as to define the opening 268 therebetween (see FIG. 15). The fingers 278 also each define a respective arc-shaped surface, generally indicated at 282. The arc-shaped surfaces 282 are arranged to contact the flange 216 of the impactor assembly 210 when the second engagement surface 270 abuts the first engagement surface 218, which maintains abutment of the first engagement surface 218 with the second engagement surface 270 and limits movement of the impactor assembly 210 relative to the guide 208 as described below. The arc-shaped surfaces 282 of the limiter 272 are substantially continuous with the second engagement surface 270 of the guide 208, and both the second engagement surface 270 and the arc-shaped surfaces 282 are at least partially defined by the channel 262. More specifically, and as is best depicted in FIG. 17A, the arc-shaped surfaces 282 of the limiter 272 and the second engagement surface 270 of the guide 208 are each spaced from the second axis A2 at a common radius 284 such that the channel 262 has a substantially continuous and generally cylindrical, C-shaped profile, and defines both the second engagement surface 270 and the arc-shaped surfaces 282.

The implantable component 116 and the impactor assembly 210 necessarily translate along the trajectory T as impact force FI is applied to the head 214 of the impactor assembly 210. Thus, the guide 208 and the impactor assembly 210 are configured so as to ensure that abutment between the first engagement surface 218 and the second engagement surface 270 is maintained as the flange 216 moves within the channel 262 (e.g., as the surgeon successively strikes the head 214 of the impactor assembly 210 with a mallet). To this end, the channel 262 of the guide 208 extends between first and second axial channel ends 262A, 262B which are spaced from each other along the second axis A2 at a depth that is greater than a thickness of the flange 216 (not shown in detail). Here, the guide 208 defines the tool center point TCP in this embodiment, which is arranged along the second axis A2 in the center of the channel 262 (e.g., spaced equidistantly between the first and second axial channel ends 262A, 262B). However, the tool center point TCP could be defined in other ways without departing from the scope of the present disclosure.

Because the flange 216 has a generally spherical profile as noted above, only a portion of the flange 216 which defines the first engagement surface 218 actually engages the cylindrical channel 262 when the second engagement surface 270 abuts the first engagement surface 218. Thus, the channel 262 is advantageously configured so as to be deep enough to ensure that the flange 216 can be readily positioned within and remain in abutment with the channel 262 during impaction. However, maintaining abutment between the second engagement surface 270 and the first engagement surface 218 can be achieved in other ways, such as by advancing the guide 208 along the trajectory T and toward the target site TS with the manipulator 102 during impaction (e.g., to position the tool center point TCP at the flange reference point FRP). Other configurations are contemplated.

As is best shown in FIG. 17B, the body 260 of the guide 208 also comprises a pocket 286 which accommodates a sensor subassembly 288, a follower subassembly 290, and an input module 292, each of which are described in greater detail below. The pocket 286 extends into communication with the channel 262 to facilitate attachment of the follower subassembly 290 which sits in the pocket 286 adjacent to the channel 262. Here, a portion of the follower subassembly 290 also defines part of the second engagement surface 270 (see FIG. 17A).

The sensor subassembly 288 generally comprises a sensor housing 294 which is secured to the body 260 of the guide 208 via fasteners (not shown in detail) and supports a first trigger sensor 296, a second trigger sensor 298, and an input sensor 300, each of which may be disposed in communication (e.g., wired or wireless electrical communication) with the controller 124 (e.g., the manipulator controller 132, the tool controller 136, or another suitable) or other components of the surgical system 100. The input sensor 300 is arranged so as to be engaged by or otherwise disposed in communication with the input module 292, and the first and second trigger sensors 296, 298 are arranged so as to be engaged by or otherwise disposed in communication with the follower subassembly 290. As will be appreciated from the subsequent description below, each of the sensors of the sensor subassembly 288 could be of a number of different types, styles, configurations, and the like, and other configurations besides those specifically illustrated herein are contemplated by the present disclosure.

The input module 292 is configured for selective actuation by the surgeon and generally comprises an input frame 302 and an input button 304. The input frame 302 is secured to the body 260 of the guide 208 via one or more fasteners (not shown in detail), and supports the input button 304 for movement relative thereto. The input button 304 comprises a protrusion 306 arranged to engage the input sensor 300 in response to actuation by the surgeon (e.g., by pressing on the input button 304). In some embodiments, the input button 304 could be resiliently biased away from the input frame, such as by a spring (not shown). However, other configurations are contemplated. The input module 292 may be configured to facilitate operating the manipulator 102 in different ways during a surgical procedure, and may serve as an input device 146.

The follower subassembly 290, like the sensor subassembly 288, is accommodated within the pocket 286 formed in the body 260 of the guide 208 and is secured to the body 260 with fasteners (not shown in detail). The follower subassembly 290 generally comprises a follower housing 308 which supports first and second triggers 310, 312 which are shaped and arranged to engage against the flange 216 of the impactor assembly 210 in the illustrated embodiment. To this end, the first and second triggers 310, 312 extend into the channel 262 and are supported by the follower housing 308 so as to deflect towards the sensor subassembly 288 in response to engagement with the flange 216, and independently actuate respective pushrods (not shown) supported within the follower housing 308 which respectively engage the first and second trigger sensors 296, 298. Here, the follower subassembly 290 and the sensor subassembly 288 facilitate the ability to determine one or more of the presence of the flange 216 within the channel 262 and/or the relative position of the flange 216 between the first and second axial channel ends 262A, 262B such as to facilitate "tracking" movement of the implantable component 116 along the trajectory T during impaction at the target site TS based on corresponding to changes in the axial position of the flange 216 along the channel 262.

As noted above, the manipulator 102 is configured to position the tool 104 with respect to the target site TS and to maintain the trajectory T which, in embodiments directed toward impacting the implantable component 116, is generally linear and is aligned with the axes A1, A2. Here, external impact force FI applied to the head 214 of the impactor assembly 210 translates through the impactor assembly 210 and to the implantable component 116 which, in turn, causes the implantable component 116 to advance along the trajectory T toward the target site TS. While the process of impacting the implantable component 116 is described in greater detail below, maintaining the trajectory T may involve the manipulator 102 restricting all or certain types of movement of the guide 208 relative to the target site TS in certain conditions, and/or may involve limiting or directing movement of the guide 208 into translation along the trajectory T relative to the target site TS in some embodiments. The manipulator 102 may permit the surgeon to translate the guide 208 along the trajectory T to, among other things, facilitate passing the shaft 224 of the impactor assembly 210 through the opening 268 of the guide 208, as noted above. Certain steps of surgical procedures may involve controlling the manipulator 102 in different ways. Furthermore, various configurations of tools 104 are contemplated by the present disclosure and, in some embodiments, one or more portions of the surgical system 100, the tool 104, the instrument 112, and/or the implantable component 116 may be similar to as is described in U.S. Patent Application Publication No. US 2019/0231446 A1 entitled "End Effectors, Systems, And Methods For Impacting Prosthetics Guided By Surgical Robots," the disclosure of which is hereby incorporated by reference in its entirety. Other configurations are contemplated.

Referring now to FIGS. 18-21D, portions of the surgical system 100 and a generically-depicted target site TS are shown schematically, with the target site TS shown supported on the work surface WS (e.g., a surgical table; not shown in detail). Here, the target site TS represents intended position of the implantable component 116 when impacted into the acetabular cup (intended position shown in phantom in FIG. 18). The acetabulum, here, has been reamed or otherwise prepared to define the trajectory T and has the first patient tracker 160A firmly fixed thereto. As noted above, tracked states (e.g., positional and/or orientational data, or data based thereon) of first patient tracker 160A monitored by the navigation system 128 are used to facilitate maintaining the target state SA to ensure alignment of the manipulator 102 with the target site TS, such as by controlling the robotic arm 108 of the manipulator 102 to keep the second axis A2 defined by the guide 208 in coincident alignment with the trajectory T defined by the target site TS.

Figure 18:
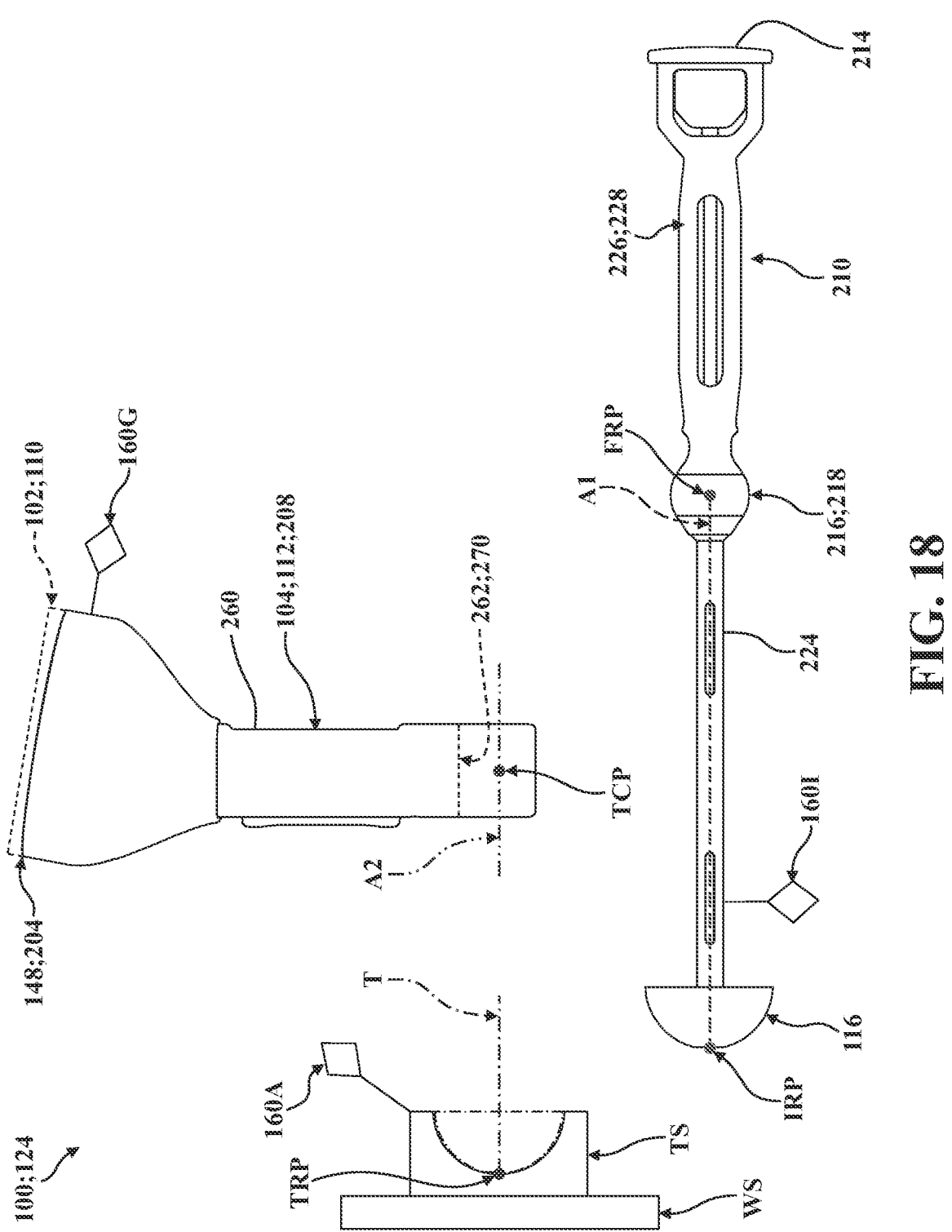
FIG. 18 is an illustrative schematic view of the prosthesis and tool of FIGS. 15-17B, shown with the guide defining a guide axis aligned with the trajectory of the target site, and shown with the impactor assembly attached to the prosthesis and spaced from both the target site and the guide.

In FIG. 18, the mount 148 (represented by the covers 204 for illustrative purposes; see also FIG. 15) and the guide 208 of the tool 104 are positioned adjacent to the target site TS supported by the manipulator 102 (partially depicted and shown in phantom), with the second axis A2 aligned to the trajectory T (and, thus, with the tool center point TCP arranged along the trajectory T). The impactor assembly 210 is shown spaced from both the target site TS and the guide 208, with the implantable component 116 secured to the interface 212 and arranged along the first axis A1. For illustrative purposes, the first tool tracker 160G is shown firmly fixed to the guide 208, and the second tool tracker 160I is shown firmly fixed to the impactor assembly 210. However, while the navigation system 128 can track states of multiple trackers 160 within a common coordinate system as noted above, the pose of a tracked object (e.g., the tool 104) can be determined in other ways (e.g., based on known geometric relationships) and transformed between coordinate systems (e.g., between the manipulator coordinate system MNPL and the localizer coordinate system LCLZ). Put differently, the surgical system 100 can determine changes in the pose of the tool 104 relative to the first patient tracker 160A without necessarily utilizing the illustrated first tool tracker 160G and/or second tool tracker 160I because, among other things, the geometry of the guide 208, the impactor assembly 210, and the implantable component 116 are known and the arrangement of the flange reference point FRP relative to the tool center point TCP can be determined when the flange 216 is disposed within the channel 262 (e.g., via the sensor subassembly 288).

Figure 19A:
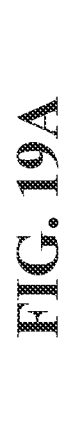
FIG. 19A is another illustrative schematic view of the tool, the prosthesis, and the target site of FIG. 18, shown with the prosthesis and the impactor assembly positioned adjacent to the target site, with the flange of the impactor assembly supported in the channel of the guide, and with an applied force acting on the guide.
Figure 19B:
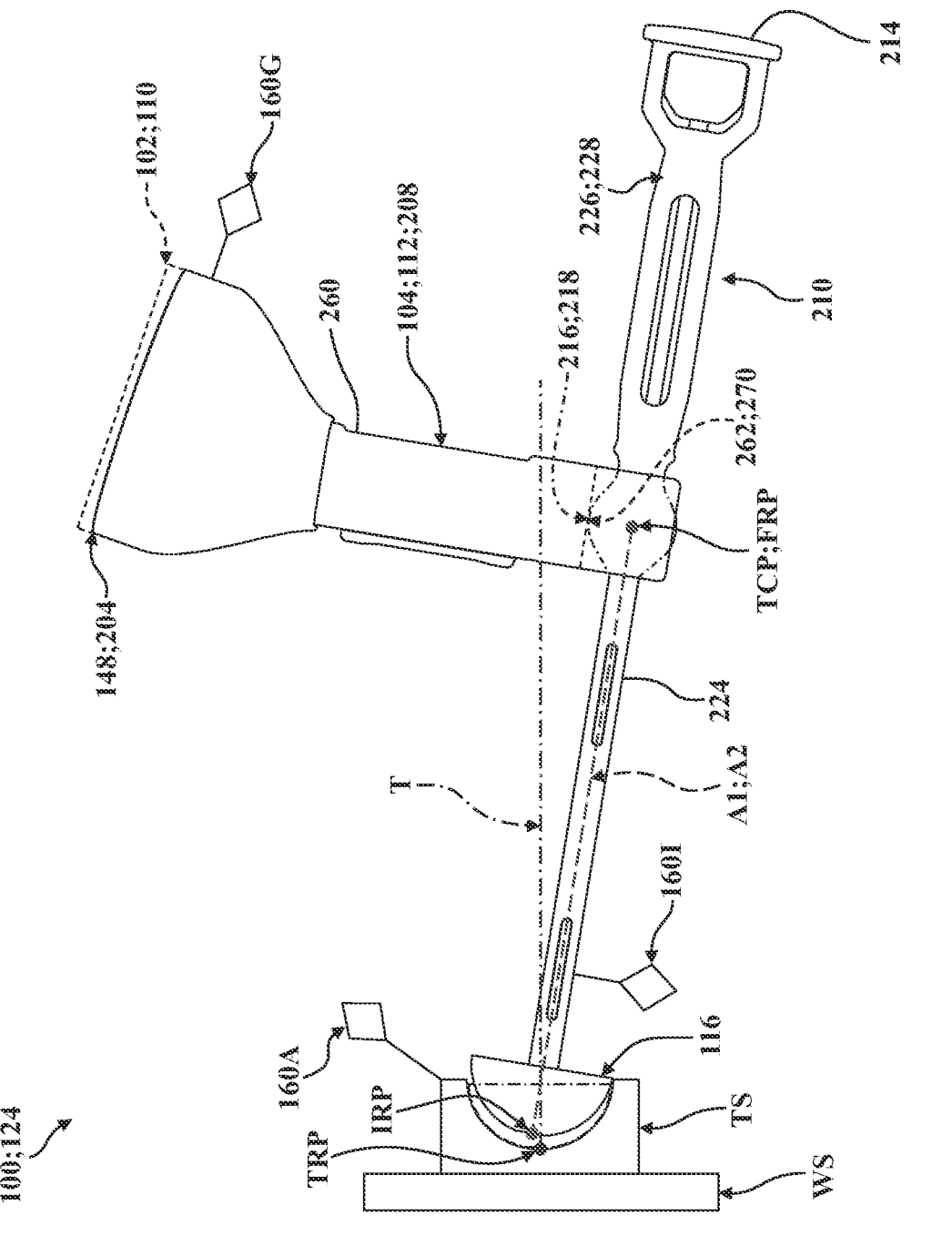
FIG. 19B is another illustrative schematic view of the tool, the prosthesis, and the target site of FIG. 19A, shown with the tool and the prosthesis moved relative to the trajectory and the target site in response to the applied force illustrated in FIG. 19A.

Referring now to FIG. 19A, the impactor assembly 210 has been moved together with the implantable component 116 into an initial position adjacent to the target site TS (here, the reamed acetabulum), with the first axis A1 defined by the impactor assembly 210 in coaxial alignment with both the second axis A2 defined by the guide 208 and with the trajectory T defined by the target site TS. Here, the flange 216 of the impactor assembly 210 is disposed within the channel 262 of the guide 208, with the flange reference point FRP disposed in alignment with the tool center point TCP. The implant reference point IRP defined by the implantable component 116 is spaced from the target reference point TRP defined by the target site TS.

As noted above, when operating in the guided-haptic mode, or other modes, the surgical system 100 may be configured to interpret force detected by the sensor 180 an input that is used to drive the robotic arm 108 of the manipulator 102 which, among other things, may allow the surgeon to touch or otherwise engage against different parts of the robotic arm 108 and/or the tool 104 to move them in certain directions during certain operational conditions. To illustrate this concept, FIG. 19A depicts an applied force FA acting on the guide 208, such as from the surgeon pushing and/or pulling on the guide 208 or the impactor assembly 210 with their hand (not shown in detail). For illustrative purposes, if the manipulator 102 were not configured to maintain alignment with the trajectory T as depicted here (e.g., where the target state ST is defined so as to result in coincident alignment between the second axis A2 and the trajectory T), the applied force FA depicted in FIG. 19A could result in movement of the tool 104 (via the robotic arm 108) to the arrangement depicted in FIG. 19B, bringing the axes A1, A2 out of coincident alignment with the trajectory T (e.g., as depicted in FIG. 19A). In this hypothetical, illustrative example, the surgeon could be operating the robotic arm 108 in the manual mode or another mode (e.g., activated via the input button 304) to refine or finalize their approach and initial positioning of the implantable component 116 in engagement with the target site TS prior to impaction, before subsequently bringing the axes A1, A2 into coincident alignment with the trajectory T defined by the target site TS and maintaining the coincident alignment with the manipulator 102 as illustrated in FIG. 20A.

Figure 20A:
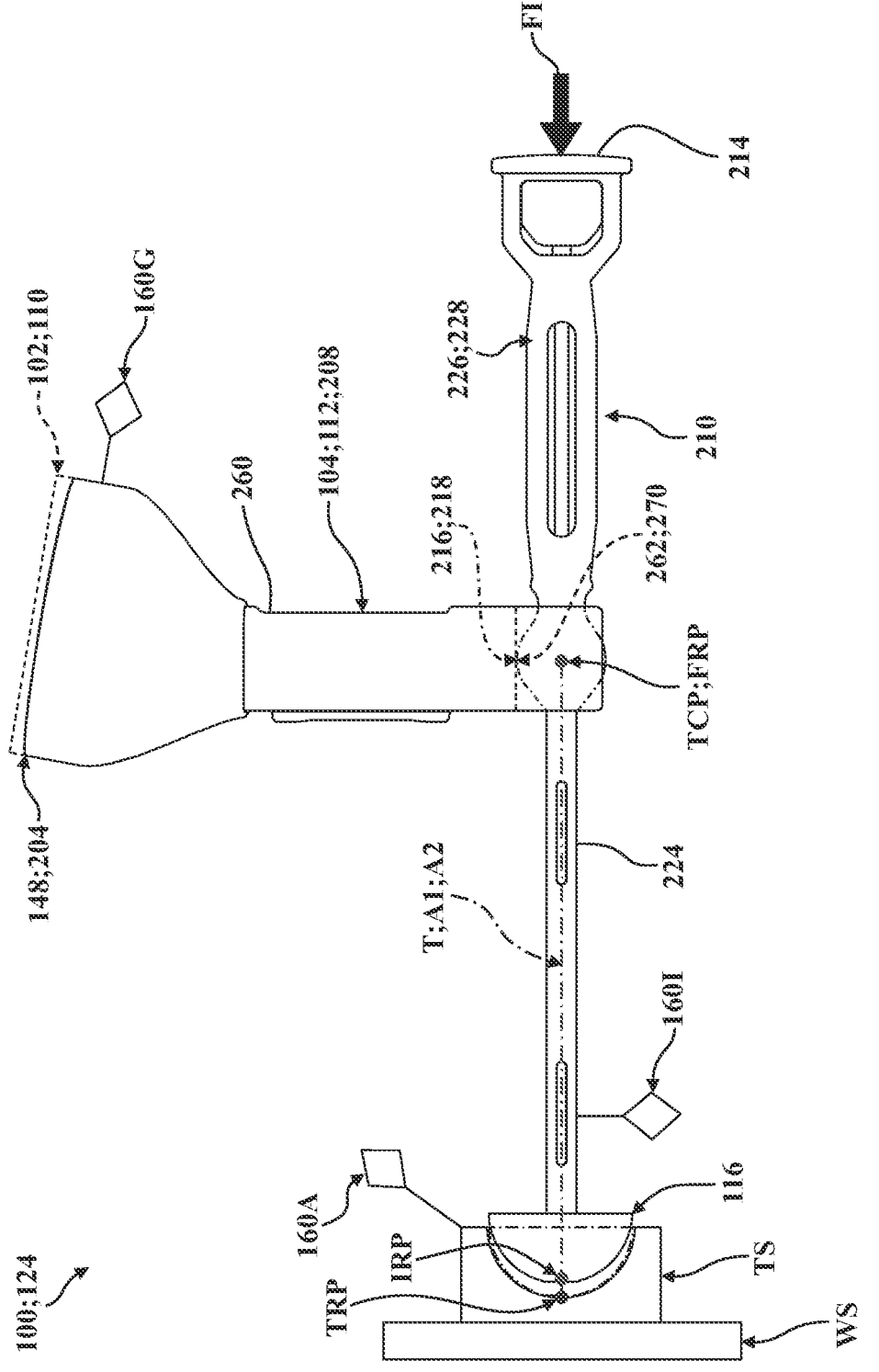
FIG. 20A is another illustrative schematic view of the tool, the prosthesis, and the target site of FIG. 18, shown with the prosthesis and the impactor assembly positioned adjacent to the target site, with the flange of the impactor assembly supported in the channel of the guide, and with an applied force acting on the head of the impactor assembly substantially along the trajectory.
Figure 20B:
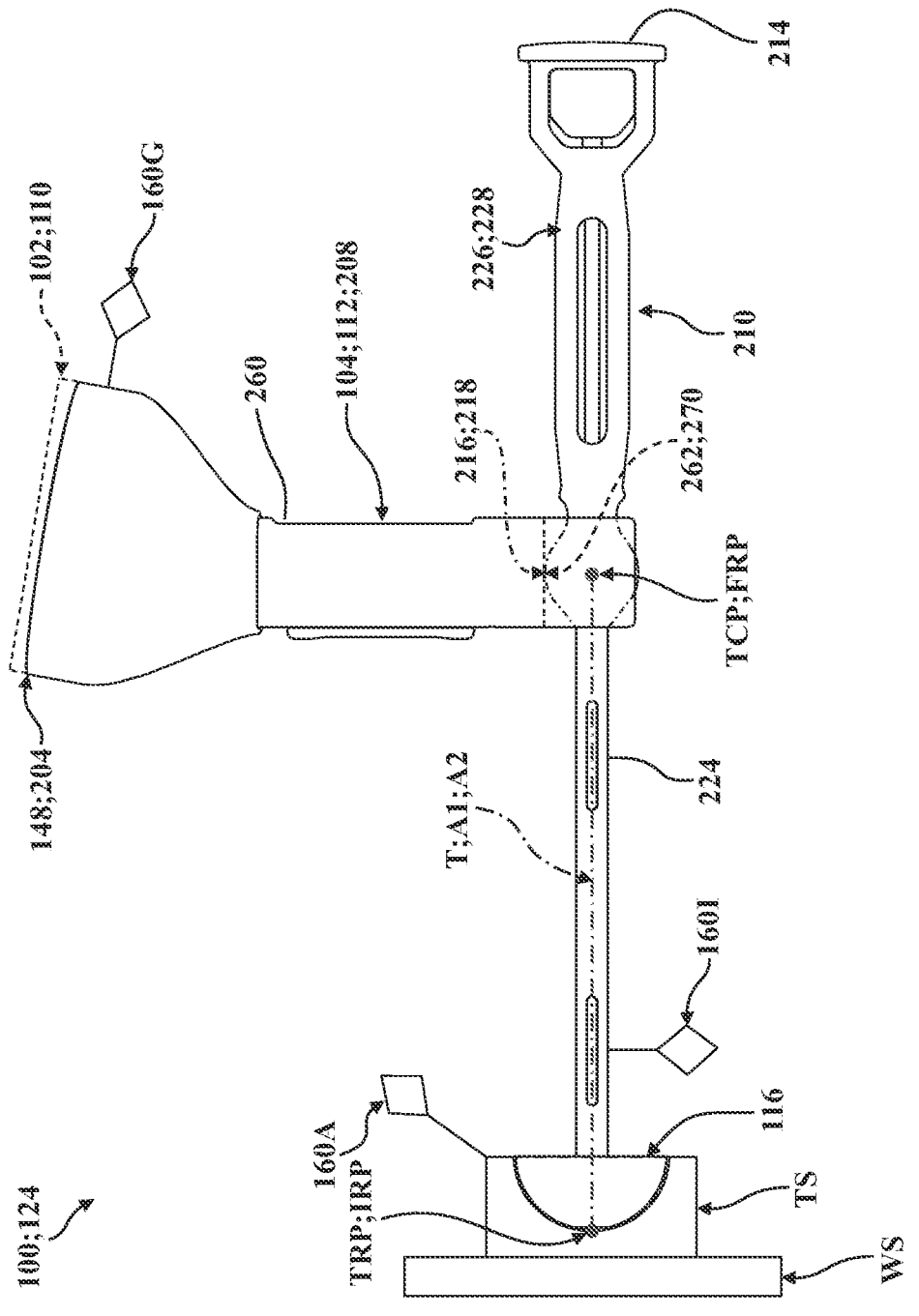
FIG. 20B is another illustrative schematic view of the tool, the prosthesis, and the target site of FIG. 20A, shown with the prosthesis implanted at the target site along the trajectory in response to the applied force illustrated in FIG. 20A.

In the illustrative example depicted in FIG. 20A, manipulator 102 is being operated so as to maintain alignment of the second axis A2 (defined by the guide 208) with the target site TS (e.g., via coincidence with the trajectory T), which is also aligned with the first axis A1 (defined by the impactor assembly 210). Here, the target state ST could be defined by the tool center point TCP being disposed along the trajectory T. With the alignment maintained by the manipulator 102 as illustrated here, the surgeon can apply impact force FI to the head 214 of the impactor assembly 210, such as by successively striking the head 214 with a mallet (not shown) in order to install the implantable component 116 into the target site TS. As illustrated by FIG. 20B, in response to the proper application of impact force FI to the head 214, the impactor assembly 210 and the implantable component 116 move together along the trajectory T to bring the implant reference point IRP (defined by the implantable component 116) into alignment with the target reference point TRP (defined by the target site TS).

Here, the manipulator 102 could be configured to advance the guide 208 along the trajectory T toward the target site TS between mallet strikes during impaction in order to bring the tool center point TCP (defined by the channel 262 of the guide 208) back into alignment with the flange reference point FRP (defined by the flange 216 of the impactor assembly 210) which, as noted above, may be determined via the follower subassembly 290 and/or the sensor subassembly 288, and or via the navigation system 128 based on tracked states of the second tool tracker 160I and the first tool tracker 160G. The manipulator 102 may not necessarily advance the guide 208 along the trajectory T if, for example, the axial channel ends 262A, 262B are spaced from each other at a distance large enough to ensure that the flange 216 will remain in engagement with the channel 262 during impaction, which may be advantageous in embodiments where the surgical system 100 is able to determine the relative position of the flange 216 along the channel 262 with a high degree of accuracy, such by using a linear variable differential transformer (LVDT) coil arrangement coupled to the tool 104. Embodiments of this type of LVDT coil arrangement are described in U.S. Patent Application Publication No. US 2019/0231446 A1 entitled "End Effectors, Systems, And Methods For Impacting Prosthetics Guided By Surgical Robots," previously referenced. Other configurations are contemplated.

As noted above, the illustrated embodiments of the tool 104 are generally configured to permit translation of the impactor assembly 210 relative to the guide 208 to facilitate bringing the implantable component 116 into engagement with the target site TS. Furthermore, the embodiments of the tool 104 are also generally configured to permit rotation of the impactor assembly 210 relative to the guide 208, and/or vice-versa, in one or more degrees of freedom. This relative rotation is achieved by bearing-type contact (e.g., sliding contact) occurring between the first engagement surface 218 and the second engagement surface 270. Here, the ability of the impactor assembly 210 to rotate and translate relative to the guide 208 helps prevent significant amounts of force and/or torque from translating from the impactor assembly 210 to the guide 208 (and, thus, to the manipulator 102) such as, for example, during the application of impact force FI. However, a certain amount of force and/or torque are necessarily translated to the manipulator 102 in one or more degrees of freedom DOF due to the physical contact occurring between the guide 208 and the impactor assembly 210.

Figure 21A:
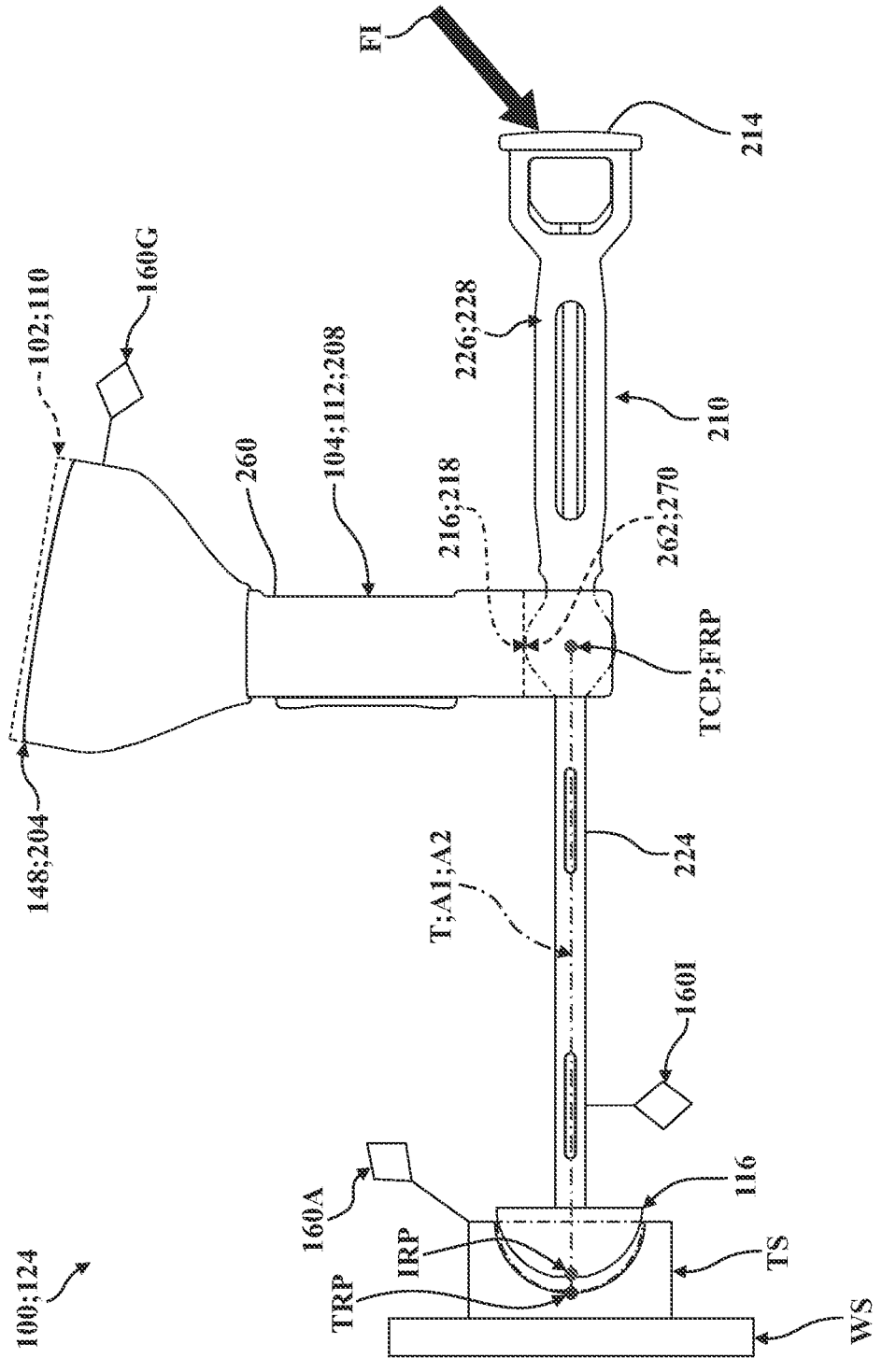
FIG. 21A is another illustrative schematic view of the tool, the prosthesis, and the target site of FIG. 18, shown with the prosthesis and the impactor assembly positioned adjacent to the target site, with the flange of the impactor assembly supported in the channel of the guide, and with an applied force acting on the head of the impactor assembly transverse to the trajectory.

In FIG. 21A, the impactor assembly 210, the guide 208, the implantable component 116, and the manipulator 102 are generally arranged in the same way as is depicted in FIG. 20A, with the second axis A2 (defined by the guide 208) aligned with the target site TS (e.g., via coincidence with the trajectory T), which is also aligned with the first axis A1 (defined by the impactor assembly 210), and with the implantable component 116 arranged in engagement with the target site TS prior to impaction. However, in FIG. 21A, the impaction force FI is shown as being improperly applied to the head 214 of the impactor assembly 210 (e.g., transverse to the trajectory T). Here, the improper application of impact force FI (e.g., relatively high in magnitude and/or misaligned with the trajectory T) may result in the implantable component 116 becoming seated (e.g., partially seated) into the target site TS in a way that is misaligned with the trajectory T (e.g., where the first axis A1 and the second axis A2 are not coincident with the trajectory T). Such a hypothetical scenario is depicted in FIG. 21B, which shows exaggerated misalignment between the axes A1, A2 and the trajectory T for illustrative purposes.

Figure 21B:
FIG. 21B is another illustrative schematic view of the tool, the prosthesis, and the target site of FIG. 21A, shown with the prosthesis implanted at the target site misaligned relative to the trajectory in response to the applied force illustrated in FIG. 20A, with the tool and the prosthesis arranged in an exaggerated misalignment relative to the trajectory to illustrate a runaway condition.

In FIG. 21B, like the scenario described above in connection with FIGS. 14A-14D, a hypothetical "runaway" condition of the surgical system 100 may occur as a result of the misalignment with the trajectory T. Here, the improper application of impact force FI has seated the implantable component 116 into the target site TS in a way that causes misalignment of the first and second axes A1, A2 with the trajectory T. While the target state ST of the tool 104 could be defined in a number of different ways, for illustrative purposes in this representative example, the target state ST includes (or otherwise results in) coincident alignment between the second axis A2 and the trajectory T (e.g., with the tool center point TCP disposed along the trajectory T). However, because the current state SC of the tool 104 shown in FIG. 21B includes misalignment between the second axis A2 and the trajectory T with the implantable component 116 "locked" to the target site TS, a "runaway" condition may similarly occur as the manipulator 102 attempts to move from the current state to the target state ST. The "runaway" condition may also occur as a result of the patient tracker 160 becoming loose from the target site TS thereby causing a loss of tracking accuracy.

Figure 21C:
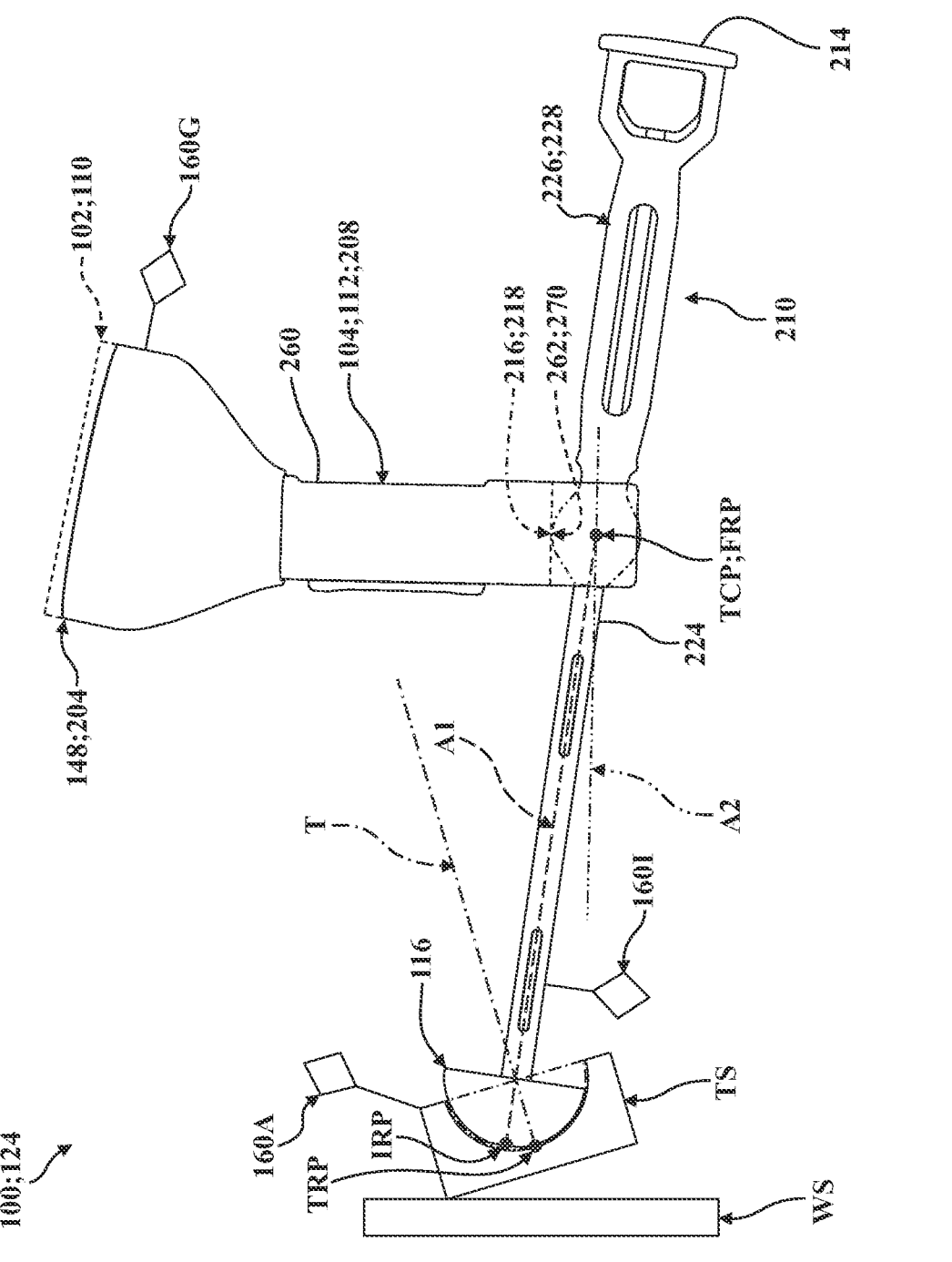
FIG. 21C is another illustrative schematic view of the tool, the prosthesis, and the target site of FIG. 21B, shown with the tool moved together with the implanted prosthesis and the target site away from a support surface to illustrate the runaway condition as the manipulator of FIG. 1 attempts to bring the guide into alignment with the trajectory defined by the target site.
Figure 21D:
FIG. 21D is another illustrative schematic view of the tool, the prosthesis, and the target site of FIG. 21C, shown with the tool further moved together with the implanted prosthesis and the target site away from the support surface to illustrate the runaway condition as the manipulator of FIG. 1 continues to attempt to bring the guide into alignment with the trajectory defined by the target site.

In this illustrative example, and as is shown by successively comparing FIGS. 21B-21D, movement of the tool 104 (e.g., the guide 208) toward the target state ST (e.g., to bring the tool center point TCP back onto the trajectory T) also results in corresponding movement of the target site TS which, as noted above, defines the trajectory T (and, thus, the target state ST) based on the tracked states of the first patient tracker 160A monitored by the navigation system 128. Put differently, as the manipulator 102 attempts to move the tool 104 (e.g., the guide 208) from the current state SC to the target state ST (e.g., such that the first and second axes A1, A2 come back into coincident alignment with the trajectory T), the target site TS moves together with the tool 104 and the target state ST is not reached (e.g., coincident alignment does not occur). Here too, as depicted in FIGS. 21C-21D, this may ultimately result in the target site TS being "lifted off" of the work surface WS.

As noted above, various techniques for detecting and/or responding to "runaway" conditions as they occur are contemplated by the present disclosure, including for surgical systems 100 which utilize tools 104 with instruments 112 such as the guide 208 to support the impactor assembly 210 to facilitate engagement of the implantable component 116 with the target site TS (e.g., as described above in connection with FIGS. 18-21D), as well as for surgical systems 100 which utilize tools 104 with instruments 112 such as the powered surgical device 150 to facilitate engagement of the energy applicator 114 with the target site TS (e.g., as described above in connection with FIGS. 12-14D). To this end, the controller 124 may detect a "runaway" condition by monitoring one or more system conditions SYC (e.g., as detected via the sensing system 206) against one or more predetermined conditions PR (e.g., a first predetermined condition PR1, a second predetermined condition PR2, and the like), as noted above and as is described in greater detail below.

The sensing system 206 is configured to detect one or more system conditions SYC associated with one or more of the tool 104, the manipulator 102, the target site TS, or combinations thereof, as noted above (see FIG. 25). Put differently, the sensing system 206 may detect one or more system conditions SYC associated with the tool 104, one or more system conditions SYC associated with the manipulator 102, and/or one or more system conditions SYC associated with the target site TS. To this end, in some embodiments, the sensing system 206 may comprise the sensor 180 to detect force FD occurring between the target site TS and the manipulator 102. Here, for example, forces FD (e.g., force and/or torque in one or more degrees of freedom DOF) detected by the sensor 180 could define system conditions SYC used by the controller 124 to facilitate changing operation of the manipulator 102 between the first and second modes M1, M2, as described in greater detail below. In some embodiments, the sensing system 206 may comprise one or more components of the navigation system 128 (e.g., the localizer 158) and/or one or more trackers 160. Here, for example, tracked states of trackers 160 monitored by the localizer 158 could define systems conditions SYC used by the controller 124 to facilitate changing operation of the manipulator 102 between the first and second modes M1, M2, as described in greater detail below. Here too, as noted above, one or more components of the surgical system 100 are able to determine (either directly or indirectly) the arrangement of the tool 104 within one or more coordinate systems (e.g., the pose of the tool center point TCP within the localizer coordinate system LCLZ). Here, arrangement of the tool 104, as well as changes in arrangement of the tool 104 (e.g., movement relative to one or more trackers 160), could define system conditions SYC used by the controller to facilitate changing operation of the manipulator 102 between the first and second modes M1, M2, as described in greater detail below. In some implementations, the sensing system 206 or sensors 180 may additionally or alternatively comprise sensors 180 configured to detect electrical current from any one or more of the actuators of the joints J, sensors to detect torque or torques applied to any one or more of the joints J or joint actuators, or sensors to detect any other external (e.g., backdrive) force or torques applied to any one or more of the joints J. One example of a method for computing backdrive forces on the joints can be like that described in U.S. Pat. No. 10,327,849, entitled "Robotic System and Method for Backdriving The Same" which is incorporated by reference herein. Current measurements obtained by the sensors 180 at any one or more of the actuators of the joints J can be converted into force or torque measurements, which can be projected onto the target site TS where the tool 104 is interacting. In some examples, these force torque measurements obtained from the joints can be compared with the measurements from the six degree of freedom DOF force/torque transducer arranged to detect forces and/or torque occurring between the manipulator 102 and the target site TS or compared with state data regarding the patient or tool obtained by the navigation system. The sensing system 206 may comprise (or otherwise communicate with) various components of the surgical system 100 including, by way of non-limiting example, one or more instruments 112, joint encoders 122, controllers 124, 132, 134, 136, input devices 146, output devices 144, user interfaces 142, power generation assemblies 152, pointers 156, localizers 158, trackers 160, video cameras 170, and the like. Other configurations are contemplated.

The system conditions SYC could be defined in a number of different ways, including based on relationships between different components of the surgical system 100 and/or the target site TS. For example, the pose of the first patient tracker 160A (e.g., tracked within the localizer coordinate system LCLZ) and the pose of the tool center point TCP of the tool 104 (e.g., transformed into or tracked within the localizer coordinate system LCLZ) could each define respective system conditions SYC, and concurrent movement of the pose of the first patient tracker 160A together with the pose of the tool center point TCP could define a different system condition SYC. Accordingly, a number of different system conditions SYC are contemplated by the present disclosure, which could be defined in various ways based on changes occurring at and/or between one or more of the tool 104, the manipulator 102, and/or the target site TS.

Figure 22A:
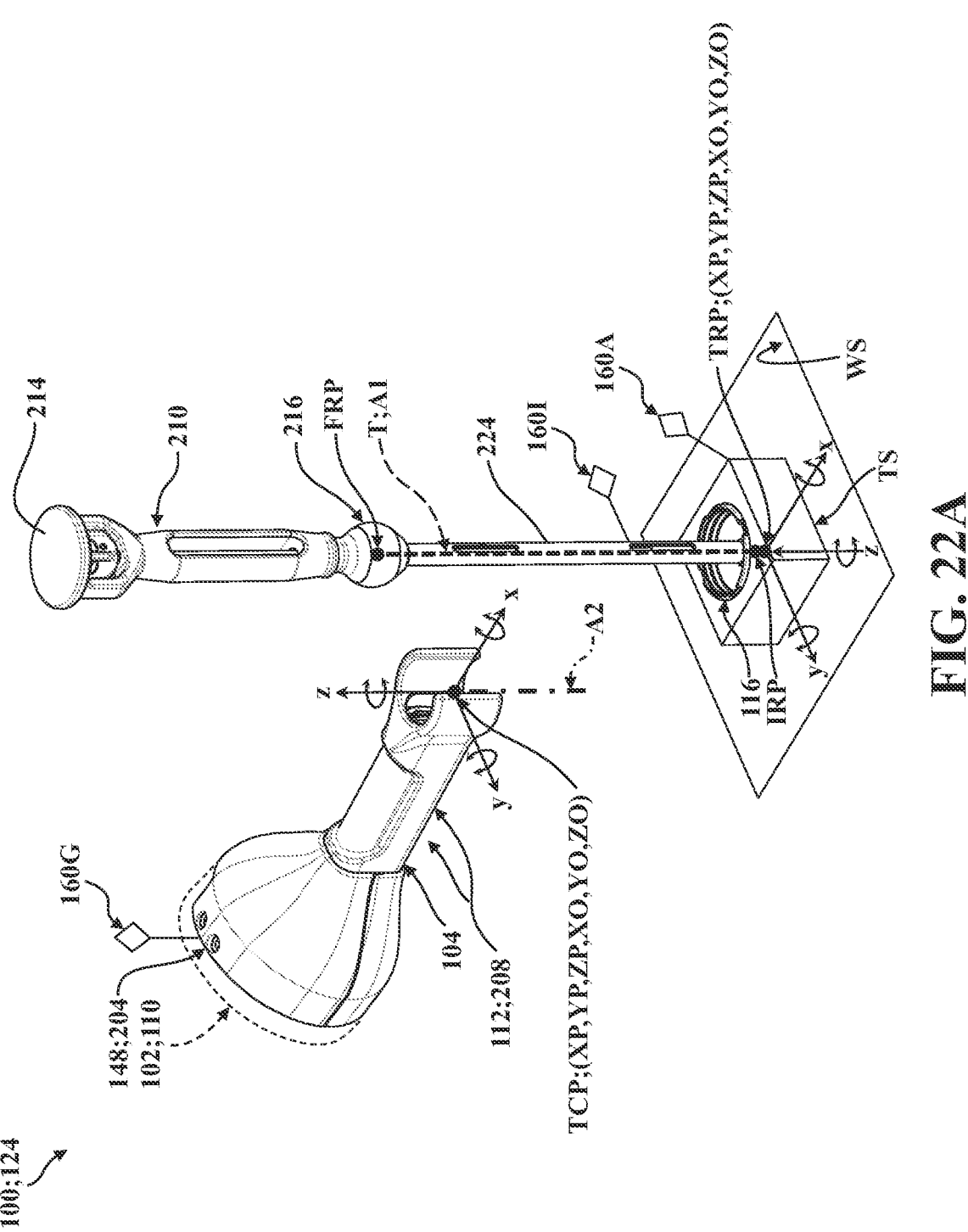
FIG. 22A is another partial perspective view of the guide, the impactor assembly supporting the prosthesis, and the target site of FIGS. 15-17B, shown with the prosthesis arranged at the target site and spaced from the guide coupled to the manipulator.

Referring now to FIG. 22A, as noted above, the controller 124 is configured to operate the manipulator 102 in the first mode M1 to maintain alignment of the tool 104 with respect to the target site TS based on the first constraint criteria C1, and to operate the manipulator 102 in the second mode M2 to maintain alignment of the tool 104 with respect to the target site TS based on the second constraint criteria C2, which is different from the first constraint criteria C1. To this end, in some embodiments, the difference between the first constraint criteria C1 and the second constraint criteria C2 may be based on the degrees of freedom DOF in which movement of the tool 104 relative to the target site TS is restricted (or permitted), as well as how movement in one or more degrees of freedom DOF could be effected (see also FIG. 25). While this concept is described in greater detail below in connection with FIGS. 24A-24C, for illustrative purposes, FIG. 22A shows the manipulator 102 supporting the instrument 112 of the tool 104 (here, the guide 208) spaced from the impactor assembly 210 secured to the implantable component 116 disposed in initial engagement with the target site TS supported on the work surface WS, with the tool center point TCP of the tool 104 and the target reference point TRP of the target site TS each shown comprising six respective degrees of freedom DOF represented in Cartesian format.

More specifically, the tool center point TCP and the target reference point TRP each define a respective x position XP degree of freedom DOF, y position YP degree of freedom DOF, z position ZP degree of freedom DOF, x orientation ZO degree of freedom DOF, y orientation YO degree of freedom DOF, and z orientation ZO degree of freedom DOF within a common coordinate system (e.g., the localizer coordinate system LCLZ or another suitable coordinate system). Here, the tool center point TCP is "fixed" relative to the tool 104 and is known by the controller 124 (e.g., based geometric relationships between the tool 104 and the coupling 110 of the manipulator 102). Similarly, the target reference point TRP is "fixed" relative to the target site TS and is known by the controller 124 (e.g., based on the tracked states of the first patient tracker 160A coupled to the target site TS and defined by reaming the acetabulum). For illustrative purposes, the tool center point TCP and the target reference point TRP are depicted as coordinate systems in FIGS. 22A-24C, with x, y, and z axes each representing two degrees of freedom DOF: translation of the coordinate system in a direction along the axis, and rotation of the coordinate system in a direction about the axis. In FIG. 22A, for illustrative purposes, the tool center point TCP is arranged with its z axis parallel to the trajectory T and with its x axis transverse to the trajectory T, and the target reference point TRP is arranged with its z axis coincident to the trajectory T.

In some embodiments, the first constraint criteria C1 may comprise a first number N1 of degrees of freedom DOF in which movement of the tool 104 is restricted relative to the target site TS, and the second constraint criteria C2 may comprise a second number N2 of degrees of freedom DOF in which movement of the tool 104 is restricted relative to the target site TS, where the second number N2 of degrees of freedom DOF is different from the first number N1 of degrees of freedom DOF. Thus, in some embodiments, the controller 124 may be configured to operate the manipulator 102 in the first mode M1 to maintain alignment of the tool 104 with respect to the target site TS based on the first number N1 of degrees of freedom DOF, and in the second mode M2 to maintain alignment of the tool 104 with respect to the target site TS based on the (different) second number N2 of degrees of freedom DOF.

Here, the first number N1 could represent the number of "active" degrees of freedom DOF which define the target state ST in the first mode M1, and the second number N2 could represent the number of "active" degrees of freedom DOF which define the target state ST in the second mode M2. For example, where the sensing system 206 comprises the sensor 180 to detect force FD occurring between the target site TS and the manipulator 102 to define the system condition SYC, in some embodiments, the controller 124 could define the target state ST based on a total of six degrees of freedom DOF (e.g., the x position XP, the y position YP, the z position ZP, the x orientation XO, the y orientation YO, and the z orientation ZO) for operating the manipulator 102 in the first mode M1, and could automatically change how the target state ST is defined to operate the manipulator 102 in the second mode M2 based on three degrees of freedom DOF (e.g., the x orientation XO, the y orientation YO, and the z orientation ZO) as soon as the force FD detected by the sensor 180 satisfies the predetermined condition PR. Here, the predetermined condition PR could be defined as the force FD detected by the sensor 180 (e.g., force and/or torque in one or more degrees of freedom DOF) that is indicative of a potential "runaway" condition defined such as by the implantable component 116 becoming "fixed" to the anatomy of the patient P at the target site TS, whereby the controller 124 effectively changes the target state ST in the second mode M2 to no longer maintain the position (e.g., the x position XP, the y position YP, and the z position ZP) of the tool center point TCP relative to the target site TS.

Thus, in some embodiments, the controller 124 may be configured to operate the manipulator 102 in the first mode M1 to restrict movement of the tool center point TCP away from the target site TS (or, the trajectory T) according to the first constraint criteria C1 (e.g., which defines the target state ST based on a target orientation OT and a target position PT) and based on the first number N1 of degrees of freedom DOF, and to operate the manipulator 102 in the second mode M2 to permit movement of the tool center point TCP away from the target site TS according to the second constraint criteria C1 (e.g., which defines the target state ST based on a target orientation OT but not a target position PT) and based on the (different) second number N2 of degrees of freedom DOF. While this illustrative example is described in greater detail below in connection with FIGS. 24A-24C, other configurations are contemplated, and the changing between modes based on satisfying the predetermined condition PR could occur in a number of different ways, based on various system conditions SYC determined via the sensing system 206.

In some embodiments, the second number N2 of degrees of freedom DOF is smaller than the first number N1 of degrees of freedom DOF such that the controller 124 permits movement of the tool 104 relative to the target site TS in at least one more degree of freedom DOF in the second mode M2 than in the first mode M1. Here too, in some embodiments, the first constraint criteria C1 and the second constraint criteria C2 may each comprise at least one orientational degree of freedom DOF (e.g., the x orientation XO, the y orientation YO, and/or the z orientation ZO), the first constraint criteria C1 may comprise at least one more positional degree of freedom DOF (e.g., the x position XP, the y position YP, and/or the z position ZP) than the second constraint criteria C2, and both the first constraint criteria C1 and the second constraint criteria C2 may comprise at least one common degree of freedom DOF (e.g., the x orientation XO, the y orientation YO, and/or the z orientation ZO). Furthermore, in some embodiments, the first constraint criteria C1 may comprise at least one positional degree of freedom DOF (e.g., the x position XP, the y position YP, and/or the z position ZP) and at least one orientational degree of freedom DOF (e.g., the x orientation XO, the y orientation YO, and/or the z orientation ZO). However, as will be appreciated from the subsequent description below, other configurations are contemplated, and the first criteria C1 and/or the second constraint criteria C2 could be defined in a number of different ways depending, for example, on the type of surgical procedure being performed at the target site TS, the specific arrangement and configuration of the tool 104 (and/or the energy applicator 114 or the implantable component 116), how the tool 104 is arranged by the manipulator 102 relative to the target site TS, and the like.

In some embodiments, the first constraint criteria C1 may comprise a first resilience parameter R1, and the second constraint criteria C2 may comprise a second resilience parameter R2 different from the first resilience parameter R1. Thus, in some embodiments, the controller 124 may be configured to operate the manipulator 102 in the first mode M1 to maintain alignment of the tool 104 with respect to the target site TS based on the first resilience parameter R1, and in the second mode M2 to maintain alignment of the tool 104 with respect to the target site TS based on the (different) second resilience parameter R2. Here, the first resilience parameter R1 could represent or otherwise correspond to tuning parameters TPA (e.g., spring parameters PS and/or damping parameters PD) of one or more guide constraints GC which define the first mode M1, and the second resilience parameter R2 could represent or otherwise correspond to tuning parameters TPA (e.g., spring parameters PS and/or damping parameters PD) of one or more guide constraints GC which define the second mode M2. As will be appreciated from the subsequent description below, the first constraint criteria C1 and/or the second constraint criteria C2 may be configured or defined in a number of different way including, by way of non-limiting example, where resilience parameters are defined for each "active" degree of freedom DOF while operating in either the first mode M1 or the second mode M2. Put differently, the first constraint criteria C1 could comprise three "active" degrees of freedom DOF each having a respective first resilience parameter, which may be the same or could be different from each other. Other configurations are contemplated.

In some embodiments, the controller 124 may be configured to permit more resilient movement of the tool 104 relative to the target site TS in the second mode M2 than in the first mode M1. Put differently, the second resilience parameter R2 could be less "stiff" than the first resilience parameter R1 such that deviation from the target state ST is more difficult in the first mode M1 than in the second mode M2. However, other configurations are contemplated. In some embodiments, the first resilience parameter R1 and the second resilience parameter R2 are each associated with resilient movement of the tool 104 relative to the target site TS in at least one common degree of freedom DOF (e.g., in the x position XP, the y position YP, the z position ZP, the x orientation XO, the y orientation YO, or the z orientation ZO). By way of non-limiting example, the z orientation ZO degree of freedom DOF could be "active" and form part of both the first constraint criteria C1 and the second constraint criteria C2, with the first and second resilience parameters R1, R2 each being associated with the z orientation ZO degree of freedom DOF.

In some embodiments, the first constraint criteria C1, the second constraint criteria C2, and/or the predetermined condition PR may be adjustable and/or configurable by the user, such as via the user interface 142. To this end, a threshold control 314 (see FIG. 2; see also FIG. 25) may be provided to facilitate adjusting how the predetermined condition PR is defined. By way of example, the threshold control 314 could be configured as an input device 146 which changes the amount of force FD detected by the sensor 180 (e.g., a system condition SYC) that is required to satisfy the predetermined condition PR, such as to require more or less force FD to be detected (e.g., force and/or torque in a particular direction) before the controller 124 will change from the first mode M1 to the second mode M2. By way of further example, the threshold control 314 could be configured as an input device 146 which changes the amount of time that the tool 104 and the target site TS move together for (e.g., as determined via the navigation system 128) in order to satisfy the predetermined condition PR, such as to require concurrent movement for more or less time before the controller 124 will change from the first mode M1 to the second mode M2. The examples provided above are illustrative and non-limiting, and other configurations are contemplated.

In some embodiments, a stiffness control 316 (see FIG. 2; see also FIG. 25) may be provided to facilitate adjusting how the first constraint criteria C1 (or, in some embodiments, the second constraint criteria C2) is defined. By way of example, the stiffness control 316 could be configured as an input device 146 which changes the tuning parameters TPA and/or the configuration parameters CPA of one or more of the guide constraints GC used to define the first mode M1 (e.g., to facilitate maintaining the target state ST), such as by increasing or decreasing the first resilience parameter R1 to result in a corresponding change in how the manipulator 102 restricts movement from the target state ST (e.g., with less or more "stiffness"). Here too, the forgoing example is illustrative and non-limiting, and other configurations are contemplated.

In other implementations, the first constraint criteria C1 or the second constraint criteria C2 can be dynamically determined or adjusted based on measurements from the sensing system or sensor 180. The controller can correlate the magnitudes or values of the sensed measurements to stiffness values, e.g., using a look-up table stored in memory. This technique can be implemented with a threshold as described above, or without regard to any threshold.

In some embodiments, the surgical system 100 also comprises a mode indicator 318 (see FIG. 2; see also FIG. 25) coupled to the controller 124 to communicate a change in operation of the manipulator 102 from the first mode M1 to the second mode M2 (or between other modes). Here, the mode indicator 318 may form part of the user interface 142 (e.g., as an alarm, a speaker, an indicator light, a part of a display screen, and/or another type of output device 144), and the controller 124 could be configured to activate the mode indicator 318 in response to determining that at least one of the one or more system conditions SYC satisfies the predetermined condition PR.

As noted above, FIG. 22A shows the manipulator 102 supporting the instrument 112 of the tool 104 (here, the guide 208) spaced from the impactor assembly 210 secured to the implantable component 116 disposed in initial engagement with the target site TS supported on the work surface WS, with the tool center point TCP of the tool 104 and the target reference point TRP of the target site TS spaced from each other. Comparing FIG. 22A with FIG. 22B illustrates movement of the tool 104 in the x position XP degree of freedom DOF (e.g., in a direction along the x axis of the tool center point TCP), whereby the shaft 224 of the impactor assembly 210 has passed through the opening 268 of the guide 208 and into the channel 262 to bring the tool center point TCP onto the trajectory T (and also onto the z axis of the target reference point TRP).

Comparing FIG. 22B with FIG. 22C illustrates movement of the tool 104 in the z position ZP degree of freedom DOF (e.g., in a direction along the z axis of the tool center point TCP), whereby the flange 216 of the impactor assembly 210 has become disposed within the channel 262 of the guide

208, with the first engagement surface 218 abutting the second engagement surface 270, and with the tool center point TCP arranged coincident to the flange reference point FRP and still disposed along the trajectory T.

In some embodiments, the controller 124 may be configured to operate the manipulator 102 in the second mode M2 to permit movement of the tool 104 relative to the target site TS in at least one degree of freedom DOF according to the second constraint criteria C2. Similarly, in some embodiments, the controller 124 may be configured to operate the manipulator 102 in the first mode M1 to permit movement of the tool 104 relative to the target site TS in at least one degree of freedom DOF according to the first constraint criteria C1. Here, for example, comparing FIG. 22C with FIG. 23 illustrates movement of the tool 104 in the z orientation ZO degree of freedom DOF (e.g., in a direction about the z axis of the tool center point TCP), whereby the guide 208 has moved relative to the impactor assembly 210 and the target site TS from the arrangement depicted in FIG. 22C (depicted as a phantom outline in FIG. 23), but the tool center point TCP of the tool 104 remains arranged coincident to the flange reference point FRP and is likewise disposed along the trajectory T.

Put differently, the movement of the tool 104 illustrated by comparing FIGS. 22C-23 could represent a scenario where the first constraint criteria C1 comprises five active degrees of freedom DOF (e.g., the x position XP, the y position YP, the z position ZP, the x orientation XO, and the y orientation YO) and permits movement in one degree of freedom DOF (e.g., the Z orientation ZO) to define the target state ST while operating in the first mode M1. This configuration could, for example, be implemented in order to allow the user to "rotate" the guide 208 about the trajectory T (e.g., between mallet strikes to the head 214 of the impactor assembly 210) to a different arrangement that is maintained by the manipulator 102 (e.g., by re-defining the target state ST based on the wherever the guide 208 was positioned by the user).

However, the first constraint criteria C1 could be configured in a number of different ways to define the target state ST while operating in the first mode M1. For example, rather than permitting the user to adjust the orientation of the guide 208 about the trajectory T in the first mode M1 in such a way that the manipulator 102 re-defines the target state ST based on the user "rotating" the guide 208 about the trajectory T, the first constraint criteria C1 could instead be configured to define the target state ST in all six degrees of freedom DOF while permitting more resilient movement (e.g., less "stiff" movement) in one or more degrees of freedom DOF than in others. By way of illustrative example, the arrangement depicted in FIG. 22C could instead represent the target state ST in the first mode M1, with the first constraint criteria C1 configured such that the first resilience parameter R1 associated with the z orientation ZO degree of freedom DOF has a relatively "weak" value that permits the user to "rotate" the guide 208 about the trajectory T as shown in FIG. 23 but nevertheless urges the tool 104 toward the target state ST. Here in this example, the arrangement of the tool 104 depicted in FIG. 23 would represent a current state SC, with the target state ST shown as a phantom outline (see also FIG. 22C).

Figure 24B:
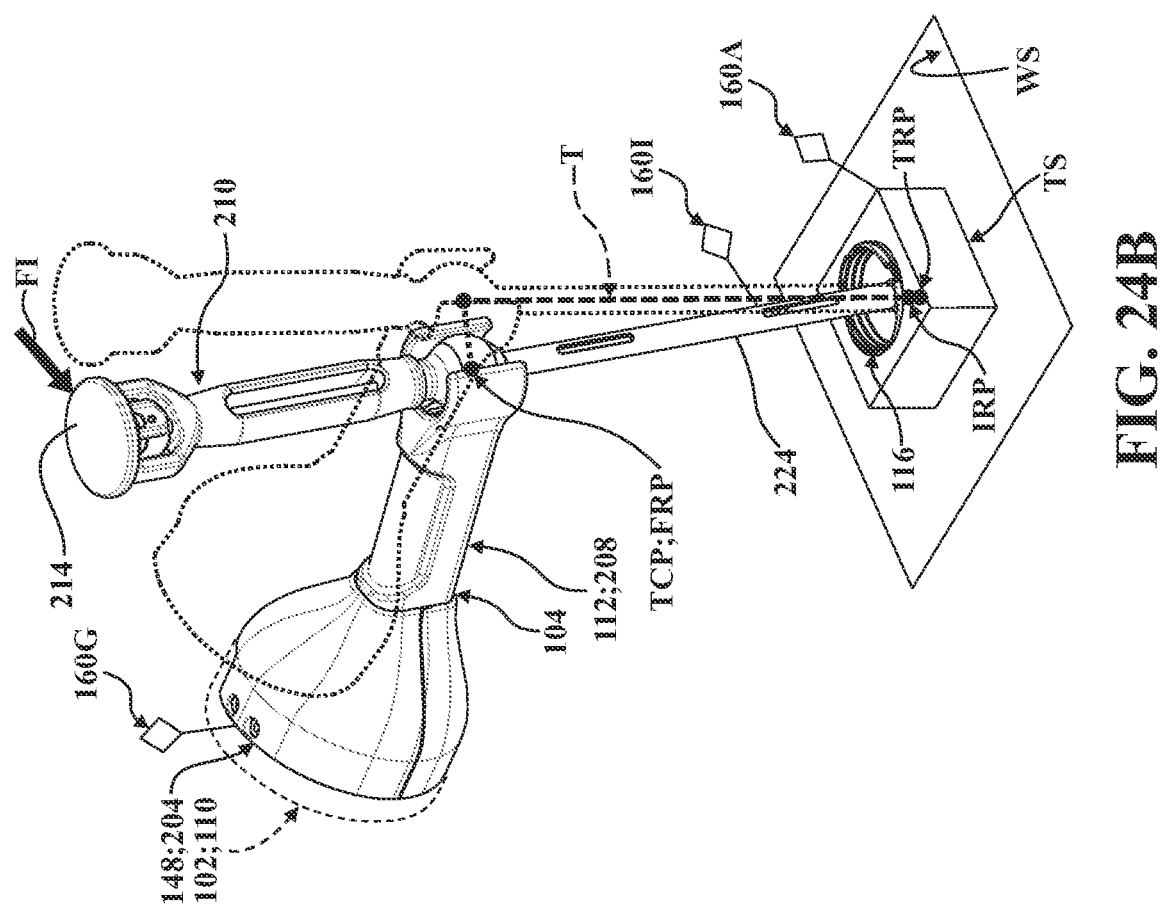
FIG. 24B is another partial perspective view of the guide, the impactor assembly supporting the prosthesis, and the target site of FIG. 24A, shown with the prosthesis partially implanted at the target site and misaligned relative to the trajectory in response to the applied force illustrated in FIG. 24A, and with the tool and the prosthesis arranged in exaggerated misalignment relative to the trajectory and relative to a previous arrangement depicted in phantom.
Figure 24C:
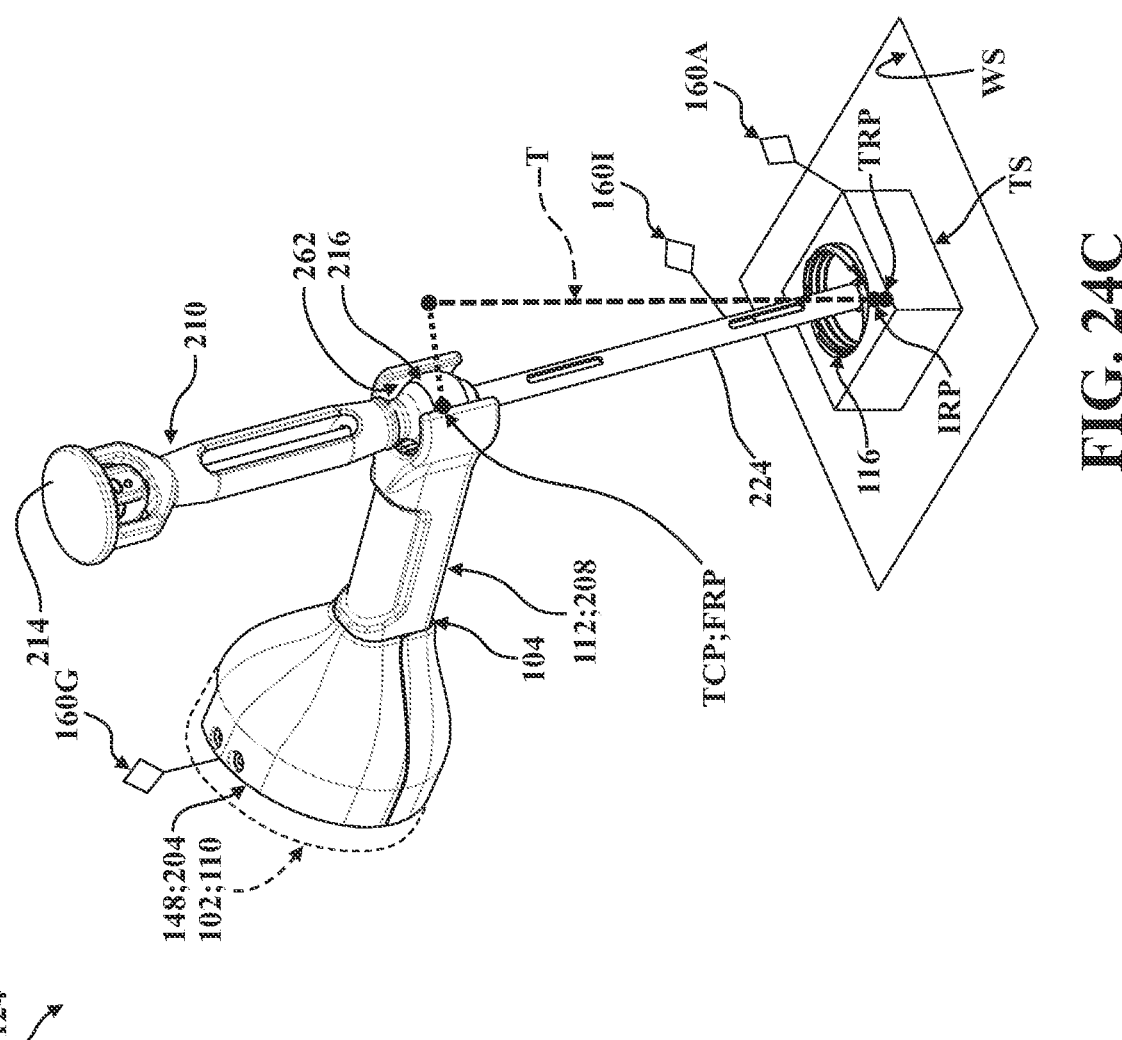
FIG. 24C is another partial perspective view of the guide, the impactor assembly supporting the prosthesis, and the target site of FIG. 24B, shown with the prosthesis partially implanted at the target site and further misaligned relative to the trajectory in response to the applied force illustrated in FIG. 24A, and with the tool and the prosthesis arranged in further exaggerated misalignment relative to the trajectory.

Referring now to FIGS. 24A-24C, in some embodiments, the controller 124 may be further configured to operate the manipulator 102 in a third mode M3 to maintain alignment of the tool 104 with respect to the target site TS according to a third constraint criteria C3 different from both the first constraint criteria C1 and the second constraint criteria C2.

Here in this embodiment, the controller 124 is configured to change operation of the manipulator 102 from the first mode M1 to the second mode M2 in response to determining that at least one of the one or more system conditions SYS satisfies a first predetermined condition PR1, and to change operation of the manipulator 102 from the second mode M2 to the third mode M3 in response to determining that at least one of the one or more system conditions SYS satisfies a second predetermined condition PR2 different from the first predetermined condition PR1. Here in this illustrative embodiment, the first constraint criteria C1 comprises a first number N1 of degrees of freedom DOF in which movement of the tool 104 is restricted relative to the target site TS, the second constraint criteria C2 comprises a second number N2 of degrees of freedom DOF in which movement of the tool 104 is restricted relative to the target site TS, and the third constraint criteria C3 comprises a third number N3 of degrees of freedom DOF in which movement of the tool 104 is restricted relative to the target site TS. Furthermore, in this illustrative embodiment, the first constraint criteria C1 also comprises a first resilience parameter R1, the second constraint criteria C2 also comprises a second resilience parameter R2, and the third constraint criteria C3 also comprises a third resilience parameter R3.

Thus, in the representative embodiment illustrated in connection with FIGS. 24A-24C, the controller 124 is configured to operate the manipulator 102: in the first mode M1 to maintain alignment of the tool 104 with respect to the target site TS based on the first number N1 of degrees of freedom DOF and also based on the first resilience parameter R1; in the second mode M2 to maintain alignment of the tool 104 with respect to the target site TS based on the second number N2 of degrees of freedom DOF and also based on the second resilience parameter R2; and in the third mode M3 to maintain alignment of the tool 104 with respect to the target site TS based on the third number N3 of degrees of freedom DOF and also based on the third resilience parameter R3. Here, the third number N3 of degrees of freedom DOF is different from one or more of the first number N1 of degrees of freedom DOF and the second number N2 of degrees of freedom DOF. More specifically, in this embodiment, the third number N3 of degrees of freedom DOF is smaller than the first number N1 of degrees of freedom DOF such that the controller 124 permits movement of the tool 104 relative to the target site TS in at least one more degree of freedom DOF in the third mode M3 than in the first mode M1. Similarly, in this embodiment, the third number of degrees of freedom DOF is smaller than the second number N2 of degrees of freedom DOF such that the controller 124 permits movement of the tool 104 relative to the target site TS in at least one more degree of freedom DOF in the third mode M3 than in the second mode M2.

More specifically, in this representative embodiment, the first number N1 of degrees of freedom DOF is equal to the second number N2 of degrees of freedom DOF, both of which are different from the third number N3 of degrees of freedom DOF. However, other configurations are contemplated. Here in this embodiment, the difference between the first constraint criteria C1 and the second constraint criteria C2 is based on the first and second resilience parameters R1, R2 as described in greater detail below, rather than on the first and second number N1, N2 of degrees of freedom DOF that are "active" in the first and second modes M1, M2.

In some embodiments, such as the embodiment illustrated in connection with FIGS. 24A-24C, the first constraint criteria C1 and the second constraint criteria C2 each comprise at least one positional degree of freedom DOF (e.g., the x position XP, the y position YP, and/or the z position ZP) and at least one orientational degree of freedom DOF (e.g., the x orientation XO, the y orientation YO, and/or the z orientation ZO); and each of the first constraint criteria C1, the second constraint criteria C2, and the third constraint criteria C3 comprise at least one orientational degree of freedom (e.g., the x orientation XO, the y orientation YO, and/or the z orientation ZO). Here too, the first constraint criteria C1 and the second constraint criteria C2 each comprise at least one more positional degree of freedom DOF than the third constraint criteria C3. However, other configurations are contemplated.

As noted above, in the representative embodiment illustrated in FIGS. 24A-24C, the difference between the first constraint criteria C1 and the second constraint criteria C2 is based on the first and second resilience parameters R1, R2 rather than on the first and second number N1, N2 of degrees of freedom DOF which are "active" in the first and second modes M1, M2. Here, the third resilience parameter R3 is different from one or more of the first resilience parameter R1 and the second resilience parameter R2, which are also different from each other in this embodiment. More specifically, and as is described in greater detail below, the controller 124 permits more resilient movement (e.g., less "stiff" movement) of the tool 104 relative to the target site TS in the second mode M2 than in the first mode M1, and permits more resilient movement (e.g., less "stiff" movement) of the tool 104 relative to the target site TS in the second mode M2 than in the third mode M3. Here too, the forgoing is intended to be a non-limiting example, and other configurations of the surgical system 100 are contemplated.

In FIG. 24A, the controller 124 is operating the manipulator 102 in the first mode M1 according to the first constraint criteria C1 which, in this representative embodiment, defines the target state ST as illustrated, with the tool 104 arranged such that there is coincident alignment of the axes A1, A2 with the trajectory T as noted above. To this end, the first constraint criteria C1 comprises both the first number N1 of degrees of freedom DOF and the first resilience parameter R1. For the purposes of this illustrative example, the first number N1 comprises six "active" degrees of freedom DOF: the x position XP, the y position YP, the z position ZP, the x orientation XO, the y orientation YO, and z the orientation ZO. Furthermore, in this illustrative example, the first resilience parameter R1 is set such that the tool 104 is maintained in the target state ST with a relatively "stiff haptic," defined for example by tuning parameters TPA of guide constraints GC where the spring parameters PS are set relatively high to resist movement in each of the six active degrees of freedom DOF.

With continued reference to FIG. 24A, impaction force FI is shown being improperly applied to the head 214 of the impactor assembly 210 (e.g., transverse to the trajectory T). Here, the improper application of impact force FI (e.g., relatively high in magnitude and/or misaligned with the trajectory T) may result in the implantable component 116 becoming partially-seated into the target site TS in a way that is misaligned with the trajectory T, such as is depicted in FIG. 24B with exaggerated misalignment between axes A1, A2 and the trajectory T for illustrative purposes. Here in FIG. 24B, the sensor 180 detects force FD between the target site TS and the manipulator 102 resulting from the deviation of the illustrated current state SC from the target state ST (depicted here in phantom outline), with the sensor 180 serving as part of the sensing system 206 to detect system condition SYC (e.g., the force FD). In this scenario, rather than continuing to move the manipulator 102 so as to bring the tool 104 to the target state ST (e.g., by moving the tool center point TCP back onto the trajectory T), the controller 124 changes from the first mode M1 to the second mode M2 in response to the force FD detected by the sensor 180 having satisfied the first predetermined condition PR1 which, in this embodiment, is defined as a first force F1 detected by the sensor 180 (e.g., force and/or torque in one or more degrees of freedom DOF). Thus, FIG. 24B depicts operation of the manipulator 102 in the second mode M2 according to the second constraint criteria C2.

In FIG. 24B, the controller 124 is operating the manipulator 102 in the second mode M2 according to the second constraint criteria C2, with the target state ST still being defined by the arrangement depicted in FIG. 24A (shown in FIG. 24B as a phantom outline). Here, the second constraint criteria C2 comprises the second number N2 of degrees of freedom DOF and the second resilience parameter R2. For the purposes of this illustrative example, the second number N2 comprises six "active" degrees of freedom DOF: the x position XP, the y position YP, the z position ZP, the x orientation XO, the y orientation YO, and z the orientation ZO. However, in this illustrative example, the second resilience parameter R2 is set such that the tool 104 is urged toward the target state ST with a relatively "loose haptic" (e.g., the second resilience parameter R2 is smaller than the first resilience parameter R1), defined for example by tuning parameters TPA of guide constraints GC where the spring parameters PS are set relatively low to permit a certain amount of resilient movement in each of the six active degrees of freedom DOF. With this configuration, the manipulator 102 is still attempting to return to the target state ST (e.g., by bringing the tool center point TCP back onto the trajectory T), but the "loose haptic" afforded by the second constraint criteria C2 permits a certain amount of deviation from the target state ST to occur, thereby preventing a "runaway" condition when the implantable component 116 is partially-seated into the target site TS while misaligned, and keeping the target site TS supported on the work surface WS.

With continued reference to FIG. 24B, additional impaction force FI is shown being improperly applied to the head 214 of the impactor assembly 210 (e.g., transverse to the trajectory T). Here, the improper application of impact force FI (e.g., relatively high in magnitude and/or misaligned with the trajectory T) may still result in the implantable component 116 becoming seated further into the target site TS in a way that is further misaligned with the trajectory T, such as is depicted in FIG. 24C with exaggerated misalignment between the axes A1, A2 and the trajectory T for illustrative purposes. Here in FIG. 24C, the sensor 180 similarly detects force FD between the target site TS and the manipulator 102 resulting from the further deviation of the illustrated current state SC from the target state ST (depicted here as an endpoint of the trajectory T). Here too in this scenario, rather than continuing to move the manipulator 102 so as to bring the tool 104 to the target state ST (e.g., by moving the tool center point TCP back onto the trajectory T), the controller 124 changes from the second mode M2 to the third mode M3 in response to the force FD detected by the sensor 180 having satisfied the second predetermined condition PR2 which, in this embodiment, is defined as a second force F2 detected by the sensor 180 (e.g., force and/or torque in one or more degrees of freedom DOF) where the second force F2 is larger than the first force F1. In some embodiments, the second force F2 may be smaller than an amount of force and/or torque acting on the target site TS in one or more directions via engagement with the implantable component

116 that could otherwise "unseat" the partially or fully-seated implantable component 116.

In FIG. 24C, the controller 124 is operating the manipulator 102 in the third mode M3 according to the third constraint criteria C3, with the target state ST still being defined by the arrangement depicted in FIG. 24A (shown in FIG. 24C as an endpoint of the trajectory T). Here, the third constraint criteria C3 comprises the third number N3 of degrees of freedom DOF and the third resilience parameter R3. For the purposes of this illustrative example, the third number N3 comprises three "active" degrees of freedom DOF: the x orientation XO, the y orientation YO, and z the orientation ZO. Put differently, no positional degrees of freedom DOF are active according to the third constraint criteria C3. Here in this illustrative example, the third resilience parameter R3 is set such that the tool 104 is urged toward the target state ST with a relatively "stiff haptic," defined for example by tuning parameters TPA of guide constraints GC where the spring parameters PS are set relatively high to resist movement in each of the three active degrees of freedom DOF. Here, the tool 104 is urged toward the target state ST based on orientation but not position. With this configuration, the manipulator 102 is still attempting to return to the target state ST (e.g., by orientating the tool center point TCP toward the target site TS), but the lack of active positional degrees of freedom DOF prevents a "runaway" condition from occurring when the implantable component 116 is further seated into the target site TS while misaligned, and the target site TS similarly remains supported on the work surface WS. Here, the surgeon or another user may be alerted to the change to the third mode M3 via the mode indicator 318 which, as noted above, may form part of one or more of the user interfaces 142. By way of non-limiting example, when the controller 124 switches from the first mode M1 to the second mode M2, a "low level" alert (e.g., a sound played on a speaker, a warning displayed by a flashing light or graphic presented on a screen, and the like) could be generated to alert the user, and when the controller 124 switches from the second mode M2 to the third mode M2 (or from the first mode M1 to the third mode M3), a different or "high level" alert could be generated to alert the user. The alerts could be defined in a number of different ways sufficient to differentiate each other (e.g., one being visual and the other being audible, or combinations thereof) and, as noted above, the mode indicator 318 could be of a number of different styles, types, and/or configurations.

While the representative embodiment described above in connection with FIGS. 24A-24C employs three constraint criteria C1, C2, C3, three modes M1, M2, M3, and two predetermined conditions PR1, PR2, similar functionality could be afforded with two modes and one predetermined condition PR in some embodiments. By way of non-limiting example, when utilizing the sensor 180 to monitor system conditions SYC where the predetermined condition PR is defined as the detected force FD (e.g., force and/or torque in one or more degrees of freedom DOF), with the controller 124 configured to switch from the first mode M1 (e.g., to maintain six degrees of freedom DOF according to a first constraint criteria C1) to the second mode M2 (e.g., to maintain only orientational degrees of freedom DOF according to a second constraint criteria C2), the controller 124 could be configured to operate the manipulator 102 in the first mode M1 to resist movement of the tool 104 relative to the target site TS with increasing resilience as the force FD detected by the sensor 180 increases toward the predetermined condition PR. Put differently, rather than FIG. 24B depicting operation in a different mode than what is depicted in FIG. 24A, FIG. 24B could instead represent a part of the same mode (e.g., the first mode M1) where the first constraint criteria C1 comprises a resilience parameter that is defined as a function of the force FD detected by the sensor 180 until, for example, the detected force FD satisfies the predetermined condition PR (e.g., where the force FD exceeds the second force F2 described above in connection with FIG. 24C). However, the forgoing example is illustrative and non-limiting, and other configurations are contemplated.

In embodiments which utilize the sensor 180 as a part of the sensing system 206 to facilitate changing between modes (e.g., the first mode M1 and the second mode M2), the sensor 180 may be further defined as a force-torque sensor 180 that is configured to detect, in one or more degrees of freedom DOF, force FD (e.g., force and/or torque) occurring between the manipulator 102 and the target site TS. To this end, and as is depicted generically in FIGS. 1 and 15, the sensor 180 may be coupled to the robotic arm 108 (e.g., as a part of the coupling 110). However, the sensor 180 could be arranged in any suitable way sufficient to detect force FD occurring between the manipulator 102 and the target site TS, and could be of a number of different types, styles, or configurations without departing from the scope of the present disclosure. By way of non-limiting example, the sensor 180 could be realized as a part of the coupling 110, as a part of the robotic arm 108 (e.g., arranged at one of the joints), and/or as a part of the tool 104 (e.g., arranged at the instrument 112 and/or at the implantable component 116). Similarly, the sensor 180 could be arranged at the mount 148 and/or the body 260 of the guide 208. Moreover, while the representative embodiment illustrated herein is directed toward a single, multiple degree of freedom DOF force-torque transducer that is coupled to the manipulator 102, the sensor 180 could also be realized by multiple components, arranged in the same location or in different locations (e.g., one at the guide 208 and one at the coupling 110), which cooperate to facilitate detecting force FD occurring between the target site TS and the robotic arm 108. Other configurations are contemplated.

In some embodiments, the amount of force FD detected by the sensor 180 which satisfies the predetermined condition PR (e.g., the first force F1, the second force F2, or other values) either represents or is based on the amount of torque (or force) being applied at the implantable component 116. Here, the known properties of the tool 104 and the implantable component 116 can be used to relate force/torque at the sensor 180 to the force/torque applied at the implantable component 116. Calculating the rigid body Jacobian from the sensor 180 to the implantable component 116 may be performed according to $F_{IMPLANT} = J_{SENSOR\_TO\_IMPLANT}{}^{-T} \cdot {}^{T*}F_{SENSOR}$. The force FD detected by the sensor 180 could define the predetermined condition PR in a number of different ways, and may be application and/or procedure specific. In some embodiments, the type, style, size, or other parameters of the implantable component 116 could at least partially define one or more predetermined conditions PR. Here, for example, a relatively "large" implantable component 116 may require a different amount of torque (or force) applied thereto before becoming unseated at the target site TS in comparison to a relatively "small" implantable component 116. The specific parameters of the predetermined condition PR based on the sensor 180 (e.g., the magnitude of force and/or torque in one or more degrees of freedom DOF) could be determined in other ways, including using by performing experiments. For example, in determining the baseline force at which to start to release the translational constraint on the impaction assembly 210, lever-out torques were analyzed for acetabular cups. By knowing an approximate torque at which a well-fixed cup 116 would likely move or de-seat, cup placement accuracy can be optimized while avoiding cup lever-out by releasing the constraint at a specified limit or range. With a range of approximately 5 to 25 Nm of lever-out strength of the cup 116, the possible force limits at the impaction assembly 210 could range from 20 N to 100 N (assuming 0.25 m lever arm from end effector attachment to cup center) to address different cup fixation scenarios. In one implementation, the amount of force FD to satisfy the predetermined condition PR per lab evaluation is approximately 64 N (approximately 16 Nm lever out torque). However, other values or ranges of values are contemplated or possible depending on cup types, press-fits, testing methods and materials. In other examples, the amount of force FD to satisfy the predetermined condition PR is between 58-66 N, 50-70 N, or 40-80 N or any values in between these ranges.

In some embodiments, the threshold control 314 (and/or the stiffness control 316) could be manually-adjusted by the user intraoperatively based on subjective considerations, observations, and the like (e.g., a certain predetermined condition PR is adjusted higher or lower based on user preference). In some embodiments, the predetermined condition PR may be based on patient-specific data (e.g., height, weight, age, bone density, body-mass-index BMI, and the like) that can be entered using an input device 146 of the user interface 142. In some embodiments, the predetermined condition PR may be at least partially determined intraoperatively, such as by a "wiggle test" similar to as is described in U.S. Patent Application Publication No. US 2015/0094736 A1, entitled "System and Method of Controlling a Robotic System for Manipulating Anatomy of a Patient During a Surgical Procedure," the disclosure of which is hereby incorporated by reference in its entirety. However, other configurations are contemplated.

In other implementations, the first constraint criteria C1 or the second constraint criteria C2 can be dynamically determined or adjusted based on measurements from the sensing system or sensor 180. The controller can correlate the magnitudes or values of the sensed measurements to stiffness values, e.g., using a look-up table stored in memory. This technique can be implemented with a threshold as described above, or without regard to any threshold.

As noted above, the functionality afforded by the surgical system 100 in switching between the first and second modes M1, M2 (and/or other modes) could be carried out using other components of the sensing system 206 besides (and/or in addition to) the sensor 180. By way of non-limiting example, and referring again to FIGS. 24A-24C, the localizer 158 and one or more trackers 160 (e.g., the first patient tracker 160A and the second tool tracker 160I) could be utilized to monitor system conditions SYC such as concurrent movement of the target site TS with the impactor assembly 210 in ways that satisfy predetermined conditions PR. Here, movement which satisfies one or more predetermined conditions PR could be based on various combinations of duration and direction, such as movement which suggests that the impactor assembly 210 is fixed" to the target site TS with misalignment between the first axis A1 and the trajectory T, movement which suggests that the target site TS is being lifted off of the work surface WS or is otherwise moving in an unintended direction, and the like. Here, combinations of components of the sensing system 206 could be used together such that satisfying predetermined conditions PR to effect changing between modes M1, M2 requires multiple predetermined conditions PR to be satisfied based on the same or different types of system conditions SYC. By way of non-limiting example, the sensor 180 could be used to detect when the user is applying impact force FI, and could change how the predetermined conditions PR are defined for a period of time encompassing the impaction event, such as to briefly interpret movement of the target site TS via the first patient tracker 160A in a different way during impaction to prevent false detection of a "runaway" condition as the target site TS initially reacts to the application of impact force FI. Other configurations are contemplated.

The surgical system 100 can detect impact forces FI (or off-axis forces) and ignore or disregard such impact forces FI for the runaway condition control algorithm. In doing so, the surgical system 100 can identify that the event is an expected impact force FI and not an undesired "runaway" condition. In turn, the surgical system 100 can determine that there is no need to control the manipulator according to the second mode M2. In one example to distinguish between runaway condition and impact forces FI, the system 100 analyzes X and Y component force signals from the force torque sensor 180. The Z-component force was disregarded because the Z-axis force is not constrained in the mechanical design. To detect a runaway condition, in one implementation, the system 100 can average magnitude force over a certain duration of time (125 ms as an example) of X and Y axis forces combined and determine if this average magnitude force is greater than a force threshold. A standard deviation over that same duration can be computed to determine if the same is below a threshold. If the threshold is satisfied, then the system 100 can determine that the runaway condition exists. In one experiment, example force deviations in the X and Y directions in the runaway condition were in the range of +/−10-60 N. There may be other manners of determining that the runaway condition exists. For example, the measured X and Y forces can be individually compared to threshold limits over time. Other factors can be considered when determining thresholds for detecting the runaway conditions.

On the other hand, to detect the impaction force FI (as compared with a runaway condition), the X, Y and Z components of force as obtained by the sensor 180 can be analyzed by the sensing system 100 over a period of time (e.g., 30-60 seconds) during which impaction occurs. In one example, the majority of the forces during the impaction event occur in the Z-direction due to the mechanical nature of the assembly. However, X and Y forces occur depending on the manner or accuracy in which a user hits the impactor. During this period of time, each of the X, Y and Z components produce individual signal spikes indicative of each impact. The sensing system 100 can isolate each of the signal spikes indicative of each impaction. In one example, each signal spike was experimentally determined to last for a duration within the range of 100-150 ms. The sensing system 100 can then compute the duration of each impaction event and compute a standard deviation during that computed duration. From there, a threshold is set to define the impaction event. If the threshold is satisfied, then the system 100 can determine that the impact event occurred. In one experiment, example force deviations in the X and Y directions in response to impaction events were in the range of +/−10-30 N and example force deviations in the Z direction in response to impaction events were in the range of +/−20-40 N. There may be other manners of determining that the impaction event occurs. For example, the measured forces can be individually compared to thresholds over time. Also, thresholds for detecting the runaway conditions can vary depending on factors such as cup type, cup size, patient data, impactor parameters, expected impaction forces or the like. By being able to filter between runaway and impact events, the system 100 can intelligently modify the constraint criteria only when needed to counteract runway condition.

Furthermore, combining different types of predetermined conditions PR to be satisfied before changing between modes M1, M2 could also be implemented with other types of tools 104, such as the powered surgical device 150 described above in connection with FIGS. 12-14D. For example, predetermined conditions PR associated with system conditions SYC defined by operation of the power generation assembly 152 (e.g., motor speed, load, and the like) could be compared against predetermined conditions PR associated with system conditions SYC defined by the navigation system 128, the sensor 180, and the like, such as to avoid changing between modes M1, M2 if the energy applicator 114 is still rotating even where there is concurrent movement of the tool 104 and the target site TS that would otherwise cause the controller 124 to change between modes M1, M2. Here too, the example provided above is intended to be illustrative and non-limiting, and other configurations are contemplated.

In one example, and with reference to FIG. 26, the "runaway" condition may exist in a situation where a tool 104, such as a tool having a bur 154 as the energy applicator 114, engages with the target site TS bone while being constrained by a virtual boundary 174 associated with the target site TS. More specifically, the runaway condition may exist if the bur 154 becomes trapped, disposed, or wedged between the virtual boundary 174 and the target site TS bone. As a result of this situation, the bur 154 can be pushed partially outside of the virtual boundary 174. Because the virtual boundary 174 is configured to constrain tool 104 motion, the system controls the manipulator to apply a reactive force RF to the bur 154. This reactive force RF causes the bur 154 push against the target site TS bone causing the target site TS bone to move. The target site TS is tracked by the navigation system through tracker 160A. Therefore, the pushing of the target site TS will cause a corresponding movement of the associated virtual boundary 174, in turn causing the reactive force RF to persist to the runaway condition. Implementations of the systems, methods and techniques described above can be fully applied to prevent this scenario. In this example, the first constraint criteria C1 and second constraint criteria C2 can be like any of those described above to prevent the runaway condition. Additionally or alternatively, the constraint criteria C1, C2 may relate to a magnitude or direction of the reactive force RD, a stiffness or damping parameter associated with the reactive force RF, a shape of the virtual boundary 174, a flexibility of the virtual boundary 174, a stiffness or damping parameter associated with the orientation of the tool 104 and/or energy applicator 114, or enabling position or orientational degrees of freedom for the tool 104 and/or energy applicator 114.

In one implementation, the present disclosure is also directed toward a method of operating the surgical system 100 comprising the impactor assembly 210 having the interface 212 for releasably securing the implantable component 116, the guide 208 having the channel 262 formed to receive the impactor assembly 210, the manipulator 102 configured to support the guide 208 relative to the target site TS along the trajectory T, the sensor 180, and the controller 124 coupled to the manipulator 102 and the sensor 180 and being configured to perform different steps. The steps include: operating the manipulator 102 in the first mode M1 to maintain alignment of the guide 208 with respect to the trajectory T according to the first constraint criteria C1; operating the manipulator 102 in the second mode M2 to maintain alignment of the guide 208 with respect to the trajectory T according to the second constraint criteria C2 different from the first constraint criteria C1; detecting force FD occurring between the target site TS and the manipulator 102 with the sensor 180; and determining that the force FD detected by the sensor 180 satisfies the predetermined condition PC and changing operation of the manipulator 102 from the first mode M1 to the second mode M2 in response.

In this way, the techniques, methods, and embodiments of the surgical system 100 of the present disclosure afford significant advantages in connection with various types of surgical procedures carried out using manipulators 102 to support different types of tools 104 relative to target sites TS. The functionality afforded by the controller 124, the sensing system 206, and the manipulator 102 helps ensure that surgeons and other users are able to carry out surgical procedures in a safe, reliable, and predictable manner. Specifically, the ability to change between modes M1, M2 in response to detecting different types of system conditions SYC which satisfy predetermined conditions PR helps prevent "runaway" conditions (and other types of undesired movement of tools 104) that could otherwise "lift" or "turn" the patient P via the manipulator 102.

Those having ordinary skill in the art will appreciate that aspects of the embodiments described and illustrated herein can be interchanged or otherwise combined.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system comprising:
a tool configured to engage a target site along a trajectory;
a manipulator configured to support the tool;
a sensing system comprising at least one sensor configured to obtain measurements indicative of a force occurring between the target site and the manipulator; and
a controller coupled to the manipulator and to the sensing system, the controller being configured to operate the manipulator between:
a first mode to constrain the tool with respect to the trajectory according to a first stiffness, and
a second mode to constrain the tool with respect to the trajectory according to a second stiffness that is less stiff than the first stiffness; and
wherein the controller is further configured to change operation of the manipulator from the first mode to the second mode in response to determining that the measurements indicative of the force satisfy a predetermined condition.

2. The surgical system of claim 1, wherein the first mode comprises a first number of degrees of freedom in which movement of the tool is restricted relative to the trajectory, and the second mode comprises a second number of degrees of freedom in which movement of the tool is restricted relative to the trajectory, wherein the second number of degrees of freedom is less than the first number of degrees of freedom such that the controller permits movement of the tool relative to the trajectory in at least one more degree of freedom in the second mode as compared with the first mode, wherein the controller is further configured to operate the manipulator:
in the first mode to constrain the tool with respect to the trajectory based on the first number of degrees of freedom; and
in the second mode to constrain the tool with respect to the trajectory based on the second number of degrees of freedom.

3. The surgical system of claim 1, wherein the first mode comprises a first resilience parameter, and the second mode comprises a second resilience parameter, wherein the first resilience parameter and the second resilience parameter are each associated with resilient movement of the tool relative to the trajectory in a common degree of freedom and the controller permits more movement of the tool relative to the trajectory based on the second resilience parameter as compared with the first resilience parameter, wherein the controller is further configured to operate the manipulator:
in the first mode to constrain the tool with respect to the trajectory based on the first resilience parameter; and
in the second mode to constrain the tool with respect to the trajectory based on the second resilience parameter.

4. The surgical system of claim 1, wherein the tool defines a tool center point and wherein the controller is configured to operate the manipulator:
in the first mode to restrict movement of the tool center point away from the trajectory according to the first stiffness; and
in the second mode to permit movement of the tool center point away from the trajectory according to the second stiffness.

5. The surgical system of claim 1, wherein the controller is further configured to operate the manipulator in a third mode to constrain the tool with respect to the trajectory according to a third stiffness different from both the first stiffness and the second stiffness;
wherein the predetermined condition is further defined as a first predetermined condition; and
wherein the controller is further configured to change operation of the manipulator from the second mode to the third mode in response to determining that the measurements indicative of the force satisfy a second predetermined condition different from the first predetermined condition, wherein the force satisfying the second predetermined condition is greater than the force satisfying the first predetermined condition.

6. The surgical system of claim 5, wherein the first mode comprises a first number of degrees of freedom in which movement of the tool is restricted relative to the trajectory, the second mode comprises a second number of degrees of freedom in which movement of the tool is restricted relative to the trajectory, and the third mode comprises a third number of degrees of freedom in which movement of the tool is restricted relative to the trajectory, wherein the third number of degrees of freedom is less than the first number of degrees of freedom and less than the second number of degrees of freedom such that the controller permits movement of the tool relative to the trajectory in at least one more degree of freedom in the third mode as compared with the first mode and the second mode, and wherein the controller is further configured to operate the manipulator:

in the first mode to constrain the tool with respect to the trajectory based on the first number of degrees of freedom;

in the second mode to constrain the tool with respect to the trajectory based on the second number of degrees of freedom; and in the third mode to constrain the tool with respect to the trajectory based on the third number of degrees of freedom.

7. The surgical system of claim 5, wherein the first mode comprises a first resilience parameter, the second mode comprises a second resilience parameter, and the third mode comprises a third resilience parameter, wherein the first, second, and third resilience parameters are each associated with resilient movement of the tool relative to the trajectory in a common degree of freedom and the controller permits more movement of the tool relative to the trajectory based on the third resilience parameter as compared with the first resilience parameter and the second resilience parameter, wherein the controller is further configured to operate the manipulator:

in the first mode to constrain the tool with respect to the trajectory based on the first resilience parameter;

in the second mode to constrain the tool with respect to the trajectory based on the second resilience parameter; and in the third mode to constrain the tool with respect to the trajectory based on the third resilience parameter.

8. The surgical system of claim 1, wherein the controller is further configured to operate the manipulator in the first mode to resist movement of the tool relative to the trajectory with increasing resilience of movement of the tool as the measurements indicative of the force increases toward the predetermined condition.

9. The surgical system of claim 1, wherein:

the tool comprises a guide with a channel formed to receive an impactor assembly and permit limited movement of the impactor assembly relative to the guide, the impactor assembly having an interface for releasably securing a prosthesis; and the manipulator is configured to support the guide along a trajectory relative to the trajectory while the impactor assembly is received in the channel of the guide and while the prosthesis is secured to the impactor assembly;

the target site is further defined as an acetabular cup;

the at least one sensor is configured to detect a force occurring as a result of a force applied on the impactor assembly to install the prosthesis in the acetabular cup;

the controller is further configured to deduce a torque being applied to the acetabular cup based on the detected force; and the controller is further configured to change operation of the manipulator from the first mode to the second mode in response to determining that the deduced torque applied to the acetabular cup satisfies the predetermined condition.

10. The surgical system of claim 1, wherein the predetermined condition is indicative of an actual or a potential runaway condition signifying the target site moves together with the tool.

11. A surgical system comprising:

a tool configured to engage a target site along a trajectory;

a manipulator configured to support the tool along a target axis relative to the trajectory;

a sensing system comprising at least one sensor configured to obtain measurements indicative of a force occurring between the target site and the manipulator; and a controller coupled to the manipulator and to the sensing system, the controller being configured to:

operate the manipulator to constrain the tool along the target axis according to a first stiffness;

determine that the measurements indicative of the force satisfy a predetermined condition; and in response to determining that the measurements indicative of the force satisfy the predetermined condition, operate the manipulator to constrain the tool along the target axis according to a second stiffness that permits greater movement of the tool relative to the target axis as compared with the first stiffness.

12. A method of operating a surgical system, the surgical system comprising a tool configured to engage a target site along a trajectory, a manipulator configured to support the tool, a sensing system comprising at least one sensor configured to obtain measurements indicative of a force occurring between the target site and the manipulator, and a controller coupled to the manipulator and to the sensing system, the method comprising:

operating the manipulator, with the controller, in a first mode to constrain the tool with respect to the trajectory according to a first stiffness;

determining, with the sensing system, that the measurements indicative of the force satisfy a predetermined condition;

changing operation of the manipulator, with the controller, from the first mode to a second mode in response to the sensing system determining that the measurements indicative of the force satisfy the predetermined condition; and operating the manipulator, with the controller, in the second mode to constrain the tool with respect to the trajectory according to a second stiffness that is less stiff than the first stiffness.

13. The method of claim 12, wherein the first mode comprises a first number of degrees of freedom in which movement of the tool is restricted relative to the trajectory, and the second mode comprises a second number of degrees of freedom in which movement of the tool is restricted relative to the trajectory, wherein the second number of degrees of freedom is less than the first number of degrees of freedom such that the controller permits movement of the tool relative to the trajectory in at least one more degree of freedom in the second mode as compared with the first mode, the method comprising:

operating the manipulator, with the controller, in the first mode to constrain the tool with respect to the trajectory based on the first number of degrees of freedom; and operating the manipulator, with the controller, in the second mode to constrain the tool with respect to the trajectory based on the second number of degrees of freedom.

14. The method of claim 12, wherein the first mode comprises a first resilience parameter, and the second mode comprises a second resilience parameter, wherein the first resilience parameter and the second resilience parameter are each associated with resilient movement of the tool relative to the trajectory in a common degree of freedom and the controller permits more movement of the tool relative to the trajectory based on the second resilience parameter as compared with the first resilience parameter, the method comprising:

operating the manipulator, with the controller, in the first mode to constrain the tool with respect to the trajectory based on the first resilience parameter; and operating the manipulator, with the controller, in the second mode to constrain the tool with respect to the trajectory based on the second resilience parameter.

15. The method of claim 12, wherein the tool defines a tool center point, the method comprising:

operating the manipulator, with the controller, in the first mode to restrict movement of the tool center point away from the trajectory according to the first stiffness; and operating the manipulator, with the controller, in the second mode to permit movement of the tool center point away from the trajectory according to the second stiffness.

16. The method of claim 12, wherein the predetermined condition is further defined as a first predetermined condition, the method comprising:

operating the manipulator, with the controller, in a third mode to constrain the tool with respect to the trajectory according to a third stiffness different from both the first stiffness and the second stiffness;

determining, with the sensing system, that the measurements indicative of the force satisfy a second predetermined condition different from the first predetermined condition; and changing operation of the manipulator, with the controller, from the second mode to the third mode in response to the sensing system determining that the measurements indicative of the force satisfy the second predetermined condition.

17. The method of claim 12, comprising:

operating the manipulator, with the controller, in the first mode to resist movement of the tool relative to the trajectory and increasing resilience of movement of the tool as the measurements indicative of the force increases toward the predetermined condition.

18. The method of claim 12, wherein, the target site is further defined as an acetabular cup and the tool comprises a guide with a channel formed to receive an impactor assembly and permit limited movement of the impactor assembly relative to the guide, the impactor assembly having an interface for releasably securing a prosthesis, the method comprising:

supporting, with the manipulator, the guide along the trajectory relative to the target site while the impactor assembly is received in the channel of the guide and while the prosthesis is secured to the impactor assembly;

detecting, with the sensing system, a force occurring as a result of a force applied on the impactor assembly to install the prosthesis in the acetabular cup;

deducing, with the controller, a torque being applied to the acetabular cup based on the detected force; and changing operation of the manipulator, with the controller, from the first mode to the second mode in response to determining that the deduced torque applied to the acetabular cup satisfies the predetermined condition.

19. The method of claim 12, wherein the predetermined condition is indicative of an actual or a potential runaway condition signifying the target site moves together with the tool.

\* \* \* \* \*